(12) United States Patent
Zhang et al.

(10) Patent No.: US 7,507,739 B2
(45) Date of Patent: Mar. 24, 2009

(54) 6-[(SUBSTITUTED)PHENYL]TRIAZOLOPY-RIMIDINES AS ANTICANCER AGENTS

(75) Inventors: Nan Zhang, Bayside, NY (US); Semiramis Ayral-Kaloustian, Tarrytown, NY (US); Thai Nguyen, Fair Lawn, NJ (US); Yanzhong Wu, Bronx, NY (US); Wei Tong, Suffern, NY (US)

(73) Assignee: Wyeth, Madison, NJ (US)

( * ) Notice: Subject to any disclaimer, the term of this patent is extended or adjusted under 35 U.S.C. 154(b) by 425 days.

(21) Appl. No.: 10/950,543

(22) Filed: Sep. 24, 2004

(65) Prior Publication Data

US 2005/0090508 A1 Apr. 28, 2005

Related U.S. Application Data

(60) Provisional application No. 60/505,544, filed on Sep. 24, 2003.

(51) Int. Cl.
  C07D 487/04 (2006.01)
  A61K 31/519 (2006.01)
  A61P 35/04 (2006.01)

(52) U.S. Cl. .................... 514/259.3; 544/263
(58) Field of Classification Search ................ 544/263, 544/118; 514/259.31, 234.2
  See application file for complete search history.

(56) References Cited

U.S. PATENT DOCUMENTS

| 5,593,996 | A | * | 1/1997 | Pees et al. ............ 514/259.31 |
| 5,612,345 | A | | 3/1997 | Becher et al. |
| 5,750,766 | A | | 5/1998 | Krummel et al. |
| 5,756,509 | A | | 5/1998 | Pees |
| 5,808,066 | A | | 9/1998 | Krummel et al. |
| 5,817,663 | A | | 10/1998 | Pees et al. |
| 5,854,252 | A | | 12/1998 | Pees et al. |
| 5,948,783 | A | | 9/1999 | Pees et al. |
| 5,955,252 | A | | 9/1999 | Goto et al. |
| 5,965,561 | A | | 10/1999 | Pees et al. |
| 5,981,534 | A | | 11/1999 | Pfrengle |
| 5,985,883 | A | | 11/1999 | Pees |
| 5,986,135 | A | | 11/1999 | Pfrengle et al. |
| 5,994,360 | A | | 11/1999 | Pfrengle |
| 6,020,338 | A | | 2/2000 | Pfrengle et al. |
| 6,117,865 | A | | 9/2000 | Pees |
| 6,117,876 | A | | 9/2000 | Pees et al. |
| 6,124,301 | A | | 9/2000 | Aven et al. |
| 6,204,269 | B1 | | 3/2001 | Pfrengle et al. |
| 6,242,451 | B1 | | 6/2001 | Pees |
| 6,255,309 | B1 | | 7/2001 | Pees et al. |
| 6,268,371 | B1 | | 7/2001 | Sieverding et al. |
| 6,277,856 | B1 | | 8/2001 | Cotter et al. |
| 6,284,762 | B1 | | 9/2001 | Pfrengle |
| 6,297,251 | B1 | | 10/2001 | Pees et al. |
| 6,387,848 | B1 | | 5/2002 | Aven et al. |
| 6,518,275 | B1 | | 2/2003 | Cotter et al. |
| 6,521,628 | B1 | | 2/2003 | Cotter et al. |
| 6,699,874 | B2 | | 3/2004 | Cotter et al. |
| 2002/0045631 | A1 | | 4/2002 | Aven et al. |
| 2002/0061882 | A1 | | 5/2002 | Pees et al. |
| 2002/0068744 | A1 | * | 6/2002 | Schmitt et al. ......... 514/259.31 |
| 2002/0198222 | A1 | | 12/2002 | Bruns et al. |
| 2003/0055069 | A1 | | 3/2003 | Pees et al. |
| 2004/0097522 | A1 | | 5/2004 | Gebauer et al. |
| 2005/0090508 | A1 | | 4/2005 | Zhang et al. |

FOREIGN PATENT DOCUMENTS

| EP | 0 550 113 A2 | 7/1993 |
| EP | 0 782 997 A2 | 7/1997 |
| EP | 0 550 113 B1 | 10/1997 |
| EP | 0 834 513 A2 | 4/1998 |
| EP | 0 562 615 B1 | 6/1998 |
| EP | 0 945 453 A1 | 9/1999 |
| EP | 0 989 130 A1 | 3/2000 |
| EP | 0 988 790 B1 | 5/2003 |
| EP | 0 943 241 B1 | 6/2003 |

(Continued)

OTHER PUBLICATIONS

Harvey C. Brill; J. Am. Chem. Soc.; vol. 54; pp. 2484-2487; 1932.

(Continued)

*Primary Examiner*—Brenda L Coleman
*Assistant Examiner*—Susanna Moore
(74) *Attorney, Agent, or Firm*—Stephen E. Johnson

(57) ABSTRACT

This invention relates to certain 6-[(substituted)phenyl]triazolopyrimidine compounds or pharmaceutically acceptable salts thereof, and compositions containing said compounds or pharmaceutically acceptable salts thereof, wherein said compounds are anti-cancer agents useful for the treatment of cancer in mammals. This invention further relates to a method of treating or inhibiting the growth of cancerous tumor cells and associated diseases in a mammal and further provides a method for the treatment or prevention of cancerous tumors that express multiple drug resistance (MDR) or are resistant because of MDR, in a mammal in need thereof which method comprises administering to said mammal an effective amount of said compounds or pharmaceutically acceptable salts thereof. The present invention relates to a method of treating or inhibiting the growth of cancerous tumor cells and associated diseases in a mammal in need thereof by promotion of microtubule polymerization which comprises administering to said mammal an effective amount of said compounds and pharmaceutically acceptable salts thereof.

32 Claims, No Drawings

FOREIGN PATENT DOCUMENTS

| | | |
|---|---|---|
| EP | 0770615 B1 | 6/2008 |
| ER | 0 562 615 A1 | 9/1993 |
| FR | 2 784 381 | 4/2000 |
| WO | WO 94/20501 A1 | 9/1994 |
| WO | WO 98/41496 A1 | 9/1998 |
| WO | WO 98/46607 A1 | 10/1998 |
| WO | WO 98/46608 A1 | 10/1998 |
| WO | WO 99/41255 A1 | 8/1999 |
| WO | WO 99/48893 A1 | 9/1999 |
| WO | WO 00/18227 A1 | 4/2000 |
| WO | WO 01/35738 A2 | 5/2001 |
| WO | WO 02/02563 A2 | 1/2002 |
| WO | WO 02/38565 A2 | 5/2002 |
| WO | WO 02/46195 A1 | 6/2002 |
| WO | WO 02/50077 A2 | 6/2002 |
| WO | WO 02/067679 A1 | 9/2002 |
| WO | WO 02/083676 A1 | 10/2002 |
| WO | WO 03/008416 A1 | 1/2003 |
| WO | WO 2005/030775 A | 4/2005 |

OTHER PUBLICATIONS

M.C. Wani, et al.; J. Am. Chem. Soc.; vol. 93; pp. 2325-2327; 1971.
Richard A.Y. Jones, et al..; J. Chem. Soc. (B); pp. 1300-1315; 1971.
Steven R. Koepke, et al.; J. Org. Chem.; vol. 44; No. 15; pp. 2718-2722; 1979.
Schiff, et al.; Nature; vol. 277; pp. 665-667; 1979.
Nirbhay Kumar; J. Biol. Chem.; vol. 256; No. 20; pp. 10435-10441; 1981.
Ernest Hamel, et. al.; J. Biol. Chem; vol. 259; No. 4; pp. 2501-2508; 1984.
Ding-Wu Shen, et al.; J. Biol. Chem.; vol. 261, No. 17; pp. 7762-7770; 1986.
Tim McGrath and Melvin S. Center; Biochem. Biophys. Res. Commun.; vol. 145; No. 3; pp. 1171-1176; 1987.
William P. McGuire, et al.; Ann. Int. Med.; vol. III; pp. 273-279; 1989.
Lori J. Goldstein, et al.; J. Natl. Cancer Inst. (Bethesda); vol. 81; pp. 116-124; 1989.
Eric K. Rowinsky, et al.; J. Natl. Cancer Inst.; vol. 82; No. 15; pp. 1247-1259; 1990.
Frankie Ann Holmes, et al.; J. Natl. Cancer Inst.; vol. 83; No. 24; pp. 1797-1805; 1991.
Annette Bicher, et al.; Anti-Cancer Drugs; vol. 4; pp. 141-148; 1993.
Elsie C. Kohn, et al.; Natl. Cancer Inst.; vol. 86; No. 1; pp. 18-24; 1994.
Marco Chini, et al.; Tetr. Lett.; vol. 35; No. 5; pp. 761-764; 1994.
Robert A. Holton, et al.; J. Am. Chem. Soc.; vol. 116; No. 4; pp. 1597-1600, 1994.
Fanny Monteil, et. al.; J. Organomet Chem.; vol. 480; pp. 117-184; 1994.
K.C. Nicolaou, et al.; Nature; vol. 367; pp. 630-634; 1994.
Mary Ann Jordan, et. al.; Cancer Res.; vol. 56; pp. 816-825; 1996.
Ernest Hamel; Med. Res. Rev.; vol. 16; pp. 207-231; 1996.
Sridhar K. Rabindran, et al.; Cancer Res.; vol. 58; pp. 5850-5858; 1998.
Takahiro Oka and Akio Murai; Tetrahedron; vol. 54; pp. 1-20; 1998.
Chun Li, et al.; Science & Medicine; vol. Jan./Feb.; pp. 38-47; 1999.
Eric K. Rowinsky and Anthony W. Tolcher; Cancer Principles and Practice; pp. 431-452; 2001.
Michael M. Gottesman; Annu. Rev. Med.; vol. 53; pp. 615-627; 2002.
Michael M. Gottesman, et al.; Nature Rev. Cancer; vol. 2; pp. 48-58; 2002.
Frank Loganzo, et al.; Cancer Res.; vol. 63; pp. 1838-1845; 2003.
U.S. Appl. No. 11/451,078, filed Jun. 2006, Wu et al.
Conley et al. 2001; Encyclopedia of Reagents for Organic Synthesis; Tripropylamine; p. 1-3.
Sorgi et al. 2001; Encyclopedia of Reagents for Organic Synthesis; Triethylamine; p. 1-12.
Sorgi et al. 2001; Encyclopedia of Reagents for Organic Synthesis; Diisopropylethylamine; p. 1-10.
Gawley et al. 2006; Encyclopedia of Reagents for Organic Synthesis; Sodium Hydride; p. 1-20.
Caine et al. 2006; Encyclopedia of Reagents for Organic Synthesis; Potassium t-Butoxide; p. 1-36.

* cited by examiner

6-[(SUBSTITUTED)PHENYL]TRIAZOLOPY-RIMIDINES AS ANTICANCER AGENTS

"This application claims priority from Provisional Application No. 60/505,544 filed Sep. 24, 2003 the entire disclosure of which is hereby incorporated by reference".

FIELD OF THE INVENTION

The present invention relates to certain 6-[(substituted) phenyl]-triazolopyrimidine compounds or pharmaceutically acceptable salts thereof, and compositions containing said compounds or pharmaceutically acceptable salts thereof, wherein said compounds are anti-cancer agents useful for the treatment of cancer in mammals, treatment or prevention of cancerous tumors that express multiple drug resistance (MDR) or are resistant because of MDR, a method of treating or inhibiting the growth of cancerous tumor cells and associated diseases in a mammal in need thereof by promotion of microtubule polymerization and a method of treating or inhibiting the growth of cancerous tumors in a mammal with inherent or acquired resistance to chemotherapeutic agents used in chemotherapy treatment and in particular antimitotic agents by administering an effective amount of a compound of the invention and pharmaceutically acceptable salts thereof.

BACKGROUND OF THE INVENTION

Most of the cytostatics in use today either inhibit the formation of essential precursors for biosynthesis of DNA or block DNA polymerases or interfere with the template function of DNA because DNA was the primary target for developing therapeutic drugs for chemotherapy. Unfortunately, inhibition of the formation of essential precursors for biosynthesis of DNA or blocking DNA polymerases or interference with the template function of DNA also affects normal tissues.

Antimicrotubule drugs are a major category of anticancer agents (Rowinsky, E. K., and Tolcher, A. W. Antimicrotubule agents. In: V. T. Devita, Jr., S. Hellman, and S. A. Rosenberg (eds.), Cancer Principles and Practice, Ed. 6, pp. 431-452. Philadelphia: Lippincott Williams and Wilkins, 2001). They work by interfering with the function of cellular microtubules, particularly the mitotic spindle. The disruption of normal spindle function leads to apoptotic cell death.

Currently, there are three major classes of known antimicrotubule pharmacological agents. Each has a distinct binding region on β-tubulin and distinct effects on microtubule function. These classes are: 1) taxane-site agents which promote microtubule formation and stabilize microtubules; 2) vinca/peptide-site agents which destabilize microtubules and often induce formation of abnormal polymers or aggregates at high concentrations; and 3) colchicine-site agents which also destabilize microtubules and generally do not induce other polymers (Hamel, E. Antimitotic natural products and their interactions with tubulin. Med. Res. Rev., 16:207-231, 1996). Most of the ligands for all three classes of sites are natural products or semi-synthetic derivatives of natural products.

Paclitaxel and its semisynthetic derivative docetaxel (Taxotere®) interfere with microtubule formation and stabilize microtubules. Paclitaxel (Taxol®), is a diterpene isolated from the bark of the Western (Pacific) yew, *Taxus brevifolia* and is representative of a new class of therapeutic agent having a taxane ring system. It was additionally found in other members of the Taxacae family including the yew of Canada (*Taxus canadensis*) found in Gaspesia, eastern Canada and *Taxus baccata* found in Europe whose needles contain paclitaxel and analogs and hence provide a renewable source of paclitaxel and derivatives. The crude extract was tested for the first time during the 1960s and its active principle was isolated in 1971 and the chemical structure identified (M. C. Wani et al, J. Am. Chem. Soc., 93, 2325 (1971)). Further, a wide range of activity over melanoma cells, leukemia, various carcinomas, sarcomas and non-Hodgkin lymphomas as well as a number of solid tumors in animals was shown through additional testing. Paclitaxel and its analogs have been produced by partial synthesis from 10-deacetylbaccatin III, a precursor obtained from yew needles and twigs, and by total synthesis (Holton, et al., J. Am. Chem. Soc. 116:1597-1601 (1994) and Nicolaou, et al., Nature 367:630-634 (1994)). Paclitaxel has been demonstrated to possess antineoplastic activity. More recently, it was shown that the antitumor activity of paclitaxel is due to a promotion of microtubule polymerization (Kumar, N., J. Biol. Chem. 256:10435-10441 (1981); Rowinsky, et al., J. Natl. Cancer Inst., 82:1247-1259 (1990); and Schiff, et al., Nature, 277:665-667 (1979)). Paclitaxel has now demonstrated efficacy in several human tumors in clinical trials (McGuire, et al., Ann. Int. Med., 111:273-279 (1989); Holmes, et al., J. Natl. Cancer Inst., 83:1797-1805 (1991); Kohn et al., J. Natl. Cancer Inst., 86:18-24 (1994); and A. Bicker et al., Anti-Cancer Drugs, 4, 141-148 (1993).

Two taxane-site agents (paclitaxel and docetaxel) and three vinca/peptide-site agents (vinblastine, vincristine, and vinorelbine) are used clinically to treat various human cancers. Taxanes have proven to be of greater utility against solid tumors (e.g., lung, breast, ovarian) than the vinca alkaloids, suggesting that agents that promote microtubule formation might be superior clinically to those that destabilize microtubules. Colchicine-site agents are not used therapeutically.

Despite the widespread clinical use of paclitaxel and docetaxel, these drugs have several limitations that create a need for improved agents. First, many tumors are inherently resistant (e.g., colon tumors) or become resistant after multiple cycles of treatment, at least in part due to the expression of drug transporters located in cancer cell membranes that pump the drugs out of cells and thereby decrease their efficacy (Gottesman, M. M. Mechanisms of cancer drug resistance. Annu. Rev. Med., 53: 615-627, 2002). The best known of these transporters is P-glycoprotein. Accordingly, there is a need for new agents with taxane-like effects on microtubule polymerization that are not substrates of P-glycoprotein or other such pumps and that therefore will overcome this cause of taxane resistance in patients.

Second, paclitaxel and docetaxel have poor water solubility and paclitaxel must be formulated in Cremophor EL, a vehicle that induces serious hypersensitivity reactions (Li, C. L., Newman, R. A., and Wallace, S. Reformulating paclitaxel. Science & Medicine, Jan/Feb: 38-47,1999). Patients are typically premedicated with corticosteroids and antihistamines before administration of paclitaxel to minimize these toxicities. Accordingly, there is a need for new agents with taxane-like effects on microtubule polymerization that are highly water soluble and can be administered in physiological saline or other suitable non-toxic vehicle.

Third, paclitaxel is a natural product having a highly complex structure, and docetaxel is a closely related semisynthetic derivative. Therefore there is a need for compounds which are readily available through synthesis, are structurally different from taxanes and which have taxane-like effects on microtubule polymerization.

Accordingly, there is still a need in the art for cytotoxic agents for use in cancer therapy. In particular, there is a need for cytotoxic agents which inhibit or treat the growth of tumors which have an effect similar to paclitaxel and interfere with the process of microtubule formation. Additionally, there is a need in the art for agents which accelerate tubulin polymerization and stabilize the assembled microtubules.

Accordingly, it would be advantageous to provide new compounds which provide a method of treating or inhibiting cell proliferation, neoplastic growth and malignant tumor growth in mammals by administering compounds which have paclitaxel like anticancer activity.

Additionally, it would be advantageous to provide new compounds which provide a method for treating or inhibiting growth of cancerous tumors that express multiple drug resistance (MDR) or are resistant because of MDR.

Further, it would be advantageous to provide new compounds which provide a method of treating or inhibiting the growth of cancerous tumors in a mammal with inherent or acquired resistance to chemotherapeutic agents and in particular antimitotic agents.

Described in the art is the preparation and use of substituted triazolopyrimidines in agriculture as fungicides in U.S. Pat. Nos. 5,593,996; 5,756,509; 5,948,783; 5,981,534; 5,612,345; 5,994,360; 6,020,338; 5,985,883; 5,854,252; 5,808,066; 5,817,663; 5,955,252; 5,965,561; 5,986,135; 5,750,766; 6,117,865; 6,117,876; 6,124,301; 6,204,269; 6,255,309; 6,268,371; 6,277,856; 6,284,762; 6,297,251; 6,387,848; U.S. Patent Application Publication U.S. 2002/0045631A1; U.S. 2002/0061882A1; U.S. 20030055069A1 and International Publication Numbers: WO98/46607; WO98/46608; WO99/48893; WO99/41255; WO00/18227; WO01/35738A2; WO02/46195A1; WO02/067679A1; WO02/083676A1; EPO 834513A2; EPO 782997A2; EPO550113B1; FR2784381 A1; EPO 989130A1; WO98/41496; WO94/20501; EPO 945453A1; EPO 562615A1; EPO 562615B1; EP 0 550113A2; EP 0 943241 B1; EP 0 988790 B1 and having the following general formula:

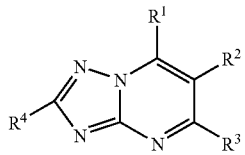

Disclosed in international publication WO 02/02563 is the use of triazolopyrimidines as anticancer agents.

The compounds of the present invention are a new class of taxane-like agents that satisfy the hereinbefore described needs, and that differ in significant ways from the previously known classes of antimicrotubule compounds. The compounds of this invention bind at the vinca site of β-tubulin, yet they have many properties that are similar to taxanes and distinct from vinca-site agents. In particular, the compounds of this invention enhance the polymerization of microtubule-associated protein (MAP)-rich tubulin in the presence of GTP at low compound:tubulin molar ratios, in a manner similar to paclitaxel and docetaxel. The compounds of this invention also induce polymerization of highly purified tubulin in the absence of GTP under suitable experimental conditions, an activity that is a hallmark of taxanes. The compounds of the present invention are potently cytotoxic for many human cancer cell lines in culture, including lines that overexpress the membrane transporters MDR (P-glycoprotein), MRP, and MXR, thus making them active against cell lines that are resistant to paclitaxel and vincristine. In particular, representative examples of this invention have high water solubility and can be formulated in saline. Representative examples of this invention are active as anti-tumor agents in athymic mice bearing human tumor xenografts of lung and colon carcinoma, melanoma, and glioblastoma, when dosed either intravenously or orally.

SUMMARY OF THE INVENTION

In accordance with the present invention, there is provided compounds represented by Formula (I):

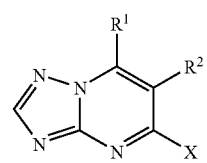

(I)

wherein:
$R^1$ is selected from

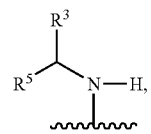

and $C_6$-$C_8$ cycloalkyl optionally substituted with $R^8$;
$R^2$ is a moiety of the group

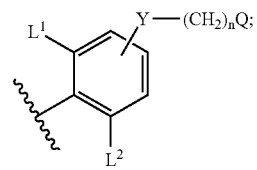

n is an integer of 2, 3, or 4;
X is Cl or Br;
Y is O, S, $CH_2$ or $NR^4$;
Q is selected from —$NR^6R^7$ and —OH;
$L^1$ and $L^2$ are each independently H, F, Cl, Br, or $CF_3$;
$R^3$ is $CF_3$ or $C_2F_5$;
$R^4$ and $R^5$ are each independently H or $C_1$-$C_3$ alkyl;
$R^6$ and $R^7$ are each independently H or $C_1$-$C_3$ alkyl; or
$R^6$ and $R^7$ when optionally taken together with the nitrogen atom to which each is attached form a 4 to 6 membered saturated heterocyclic ring having 1-2 nitrogen atoms and 0-1 oxygen atoms or 0-1 sulfur atoms, and optionally substituted with $R^8$;
$R^8$ is $C_1$-$C_3$ alkyl;
or pharmaceutically acceptable salts thereof.

Definitions

The term alkyl means a straight or branched chain alkyl moiety of 1 to 3 carbon atoms.

The term t-BOC as used herein means tert-butoxy carbonyl.

The term aminoalkoxy means a moiety of the formula

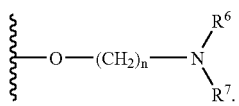

The term aminoalkyl means a moiety of the formula

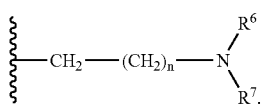

The term aminoalkylthio means a moiety of the formula

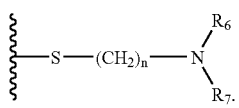

The term aminoalkylamino means a moiety of the formula

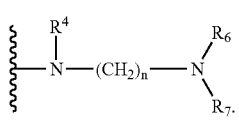

The term hydroxyalkoxy means a moiety of the formula

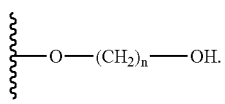

The term alkali metal hydroxide includes lithium, potassium or sodium hydroxide.

The term alkali metal carbonate includes lithium, potassium or sodium carbonate.

The term alkali metal hydride includes lithium, potassium or sodium hydride.

The term strong base means an alkali metal hydroxide, alkali metal carbonate and alkali metal hydride (e.g., sodium hydride).

Phenyl as used herein refers to a 6-membered carbon aromatic ring.

Cycloalkyl as used herein means a saturated carbocyclic monocyclic ring having from 6 to 8 carbon atoms optionally substituted with $C_1$-$C_3$ alkyl. Non-limiting representative examples include: cyclohexyl, cycloheptyl and cyclooctyl.

As used herein a saturated heterocyclic ring is a 4 to 6 membered ring atoms having 1-2 nitrogen atoms, 0-1 oxygen atoms and 0-1 sulfur atoms and optionally substituted with $C_1$-$C_3$ alkyl. Non-limiting representative examples include: morpholine, piperidine, pyrrolidine, piperazine, azetidine and N-methyl-piperazine.

The present invention provides a method of treating or inhibiting the growth of cancerous tumor cells and associated diseases in a mammal by administering an effective amount of the compounds of Formula (I) and pharmaceutically acceptable salts thereof in need thereof.

The present invention also provides a method of treating or inhibiting the growth of cancerous tumor cells and associated diseases in mammals in need thereof by interacting with tubulin and microtubules by promotion of microtubule polymerization which comprises administering to said mammal an effective amount of the compounds of Formula (I) and pharmaceutically acceptable salts thereof.

Further provided is a method for the treatment or prevention of tumors that express multiple drug resistance (MDR) or are resistant because of MDR in a mammal in need thereof which method comprises administering to said mammal an effective amount of such compounds or pharmaceutically acceptable salts thereof.

This invention also provides a method of promoting tubulin polymerization in a tubulin containing system by contacting said tubulin containing system with an effective amount of a compound of Formula (I) or pharmaceutically acceptable salts thereof.

Additionally this invention provides a method of stabilizing microtubules in a tubulin containing system which comprises contacting said tubulin containing system with an effective amount of a compound of Formula (i) or a pharmaceutically acceptable salt thereof.

Further provided is a method of treating, inhibiting the growth of, or eradicating a tumor in a mammal in need thereof wherein said tumor is resistant to at least one chemotherapeutic agent which comprises administering to said mammal an effective amount of the compounds of Formula (I) and pharmaceutically acceptable salts thereof.

In yet a further aspect this invention provides a compound of Formula (I) in combination or association with a pharmaceutically acceptable carrier. In particular, the present invention provides a pharmaceutical composition which comprises an effective amount of a compound of Formula (I) and a pharmaceutically acceptable carrier.

The compounds of this invention may contain an asymmetric carbon atom and some of the compounds of this invention may contain one or more asymmetric centers and may thus give rise to stereoisomers, such as enantiomers and diastereomers. The stereoisomers of the instant invention are named according to the Cahn-Ingold-Prelog System. While shown without respect to stereochemistry in Formula (I), the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. Included in the scope of the present invention are (R) and (S) isomers of compounds of general Formula (I) having a chiral center and the racemates thereof. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

Optical isomers may be obtained in pure form by standard separation techiques or enantiomer specific synthesis.

Also, the polymorphs, hydrates and solvates of the compounds of the present invention are included within the scope of the invention.

A preferred embodiment of the invention is the compound of formula (Ia) as shown below:

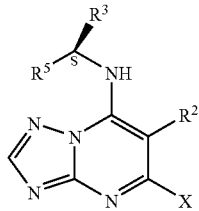
(Ia)

or pharmaceutically acceptable salts thereof.

A preferred embodiment of the invention is the compound of formula (Ib) as shown below:

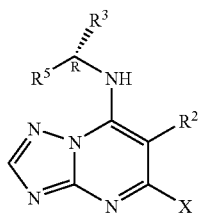
(Ib)

or pharmaceutically acceptable salts thereof.

Further preferred are compounds of Formula (I) wherein $R^2$ is

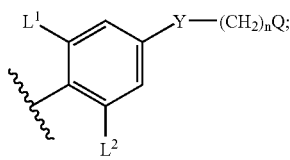

or pharmaceutically acceptable salts thereof.

Also preferred are compounds of Formula (I) where $R^1$ is $C_6$-$C_8$ cycloalkyl optionally substituted with $R^8$ or pharmaceutically acceptable salts thereof.

Among the more preferred group of compounds of this invention according to Formula (Ia) including pharmaceutically acceptable salts thereof are those selected from the subgroups a), and b) below:

a)
$R^2$ is

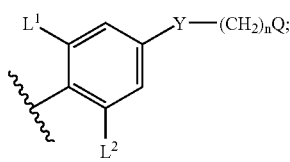

n=3;
X is Cl or Br;
Y is O;
$R^3$ is $CF_3$;
Q is —$NR^6R^7$;
$R^5$ is H or methyl;
$R^6$ and $R^7$ each independently H or $C_1$-$C_3$ alkyl; or
$R^6$ and $R^7$ when optionally taken together with the nitrogen atom to which each is attached form a 4 to 6 membered saturated heterocyclic ring with 1-2 nitrogen atoms, 0-1 oxygen atoms and 0-1 sulfur atoms, and optionally substituted with $R^8$;
$R^8$ is $C_1$-$C_3$ alkyl;
$L^1$ is F;
$L^2$ is H or F;

or pharmaceutically acceptable salts thereof and b)
$R^2$ is

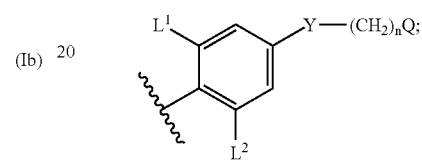

n is 3;
X is Cl;
Y is O;
Q is —$NR^6R^7$;
$R^6$ is methyl;
$R^7$ is H or methyl;
$L^1$ is F;
$L^2$ is F;

or pharmaceutically acceptable salts thereof.

Among the more preferred group of compounds of this invention according to Formula (I) including pharmaceutically acceptable salts thereof are the subgroup below:
$R^1$ is $C_6$-$C_8$ cycloalkyl;
$R^2$ is

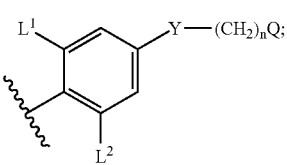

n is 3;
X is Cl;
Y is O;
Q is —$NR^6R^7$;
$R^6$ is methyl;
$R^7$ is H or methyl;
$L^1$ is F;
$L^2$ is F;

or pharmaceutically acceptable salts thereof.

Among the most preferred group of compounds of this invention according to formula (Ia) including pharmaceutically acceptable salts thereof are those of the group below:
$R^2$ is

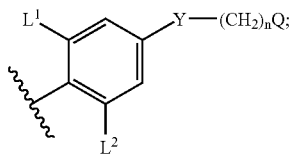

X is Cl;
n is 3;
Y is O;
Q is —NR$^6$R$^7$;
R$^3$ is CF$_3$,
R$^5$ is H or methyl,
R$^6$ is methyl;
R$^7$ is H or methyl;
L$^1$ is F;
L$^2$ is F;

or pharmaceutically acceptable salts thereof.

Among the most preferred group of compounds of this invention according to formula (Ib) including pharmaceutically acceptable salts thereof are those of the group below: R$^2$ is

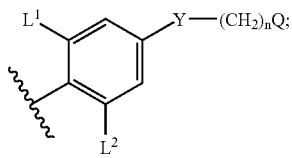

X is Cl;
n is 3;
Y is O;
Q is —NR$^6$R$^7$;
R$^3$ is CF$_3$,
R$^5$ is H or methyl,
R$^6$ is methyl;
R$^7$ is H or methyl;
L$^1$ is F;
L$^2$ is F;

or pharmaceutically acceptable salts thereof.

Specifically preferred compounds of this invention according to Formula (I) are the following compounds or pharmaceutically acceptable salts thereof:

5-chloro-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine, 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine, 5-chloro-6-{2,6-difluoro-4-[3-(methylamino)propoxy]phenyl}-N-(2,2,2-trifluoroethyl)[1,2,4]triazolo[1,5-a]pyrimidin-7-amine, 5-chloro-6-{4-[3-(dimethylamino)propoxy]-2,6-difluorophenyl}-N-(2,2,2-trifluoroethyl)[1,2,4]triazolo[1,5-a]pyrimidin-7-amine, 6-[4-(3-aminopropoxy)-2,6-difluorophenyl]-5-chloro-N-[(1S)-2,2,2-trifluoro-1-methylethyl][1,2,4]triazolo[1,5-a]pyrimidin-7-amine, 5-chloro-6-{2,6-difluoro-4-[3-(4-methylpiperazin-1-yl)propoxy]phenyl}-N-[(1S)-2,2,2-trifluoro-1-methylethyl][1,2,4]triazolo[1,5-a]pyrimidin-7-amine, 5-chloro-6-{4-[3-(ethylamino)propoxy]-2,6-difluorophenyl}-N-[(1S)-2,2,2-trifluoro-1-methylethyl][1,2,4]triazolo[1,5-a]pyrimidin-7-amine, 5-chloro-6-(4-{3-[ethyl(methyl)amino]propoxy}-2,6-difluorophenyl)-N-[(1S)-2,2,2-trifluoro-1-methylethyl][1,2,4]triazolo[1,5-a]pyrimidin-7-amine, 5-chloro-6-[2,6-difluoro-4-(3-pyrrolidin-1-ylpropoxy)phenyl]-N-[(1S)-2,2,2-trifluoro-1-methylethyl][1,2,4]triazolo[1,5-a]pyrimidin-7-amine, 5-chloro-6-[2,6-difluoro-4-(3-piperidin-1-ylpropoxy)phenyl]-N-[(1S)-2,2,2-trifluoro-1-methylethyl][1,2,4]triazolo[1,5-a]pyrimidin-7-amine, 5-chloro-6-[2,6-difluoro-4-(3-morpholin-4-ylpropoxy)phenyl]-N-[(1S)-2,2,2-trifluoro-1-methylethyl][1,2,4]triazolo[1,5-a]pyrimidin-7-amine, 6-[4-(3-azetidin-1-ylpropoxy)-2,6-difluorophenyl]-5-chloro-N-[(1S)-2,2,2-trifluoro-1-methylethyl][1,2,4]triazolo[1,5-a]pyrimidin-7-amine, 5-chloro-6-{4-[3-(dimethylamino)propoxy]-2-fluorophenyl}-N-[(1S)-2,2,2-trifluoro-1-methylethyl][1,2,4]triazolo[1,5-a]pyrimidin-7-amine, 5-chloro-6-{2,6-difluoro-4-[2-(methylamino)ethoxy]phenyl}-N-[(1S)-2,2,2-trifluoro-1-methylethyl][1,2,4]triazolo[1,5-a]pyrimidin-7-amine, 5-chloro-6-{4-[4-(dimethylamino)butoxy]-2,6-difluorophenyl}-N-[(1S)-2,2,2-trifluoro-1-methylethyl][1,2,4]triazolo[1,5-a]pyrimidin-7-amine, 5-chloro-6-{4-[2-(dimethylamino)ethoxy]-2,6-difluorophenyl}-N-[(1S)-2,2,2-trifluoro-1-methylethyl][1,2,4]triazolo[1,5-a]pyrimidin-7-amine, 5-chloro-6-[2,6-difluoro-4-(2-morpholin-4-ylethoxy)phenyl]-N-[(1S)-2,2,2-trifluoro-1-methylethyl][1,2,4]triazolo[1,5-a]pyrimidin-7-amine, 5-chloro-6-(4-{[3-(dimethylamino)propyl]thio}-2,6-difluorophenyl)-N-[(1S)-2,2,2-trifluoro-1-methylethyl][1,2,4]triazolo[1,5-a]pyrimidin-7-amine, 2-[4-(5-chloro-7-{[(1S)-2,2,2-trifluoro-1-methylethyl]amino}[1,2,4]triazolo[1,5-a]pyrimidin-6-yl)-3,5-difluorophenoxy]ethanol, 3-[4-(5-chloro-7-{[(1S)-2,2,2-trifluoro-1-methylethyl]amino}[1,2,4]triazolo[1,5-a]pyrimidin-6-yl)-3,5-difluorophenoxy]propan-1-ol, 4-[4-(5-chloro-7-{[(1S)-2,2,2-trifluoro-1-methylethyl]amino}[1,2,4]triazolo[1,5-a]pyrimidin-6-yl)-3,5-difluorophenoxy]butan-1-ol, N$^1$-[4-(5-chloro-7-{[(1S)-2,2,2-trifluoro-1-methylethyl]amino}[1,2,4]triazolo[1,5-a]pyrimidin-6-yl)-3,5-difluorophenyl]-N',N$^3$,N$^3$-trimethylpropane-1,3-diamine, N$^1$-[4-(5-chloro-7-{[(1S)-2,2,2-trifluoro-1-methylethyl]amino}[1,2,4]triazolo[1,5-a]pyrimidin-6-yl)-3,5-difluorophenyl]-N$^3$,N$^3$-dimethylpropane-1,3-diamine, N$^1$-[4-(5-chloro-7-{[(1S)-2,2,2-trifluoro-1-methylethyl]amino}[1,2,4]triazolo[1,5-a]pyrimidin-6-yl)-3,5-difluorophenyl]-N$^2$,N$^2$-dimethylethane-1,2-diamine, 5-bromo-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine, 5-chloro-6-{4-[4-(dimethylamino)butyl]-2,6-difluorophenyl}-N-[(1S)-2,2,2-trifluoro-1-methylethyl][1,2,4]triazolo[1,5-a]pyrimidin-7-amine, 5-chloro-6-{3-[2-(dimethylamino)ethoxy]-2,6-difluorophenyl}-N-[(1S)-2,2,2-trifluoro-1-methylethyl][1,2,4]triazolo[1,5-a]pyrimidin-7-amine, 5-chloro-6-{3-[3-(dimethylamino)propoxy]-2,6-difluorophenyl}-N-[(1S)-2,2,2-trifluoro-1-methylethyl][1,2,4]triazolo[1,5-a]pyrimidin-7-amine, 5-chloro-6-{3-[4-(dimethylamino)butoxy]-2,6-difluorophenyl}-N-[(1S)-2,2,2-trifluoro-1-methylethyl][1,2,4]triazolo[1,5-a]pyrimidin-7-amine, 3-[4-(5-chloro-7-cycloheptyl[1,2,4]triazolo[1,5-a]pyrimidin-6-yl)-3,5-difluorophenoxy]propan-1-ol, 3-[4-(5-chloro-7-cycloheptyl[1,2,4]triazolo[1,5-a]pyrimidin-6-yl)-3,5-difluorophenoxy]-N,N-dimethylpropan-1-amine, 3-[4-(5-chloro-7-cycloheptyl[1,2,4]triazolo[1,5-a]pyrimidin-6-yl)-3,5-difluorophenoxy]-N-methylpropan-1-amine, 5-chloro-6-{2,6-difluoro-4-[3-(methylamino)propoxy]phenyl}-N-[(1R)-2,2,2-trifluoro-1-methylethyl][1,2,4]triazolo[1,5-a]pyrimidin-7-amine and 5-chloro-6-{2,6-difluoro-4-[3-(methylamino)propoxy]phenyl}-N-[2,2,2-trifluoro-1-methylethyl][1,2,4]triazolo[1,5-a]pyrimidin-7-amine.

Specifically preferred compounds of this invention according to Formula (Ib) are the following compounds or pharmaceutically acceptable salts thereof selected from the group:

5-chloro-6-{4-[3-(dimethylamino)propoxy]-2,6-difluorophenyl}-N-[(1R)-2,2,2-trifluoro-1-methylethyl][1,2,4]triazolo[1,5-a]pyrimidin-7-amine, 5-chloro-6-{2,6-difluoro-4-[3-(methylamino)propoxy]phenyl}-N-[(1R)-2,2,2-trifluoro-1-methylethyl][1,2,4]triazolo[1,5-a]pyrimidin-7-amine, 6-[4-(3-aminopropoxy)-2,6-difluorophenyl]-5-chloro-N-[(1R)-2,2,2-trifluoro-1-methylethyl][1,2,4]triazolo[1,5-a]pyrimidin-7-amine, 5-chloro-6-{2,6-difluoro-4-[3-(4-methylpiperazin-1-yl)propoxy]phenyl}-N-[(1R)-2,2,2-trifluoro-1-methylethyl][1,2,4]triazolo[1,5-a]pyrimidin-7-amine, 5-chloro-6-{4-[3-(ethylamino)propoxy]-2,6-difluorophenyl}-N-[(1R)-2,2,2-trifluoro-1-methylethyl][1,2,4]triazolo[1,5-a]pyrimidin-7-amine, 5-chloro-6-(4-{3-[ethyl(methyl)amino]propoxy}-2,6-difluorophenyl)-N-[(1R)-2,2,2-trifluoro-1-methylethyl][1,2,4]triazolo[1,5-a]pyrimidin-7-amine, 5-chloro-6-[2,6-difluoro-4-(3-pyrrolidin-1-ylpropoxy)phenyl]-N-[(1R)-2,2,2-trifluoro-1-methylethyl][1,2,4]triazolo[1,5-a]pyrimidin-7-amine, 5-chloro-6-[2,6-difluoro-4-(3-piperidin-1-ylpropoxy)phenyl]-N-[(1R)-2,2,2-trifluoro-1-methylethyl][1,2,4]triazolo[1,5-a]pyrimidin-7-amine, 5-chloro-6-[2,6-difluoro-4-(3-morpholin-4-ylpropoxy)phenyl]-N-[(1R)-2,2,2-trifluoro-1-methylethyl][1,2,4]triazolo[1,5-a]pyrimidin-7-amine, 6-[4-(3-azetidin-1-ylpropoxy)-2,6-difluorophenyl]-5-chloro-N-[(1R)-2,2,2-trifluoro-1-methylethyl][1,2,4]triazolo[1,5-a]pyrimidin-7-amine, 5-chloro-6-{4-[3-(dimethylamino)propoxy]-2-fluorophenyl}-N-[(1R)-2,2,2-trifluoro-1-methylethyl][1,2,4]triazolo[1,5-a]pyrimidin-7-amine, 5-chloro-6-{2,6-difluoro-4-[2-(methylamino)ethoxy]phenyl}-N-[(1R)-2,2,2-trifluoro-1-methylethyl][1,2,4]triazolo[1,5-a]pyrimidin-7-amine, 5-chloro-6-{4-[4-(dimethylamino)butoxy]-2,6-difluorophenyl}-N-[(1R)-2,2,2-trifluoro-1-methylethyl][1,2,4]triazolo[1,5-a]pyrimidin-7-amine, 5-chloro-6-{4-[2-(dimethylamino)ethoxy]-2,6-difluorophenyl}-N-[(1R)-2,2,2-trifluoro-1-methylethyl][1,2,4]triazolo[1,5-a]pyrimidin-7-amine, 5-chloro-6-[2,6-difluoro-4-(2-morpholin-4-ylethoxy)phenyl]-N-[(1R)-2,2,2-trifluoro-1-methylethyl][1,2,4]triazolo[1,5-a]pyrimidin-7-amine, 5-chloro-6-(4-{[3-(dimethylamino)propyl]thio}-2,6-difluorophenyl)-N-[(1R)-2,2,2-trifluoro-1-methylethyl][1,2,4]triazolo[1,5-a]pyrimidin-7-amine, 2-[4-(5-chloro-7-{[(1R)-2,2,2-trifluoro-1-methylethyl]amino)}[1,2,4]triazolo[1,5-a]pyrimidin-6-yl)-3,5-difluorophenoxy]ethanol, 3-[4-(5-chloro-7-{[(1R)-2,2,2-trifluoro-1-methylethyl]amino)}[1,2,4]triazolo[1,5-a]pyrimidin-6-yl)-3,5-difluorophenoxy]propan-1-ol, 4-[4-(5-chloro-7-{[(1R)-2,2,2-trifluoro-1-methylethyl]amino}[1,2,4]triazolo[1,5-a]pyrimidin-6-yl)-3,5-difluorophenoxy]butan-1-ol, $N^1$-[4-(5-chloro-7-{[(1R)-2,2,2-trifluoro-1-methylethyl]amino}[1,2,4]triazolo[1,5-a]pyrimidin-6-yl)-3,5-difluorophenyl]-$N^1$,$N^3$,$N^3$-trimethylpropane-1,3-diamine, $N^1$-[4-(5-chloro-7-{[(1R)-2,2,2-trifluoro-1-methylethyl]amino}[1,2,4]triazolo[1,5-a]pyrimidin-6-yl)-3,5-difluorophenyl]-$N^3$N 3-dimethylpropane-1,3-diamine, $N^1$-[4-(5-chloro-7-{[(1R)-2,2,2-trifluoro-1-methylethyl]amino}[1,2,4]triazolo[1,5-a]pyrimidin-6-yl)-3,5-difluorophenyl]-$N^2$,$N^2$-dimethylethane-1,2-diamine, 5-bromo-6-{4-[3-(dimethylamino)propoxy]-2,6-difluorophenyl}-N-[(1R)-2,2,2-trifluoro-1-methylethyl][1,2,4]triazolo[1,5-a]pyrimidin-7-amine, 5-chloro-6-{4-[4-(dimethylamino)butyl]-2,6-difluorophenyl}-N-[(1R)-2,2,2-trifluoro-1-methylethyl][1,2,4]triazolo[1,5-a]pyrimidin-7-amine, 5-chloro-6-{3-[2-(dimethylamino)ethoxy]-2,6-difluorophenyl}-N-[(1R)-2,2,2-trifluoro-1-methylethyl][1,2,4]triazolo[1,5-a]pyrimidin-7-amine, 5-chloro-6-{3-[3-(dimethylamino)propoxy]-2,6-difluorophenyl}-N-[(1R)-2,2,2-trifluoro-1-methylethyl][1,2,4]triazolo[1,5-a]pyrimidin-7-amine, 5-chloro-6-{3-[4-(dimethylamino)butoxy]-2,6-difluorophenyl}-N-[(1R)-2,2,2-trifluoro-1-methylethyl][1,2,4]triazolo[1,5-a]pyrimidin-7-amine and 5-chloro-6-{2,6-difluoro-4-[3-(methylamino)propoxy]phenyl}-N-[(1R)-2,2,2-trifluoro-1-methylethyl][1,2,4]triazolo[1,5-a]pyrimidin-7-amine.

Specifically preferred compounds of this invention according to Formula (Ia) are the following compounds or pharmaceutically acceptable salts thereof:

5-chloro-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine, 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine, 6-[4-(3-aminopropoxy)-2,6-difluorophenyl]-5-chloro-N-[(1S)-2,2,2-trifluoro-1-methylethyl][1,2,4]triazolo[1,5-a]pyrimidin-7-amine, 5-chloro-6-{2,6-difluoro-4-[3-(4-methylpiperazin-1-yl)propoxy]phenyl}-N-[(1S)-2,2,2-trifluoro-1-methylethyl][1,2,4]triazolo[1,5-a]pyrimidin-7-amine, 5-chloro-6-{4-[3-(ethylamino)propoxy]-2,6-difluorophenyl}-N-[(1S)-2,2,2-trifluoro-1-methylethyl][1,2,4]triazolo[1,5-a]pyrimidin-7-amine, 5-chloro-6-(4-{3-[ethyl(methyl)amino]propoxy}-2,6-difluorophenyl)-N-[(1S)-2,2,2-trifluoro-1-methylethyl][1,2,4]triazolo[1,5-a]pyrimidin-7-amine, 5-chloro-6-[2,6-difluoro-4-(3-pyrrolidin-1-ylpropoxy)phenyl]-N-[(1S)-2,2,2-trifluoro-1-methylethyl][1,2,4]triazolo[1,5-a]pyrimidin-7-amine, 5-chloro-6-[2,6-difluoro-4-(3-piperidin-1-ylpropoxy)phenyl]-N-[(1S)-2,2,2-trifluoro-1-methylethyl][1,2,4]triazolo[1,5-a]pyrimidin-7-amine, 5-chloro-6-[2,6-difluoro-4-(3-morpholin-4-ylpropoxy)phenyl]-N-[(1S)-2,2,2-trifluoro-1-methylethyl][1,2,4]triazolo[1,5-a]pyrimidin-7-amine, 6-[4-(3-azetidin-1-ylpropoxy)-2,6-difluorophenyl]-5-chloro-N-[(1S)-2,2,2-trifluoro-1-methylethyl][1,2,4]triazolo[1,5-a]pyrimidin-7-amine, 5-chloro-6-{4-[3-(dimethylamino)propoxy]-2-fluorophenyl}-N-[(1S)-2,2,2-trifluoro-1-methylethyl][1,2,4]triazolo[1,5-a]pyrimidin-7-amine, 5-chloro-6-{2,6-difluoro-4-[2-(methylamino)ethoxy]phenyl}-N-[(1S)-2,2,2-trifluoro-1-methylethyl][1,2,4]triazolo[1,5-a]pyrimidin-7-amine, 5-chloro-6-{4-[4-(dimethylamino)butoxy]-2,6-difluorophenyl}-N-[(1S)-2,2,2-trifluoro-1-methylethyl][1,2,4]triazolo[1,5-a]pyrimidin-7-amine, 5-chloro-6-{4-[2-(dimethylamino)ethoxy]-2,6-difluorophenyl}-N-[(1S)-2,2,2-trifluoro-1-methylethyl][1,2,4]triazolo[1,5-a]pyrimidin-7-amine, 5-chloro-6-[2,6-difluoro-4-(2-morpholin-4-ylethoxy)phenyl]-N-[(1S)-2,2,2-trifluoro-1-methylethyl][1,2,4]triazolo[1,5-a]pyrimidin-7-amine, 5-chloro-6-(4-{[3-(dimethylamino)propyl]thio}-2,6-difluorophenyl)-N-[(1S)-2,2,2-trifluoro-1-methylethyl][1,2,4]triazolo[1,5-a]pyrimidin-7-amine, 2-[4-(5-chloro-7-{[(1S)-2,2,2-trifluoro-1-methylethyl]amino}[1,2,4]triazolo[1,5-a]pyrimidin-6-yl)-3,5-difluorophenoxy]ethanol, 3-[4-(5-chloro-7-{[(1S)-2,2,2-trifluoro-1-methylethyl]amino}[1,2,4]triazolo[1,5-a]pyrimidin-6-yl)-3,5-difluorophenoxy]propan-1-ol, 4-[4-(5-chloro-7-{[(1S)-2,2,2-trifluoro-1-methylethyl]amino}[1,2,4]triazolo[1,5-a]pyrimidin-6-yl)-3,5-difluorophenoxy]butan-1-ol, $N^1$-[4-(5-chloro-7-{[(1S)-2,2,2-trifluoro-1-methylethyl]amino}[1,2,4]triazolo[1,5-a]pyrimidin-6-yl)-3,5-difluorophenyl]-$N',N^3,N^3$-trimethylpropane-1,3-diamine, $N^1$-[4-(5-chloro-7-{[(1S)-2,2,2-trifluoro-1-methylethyl]amino}[1,2,4]triazolo[1,5-a]pyrimidin-6-yl)-3,5-difluorophenyl]-$N^3,N^3$-dimethylpropane-1,3-diamine, $N^1$-[4-(5-chloro-7-{[(1S)-2,2,2-trifluoro-1-methylethyl]amino}[1,2,4]triazolo[1,5-a]pyrimidin-6-yl)-3,5-difluorophenyl]-$N^2, N^2$-dimethylethane-1,2-diamine, 5-bromo-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine, 5-chloro-6-{4-[4-(dimethylamino)butyl]-2,6-difluorophenyl}-N-[(1S)-2,2,2-trifluoro-1-methylethyl][1,2,4]triazolo[1,5-a]pyrimidin-7-amine, 5-chloro-6-{3-[2-(dimethylamino)ethoxy]-2,6-difluorophenyl}-N-[(1S)-2,2,2-trifluoro-1-methylethyl][1,2,4]triazolo[1,5-a]pyrimidin-7-amine, 5-chloro-6-{3-[3-(dimethylamino)propoxy]-2,6-difluorophenyl}-N-[(1S)-2,2,2-trifluoro-1-methylethyl][1,2,4]triazolo[1,5-a]pyrimidin-7-amine and 5-chloro-6-{3-[4-(dimethylamino)butoxy]-2,6-difluorophenyl}-N-[(1S)-2,2,2-trifluoro-1-methylethyl][1,2,4]triazolo[1,5-a]pyrimidin-7-amine.

Most particularly preferred compounds of this invention according to Formula (Ia) are the following compounds or pharmaceutically acceptable salts thereof:

5-chloro-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine and 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine.

A specifically preferred compound of this invention according to Formula (Ib) is the following compound or pharmaceutically acceptable salts thereof:

5-chloro-6-{2,6-difluoro-4-[3-(methylamino)propoxy]phenyl}-N-[(1R)-2,2,2-trifluoro-1-methylethyl][1,2,4]triazolo[1,5-a]pyrimidin-7-amine.

More specifically preferred compounds of the invention include:

5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine hydrogen chloride, 5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate salt, 5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate salt, 5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate salt dihydrate and 5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate salt dihydrate.

Most specifically preferred compounds of the invention is

5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate salt and 5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate salt dihydrate Further preferred compounds of this invention according to Formula (I) are the following compounds or pharmaceutically acceptable salts thereof:

5-chloro-6-{4-[3-(dimethylamino)propoxy]-2,6-difluorophenyl}-N-[2,2,2-trifluoro-1-methylethyl][1,2,4]triazolo[1,5-a]pyrimidin-7-amine, 5-chloro-6-{2,6-difluoro-4-[3-(methylamino)propoxy]phenyl}-N-[2,2,2-trifluoro-1-methylethyl][1,2,4]triazolo[1,5-a]pyrimidin-7-amine, 6-[4-(3-aminopropoxy)-2,6-difluorophenyl]-5-chloro-N-[2,2,2-trifluoro-1-methylethyl][1,2,4]triazolo[1,5-a]pyrimidin-7-amine, 5-chloro-6-{2,6-difluoro-4-[3-(4-methylpiperazin-1-yl)propoxy]phenyl}-N-[2,2,2-trifluoro-1-methylethyl][1,2,4]triazolo[1,5-a]pyrimidin-7-amine, 5-chloro-6-{4-[3-(ethylamino)propoxy]-2,6-difluorophenyl}-N-[2,2,2-trifluoro-1-methylethyl][1,2,4]triazolo[1,5-a]pyrimidin-7-amine, 5-chloro-6-(4-{3-[ethyl(methyl)amino]propoxy}-2,6-difluorophenyl)-N-[2,2,2-trifluoro-1-methylethyl][1,2,4]triazolo[1,5-a]pyrimidin-7-amine, 5-chloro-6-[2,6-difluoro-4-(3-pyrrolidin-1-ylpropoxy)phenyl]-N-[2,2,2-trifluoro-1-methylethyl][1,2,4]triazolo[1,5-a]pyrimidin-7-amine, 5-chloro-6-[2,6-difluoro-4-(3-piperidin-1-ylpropoxy)phenyl]-N-[2,2,2-trifluoro-1-methylethyl][1,2,4]triazolo[1,5-a]pyrimidin-7-amine, 5-chloro-6-[2,6-difluoro-4-(3-morpholin-4-ylpropoxy)phenyl]-N-[2,2,2-trifluoro-1-methylethyl][1,2,4]triazolo[1,5-a]pyrimidin-7-amine, 6-[4-(3-azetidin-1-ylpropoxy)-2,6-difluorophenyl]-5-chloro-N-[2,2,2-trifluoro-1-methylethyl][1,2,4]triazolo[1,5-a]pyrimidin-7-amine, 5-chloro-6-{4-[3-(dimethylamino)propoxy]-2-fluorophenyl}-N-[2,2,2-trifluoro-1-methylethyl][1,2,4]triazolo[1,5-a]pyrimidin-7-amine, 5-chloro-6-{2,6-difluoro-4-[2-(methylamino)ethoxy]phenyl}-N-[2,2,2-trifluoro-1-methylethyl][1,2,4]triazolo[1,5-a]pyrimidin-7-amine, 5-chloro-6-{4-[4-(dimethylamino)butoxy]-2,6-difluorophenyl}-N-[2,2,2-trifluoro-1-methylethyl][1,2,4]triazolo[1,5-a]pyrimidin-7-amine, 5-chloro-6-{4-[2-(dimethylamino)ethoxy]-2,6-difluorophenyl}-N-[2,2,2-trifluoro-1-methylethyl][1,2,4]triazolo[1,5-a]pyrimidin-7-amine, 5-chloro-6-[2,6-difluoro-4-(2-morpholin-4-ylethoxy)phenyl]-N-[2,2,2-trifluoro-1-methylethyl][1,2,4]triazolo[1,5-a]pyrimidin-7-amine, 5-chloro-6-(4-{[3-(dimethylamino)propyl]thio}-2,6-difluorophenyl)-N-[2,2,2-trifluoro-1-methylethyl][1,2,4]triazolo[1,5-a]pyrimidin-7-amine, 2-[4-(5-chloro-7-{[2,2,2-trifluoro-1-methylethyl]amino}[1,2,4]triazolo[1,5-a]pyrimidin-6-yl)-3,5-difluorophenoxy]ethanol, 3-[4-(5-chloro-7-{[2,2,2-trifluoro-1-methylethyl]amino}[1,2,4]triazolo[1,5-a]pyrimidin-6-yl)-3,5-difluorophenoxy]propan-1-ol, 4-[4-(5-chloro-7-{[2,2,2-trifluoro-1-methylethyl]amino}[1,2,4]triazolo[1,5-a]pyrimidin-6-yl)-3,5-difluorophenoxy]butan-1-ol, $N^1$-[4-(5-chloro-7-{[2,2,2-trifluoro-1-methylethyl]amino}[1,2,4]triazolo[1,5-a]pyrimidin-6-yl)-3,5-difluorophenyl]-$N'$,$N^3$,$N^3$-trimethylpropane-1,3-diamine, $N^1$-[4-(5-chloro-7-{[2,2,2-trifluoro-1-methylethyl]amino}[1,2,4]triazolo[1,5-a]pyrimidin-6-yl)-3,5-difluorophenyl]-$N^3$, $N^3$-dimethylpropane-1,3-diamine, $N^1$-[4-(5-chloro-7-{[2,2,2-trifluoro-1-methylethyl]amino}[1,2,4]triazolo[1,5-a]pyrimidin-6-yl)-3,5-difluorophenyl]-$N^2$,$N^2$-dimethylethane-1,2-diamine, 5-bromo-6-{4-[3-(dimethylamino)propoxy]-2,6-difluorophenyl}-N-[2,2,2-trifluoro-1-methylethyl][1,2,4]triazolo[1,5-a]pyrimidin-7-amine, 5-chloro-6-{4-[4-(dimethylamino)butyl]-2,6-difluorophenyl}-N-[2,2,2-trifluoro-1-methylethyl][1,2,4]triazolo[1,5-a]pyrimidin-7-amine, 5-chloro-6-[3-[2-(dimethylamino)ethoxy]-2,6-difluorophenyl]-N-[2,2,2-trifluoro-1-methylethyl][1,2,4]triazolo[1,5-a]pyrimidin-7-amine, 5-chloro-6-{3-[3-(dimethylamino)propoxy]-2,6-difluorophenyl}-N-[2,2,2-trifluoro-1-methylethyl][1,2,4]triazolo[1,5-a]pyrimidin-7-amine, and 5-chloro-6-{3-[4-(dimethylamino)butoxy]-2,6-difluorophenyl}-N-[2,2,2-trifluoro-1-methylethyl][1,2,4]triazolo[1,5-a]pyrimidin-7-amine.

DETAILED DESCRIPTION OF THE INVENTION

The compounds of this invention may be prepared from: (a) commercially available starting materials; (b) known starting materials which may be prepared as described in literature procedures or (c) new intermediates described in the schemes and experimental procedures herein.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps. Appropriate consideration must be made as to the protection of reactive functional groups to prevent undesired side reactions. Substituents on the starting materials may be incompatible with some of the reaction conditions. Such restrictions to the substituents which are compatible with the reaction conditions will be apparent to one skilled in the art. Reactions are run under inert atmospheres where appropriate.

The compounds of this invention encompassed by Formula (I) where Y is O, S, or $NR^4$ and $R^1$ is

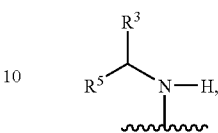

may be prepared by a process shown in Scheme I, which comprises treating a compound of the Formula (II) (U.S. Pat. Nos. 5,948,783, 5,986,135, 6,117,876, and 6,297,251) in which $R^1$, $R^2$, $R^3$, $R^5$, $L^1$, $L^2$, and X are as hereinbefore defined, and $L^3$ represents a leaving group, which is a removable group, in particular a fluorine atom, with a compound of the formula HY—$(CH_2)_n$Q in which Q and Y are as hereinbefore defined, in the presence of a strong base including alkali metal hydroxide, alkali metal carbonate and alkali metal hydride, e.g., sodium hydride, in the presence or absence of a solvent. Suitable solvents include aprotic solvents, such as dimethylsulfoxide, dimethylformamide, and the like. The reaction is suitably carried out at a temperature in the range from about 0° C. to about 100° C.

Scheme 1:

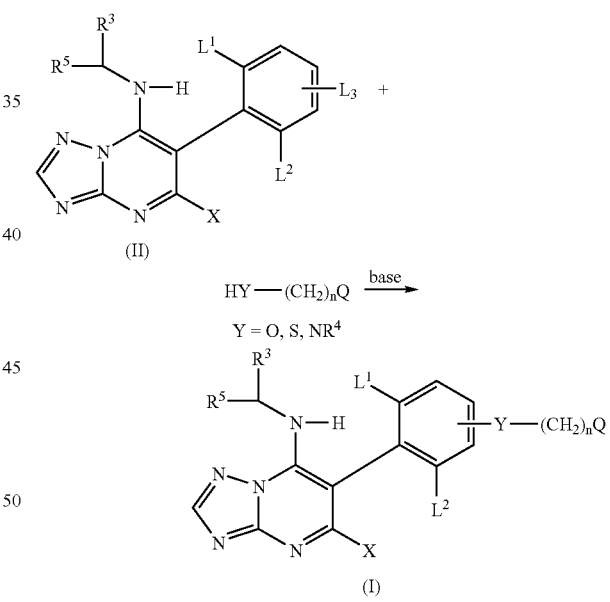

Compounds of Formula (I) where $R^1$ is

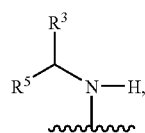

Y is $CH_2$ can be prepared by a process described in Scheme II below wherein $R^1$, $R^2$, $R^3$, $R^5$, $R^6$, $R^7$, $L^1$, $L^2$, X and n are as defined above.

Scheme II:

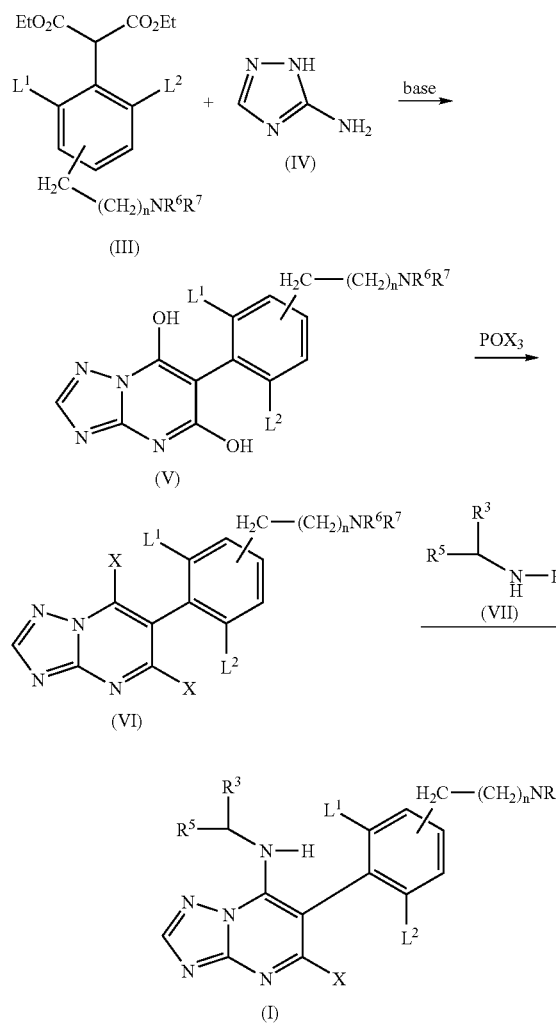

Scheme III:

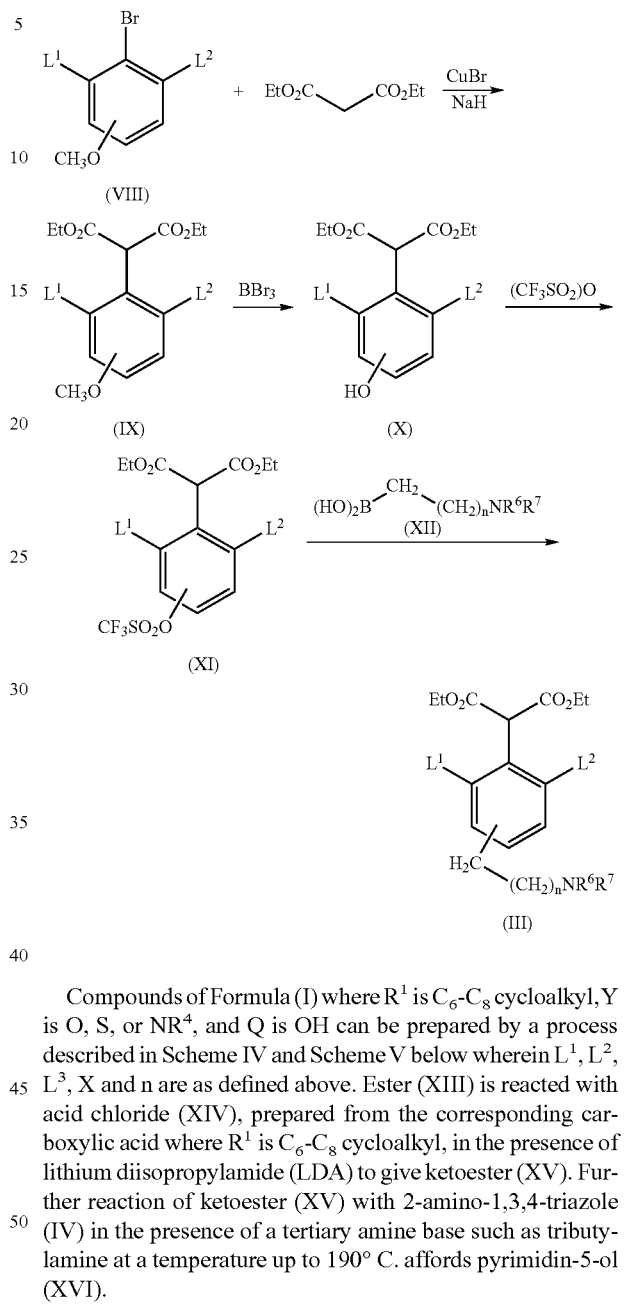

As described in Scheme II, treating diester (III) with 2-amino-1,3,4-triazole (IV) in the presence of a tertiary amine base such as tributylamine, at a temperature up to 190° C. provides compound (V). Halogenation of compound (V) with halogenating agents $POX_3$, $PX_3$, or $PX_5$, such as phosphorous oxychloride or phosphorous oxybromide, gives 5,7-dihalo compound (VI) where X is hereinbefore defined. Displacement of the 5-bromo or 5-chloro of 5,7-dihalo compound (VI) with an amine (VII) in a suitable aprotic solvent, such as dimethylsulfoxide or dimethylformamide, and the like in the presence of a base, e.g., N,N-diisopropylethylamine, provides compounds of Formula (I).

Diester (III) can be prepared by a palladium-catalyzed process in which trifluoromethanesulfonate (XI) is coupled with aminoalkyl boronic acid (XII). Trifluorosulfonate (XI) can be prepared by coupling bromide (VIII) with diethyl malonate (U.S. Pat. No. 5,981,534), to provide diester (IX) followed by demethylation in the presence of boron tribromide to give phenol (X). Further reaction of phenol (X) with trifluoromethanesulfonic anhydride affords trifluoromethanesulfonate (XI) as shown in Scheme III.

Compounds of Formula (I) where $R^1$ is $C_6$-$C_8$ cycloalkyl, Y is O, S, or $NR^4$, and Q is OH can be prepared by a process described in Scheme IV and Scheme V below wherein $L^1$, $L^2$, $L^3$, X and n are as defined above. Ester (XIII) is reacted with acid chloride (XIV), prepared from the corresponding carboxylic acid where $R^1$ is $C_6$-$C_8$ cycloalkyl, in the presence of lithium diisopropylamide (LDA) to give ketoester (XV). Further reaction of ketoester (XV) with 2-amino-1,3,4-triazole (IV) in the presence of a tertiary amine base such as tributylamine at a temperature up to 190° C. affords pyrimidin-5-ol (XVI).

Scheme IV:

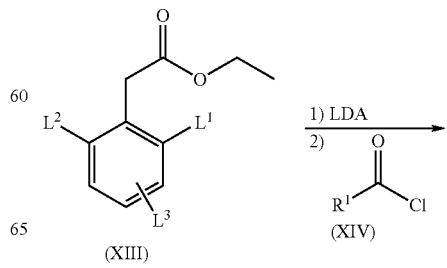

-continued

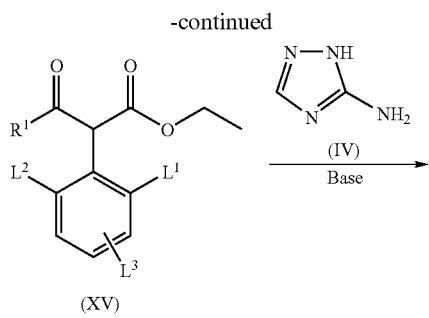

(XV)

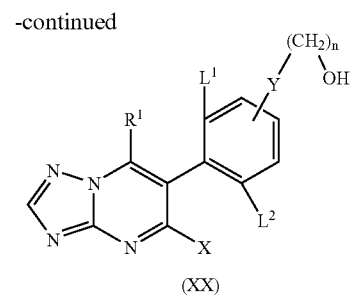

(XX)

With reference to Scheme VI, pyrimidin-5-ol (XVI), where $R^1$ is $C_6$-$C_8$ cycloalkyl, is reacted with compound (XXI), where Y is O, S or —$NR^4$, and $R^6$ and $R^7$ are other than H, in the presence of a strong base which includes an alkali metal hydroxide, alkali metal carbonate and alkali metal hydride, e.g., sodium hydride in the presence of an aprotic solvent which includes: dimethylformamide, dimethyl sulfoxide, and the like to give amine (XXII). Reaction of amine (XXII) with halogenating agents $POX_3$, $PX_3$, or $PX_5$, such as phosphorous oxychloride or phosphorous oxybromide in the presence of N,N-diethylaniline affords compound (XXIII) where X is hereinbefore defined, $R^1$ is $C_6$-$C_8$ cycloalkyl, and $R^6$ and $R^7$ are other than H.

As shown in Scheme V, pyrimidin-5-ol (XVI) is reacted with compound (XVII) in the presence of a strong base which includes an alkali metal hydroxide, alkali metal carbonate and alkali metal hydride, e.g., sodium hydride in an aprotic solvent which includes dimethylsulfoxide, dimethylformamide, and the like to give ether (XVIII). Reaction of ether (XVIII) with halogenating agents $POX_3$, $PX_3$, or $PX_5$, such as phosphorous oxychloride or phosphorous oxybromide in the presence of N,N-diethylaniline affords compound (XIX) where X is hereinbefore defined, which is further reacted with 2,3-dichloro-5,6-dicyano-1,4-benzoquinone (DDQ) to afford alcohol (XX) where $R^1$ is $C_6$-$C_8$ cycloalkyl.

Scheme VI:

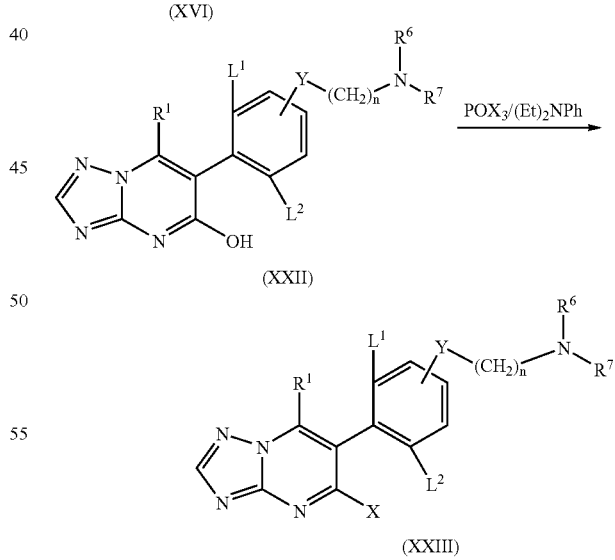

Scheme V:

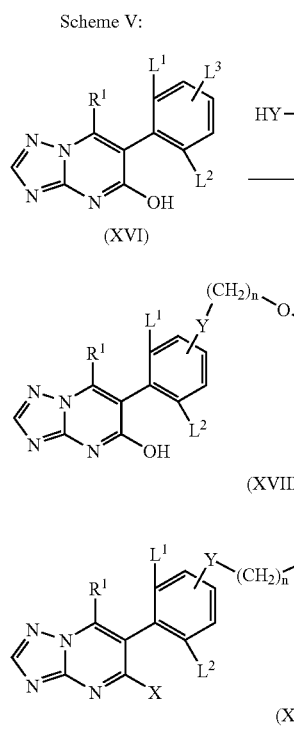

As shown in Scheme VII, pyrimidin-5-ol (XVI) where $R^1$ is $C_6$-$C_8$ cycloalkyl is reacted with amino compound (XXIV), where Y is O, S or —$NR^4$, and $R^7$ is H, in the presence of a strong base which includes an alkali metal hydroxide, alkali metal carbonate and alkali metal hydride, e.g., sodium hydride in the presence of an aprotic solvent which includes:

dimethylformamide, dimethyl sulfoxide, and the like to give amine (XXV). Reaction of amine (XXV) with di-tert-butyl dicarbonate affords tert-butoxy carbonyl (t-BOC) blocked amine (XXVI). Reaction of (t-BOC) blocked amine (XXVI) with halogenating agents POX$_3$, PX$_3$, or PX$_5$, such as phosphorous oxychloride or phosphorous oxybromide in the presence of N,N-diethylaniline affords compound (XXVII) where X is hereinbefore defined. Compound (XXVII) is then deblocked with trifluoroacetic acid (TFA) to afford amine (XXVIII).

7-amine, is neutralized with aqueous alkali metal hydroxide or aqueous alkali metal carbonate, and further reacted with a suitable pharmaceutically acceptable salt forming acid described hereinabove in a suitable solvent. Suitable solvents which may be used include: water, methanol, ethanol, isopropanol or combination thereof and the like. A preferred solvent is water.

Preferably, pharmaceutically acceptable salts may form by heating compounds of Formula (I) in a suitable solvent, at Scheme VII:

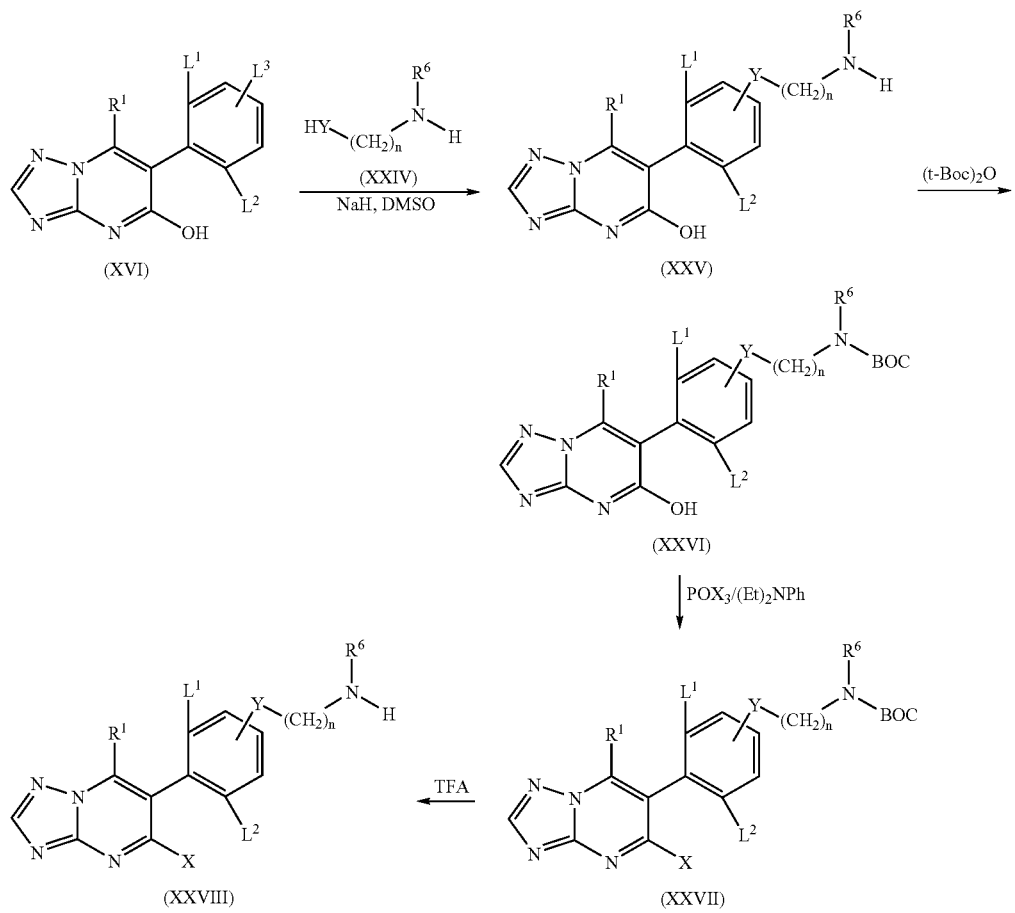

It is understood that this invention encompasses all crystalline and hydrated forms of compounds of Formula (I) and their pharmaceutically acceptable salts. The pharmaceutically acceptable salts of the compounds of this invention are those derived from such organic and inorganic pharmaceutically acceptable salt forming acids as: lactic, citric, acetic, tartaric, fumaric, succinic, maleic, malonic, hydrochloric, hydrobromic, phosphoric, nitric, sulfuric, methanesulfonic, benzenesulfonic, L-aspartic, R or S-mandelic, palmitic and similarly known acceptable acids. A further salt is the trifluoroacetic acid salt (TFA). In particular the hydrochloride, fumarate and succinate salts are preferred.

As a representative example of pharmaceutically acceptable salt formation, the hydrochloride salt of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidinabout 30-100° C., preferably at about 65-75° C., until a clear solution forms. Upon cooling the compound may be collected and dried.

Using the conditions described hereinabove, 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate salt and 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate salt are produced. In particular dihydrates may be formed by further contact with an atmosphere of water at about 80-100% relative humidity for about 24 hours at room temperature.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

Based on the results of standard pharmacological test procedures described herein, the compounds of this invention are useful as agents for treating, inhibiting or controlling the growth of cancerous tumor cells and associated diseases in a mammal in need thereof. The compounds of the invention are useful as agents for treating, inhibiting or controlling the growth of cancerous tumor cells and associated diseases in a mammal in need thereof by interacting with tubulin and microtubules and promoting microtubule polymerization. The compounds of the invention are also useful for the treatment or prevention of cancerous tumors that express multiple drug resistance (MDR) or are resistant because of MDR.

In particular, when contacting a tubulin containing system with an effective amount of a compound of Formula (I) results in the promotion of microtubule polymerization and further stabilizes microtubules and by promoting microtubule polymerization and stabilizing microtubules said compounds of Formula (I) are useful as agents for treating, inhibiting or controlling the growth of cancerous tumor cells and associated diseases. The tubulin containing system may be in a tumor cell, thereby inhibiting neoplastic disease by administering an effective amount of a compound described in the present invention. Mammals may be treated and in particular, humans. Further, said tubulin containing system may be in a patient. In the case of cancer treatment, it is believed that many neoplasias such as leukemia, lung cancer, colon cancer, thyroid cancer, ovarian cancer, renal cancer, prostate cancer and breast cancers may be treated by effectively administering effective amounts of the compounds of formulae (I). Additionally, compounds of Formula (I) are useful for the treatment or prevention of cancerous tumors that express multiple drug resistance (MDR) or are resistant because of MDR. As used herein, cancer refers to all types of cancers, or neoplasms or benign or malignant tumors. Preferred cancers for treatment using methods provided herein include carcinoma, sarcoma, lymphoma, or leukemia. By carcinoma is meant a benign or malignant epithelial tumor and includes, but is not limited to, breast carcinoma, prostate carcinoma, non-small lung carcinoma, colon carcinoma, melanoma carcinoma, ovarian carcinoma, or renal carcinoma. A preferred host is a human.

The effective dosage of active ingredient employed may vary depending on the particular compound employed, the mode of administration and severity of the condition being treated. However, in general satisfactory results are obtained when the compounds of the invention are administered in amounts ranging from about 0.10 to about 100 mg/kg of body weight per day. A preferred regimen for optimum results would be from about 1 mg to about 20 mg/kg of body weight per day and such dosage units are employed that a total of from about 70 mg to about 1400 mg of the active compound for a subject of about 70 kg of body weight are administered in a 24 hour period.

The dosage regimen for treating mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes.

The active compounds of the invention may preferably be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 10 and 1000 mg of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agnet such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

Intravenous administration is a preferred manner of administration of compounds of the invention. For intravenous administration examples of non-limiting suitable carriers include physiological saline, bacteriostatic water, Cremophor ELTM (BASF, Parsippany, N.J.) or phosphate buffered saline (PBS). The composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

As used in accordance with this invention, the term providing an effective amount of a compound means either directly administering such compound, or administering a prodrug, derivative, or analog which will form an effective amount of the compound within the body.

In addition to the above utilities some of the compounds of this invention are useful for the preparation of other compounds of this invention.

Examples of this invention are evaluated in several standard pharmacological test procedures that showed that the compounds of this invention possess significant activity as promoters of microtubule polymerization and are antineoplastic agents. Based on the activity shown in the standard pharmacological test procedures, the compounds of this invention are therefore useful as anticancer agents. Associated cancers are selected from the group consisting of breast, colon, lung, prostate, melanoma, epidermal, leukemia, kidney, bladder, mouth, larynx, esophagus, stomach, ovary, pancreas, liver, skin and brain. In particular, the compounds of this invention possess an effect similar to Paclitaxel. The test procedures used and results obtained are shown below.

Standard Pharmacological Test Procedures

Materials and Methods

1. Cell Culture Media and Reagents

Medium is RPMI-1640 with L-glutamine, supplemented with 10% heat-inactivated fetal calf serum, 100 units/ml penicillin, and 100 μg/ml streptomycin (Gibco, Grand Island, N.Y.). Microtubule-associated protein (MAP)-rich tubulin, containing about 70% tubulin and 30% MAPs (#ML113), and highly purified tubulin (>99% pure, #TL238), both from bovine brain, are obtained from Cytoskeleton, Inc., Denver, Colo. PEM buffer (80 mM piperazine-N,N'-bis[2-ethanesulfonic acid], pH 6.9, 1 mM ethylene glycol-bis(β-aminoethyl ether)-N,N,N',N'-tetraacetic acid, 1 mM magnesium chloride) and guanosine 5'-triphosphate (GTP) are also obtained from Cytoskeleton. [3H]paclitaxel, specific activity 14.7 Ci/mmol, is purchased from Moravek Biochemicals (Brea, Calif.). [$^3$H]vinblastine, specific activity 9.60 Ci/mmol and MicroSpin G-50 columns are obtained from Amersham Biosciences (Piscataway, N.J.). [$^3$H]colchicine, specific activity 76.5 Ci/mmol, is obtained from New England Nuclear (Boston, Mass.). Other reagents are obtained from Sigma (St. Louis, Mo.).

2. Cell Lines

Human cancer cell lines, unless otherwise noted, are obtained from the American Type Culture Collection (Rockville, Md.). The following drug-sensitive parental cell lines, and their derived drug-resistant counterparts, are obtained from the originators as listed: (a) S1 (parental line from a subclone of human colon carcinoma line LS174T) and derived S1-M1-3.2 (herein called S1-M1) which expresses the MXR drug transporter protein, are provided by Dr. L. Greenberger, Wyeth Research (Rabindran, S. K., He, H., Singh, M., Brown, E., Collins, K. I., Annable, T., and Greenberger, L. M. Reversal of a novel multidrug resistance mechanism in human colon carcinoma cells by fumitremorgin C. Cancer Res., 58:5850-5858,1998); (b) parental HL-60 human promyelocytic leukemia line and derived HL-60/ADR, which expresses the MRP1 drug transporter protein, are provided by Dr. M. Center, University of Kansas (McGrath, T., and Center, M. S. Adriamycin resistance in HL60 cells in the absence of detectable P-glycoprotein. Biochem. Biophys. Res. Commun., 145:1171-1176,1987), via Dr. L. Greenberger, Wyeth Research; and (c) parental KB-3-1 (herein called KB, cloned from a human epidermoid carcinoma) and the derived lines KB-8-5 and KB-V1, which express moderate and very high levels of the MDR1 (P-glycoprotein) drug transporter protein, respectively, are provided by Dr. M. Gottesman, National Cancer Institute (Shen, D. W., Cardarelli, C., Hwang, J., Cornwell, M., Richert, N., Ishii, S., Pastan, I., and Gottesman, M. M. Multiple drug-resistant human KB carcinoma cells independently selected for high-level resistance to colchicine, adriamycin, or vinblastine show changes in expression of specific proteins. J. Biol. Chem., 261: 7762-7770,1986) via Dr. L. Greenberger, Wyeth Research.

3. Cytotoxicity Standard Pharmacological Test Procedure

The assay, which is sold in kit form by Promega (Madison, Wis.; CellTiter 96 AQueous Non-Radioactive Cell Proliferation Assay), is based on the conversion by viable cells, but not by dead cells, of the tetrazolium salt, MTS (3-(4,5-dimethylthiazol-2-yl)-5-(3-carboxymethoxyphenyl)-2-(4-sulphophenyl)-2H-tetrazolium, inner salt), into a water-soluble colored formazan which is detected by spectrophotometry. Compounds are tested at nine concentrations, in order to determine $IC_{50}$ values. For the test procedure, cells are harvested by trypsinization (or, in the case of non-adherent cells, by simple resuspension), washed, counted and distributed to wells of 96-well flat-bottom microtiter plates at 1000 cells per well in 200 μL of medium. In addition, one row of wells on a separate plate received cells as above ("time 0" plate). All plates are incubated at 37° in humidified 5% $CO_2$ in air for about 24 hr.

On day 2, compounds for test are diluted and added to wells. Compounds are dissolved in DMSO at 10 mg/mL. For each compound, nine serial 2-fold dilutions are prepared in DMSO. Ten μL of each dilution in DMSO is transferred to 100 μL of medium, mixed well, and then 5 μL of this dilution is transferred in quadruplicate to wells containing cells. The final high concentration of each compound is typically 5 μM. Plates are returned to the incubator for three days. At the time of drug addition to the experimental plates, the MTS assay is run on the "time 0" plate. This produced the "time 0 MTS value" which is related to the number of viable cells per well at the time of drug addition.

After three days of culture with test compounds (day 5 overall), the MTS assay is done on all wells of the experimental plates. The absorbance values of the quadruplicate sample wells are averaged and divided by the average of the "time 0" values. The average of control wells without drug, divided by the average "time 0" value, gave the maximal relative increase in MTS color yield due to cell growth during the final three days of culture. The average of control wells with high drug concentration, divided by the "time 0" value, gave the minimal relative color yield for cells that are completely killed. The nine values for each compound are plotted against concentration, and the concentration that produced a relative color yield half way between the maximum and minimum is taken as the $IC_{50}$ value. The most potent compounds had the lowest $IC_{50}$ values.

4. Tubulin Polymerization Standard Pharmacological Test Procedure

Two variations of this procedure are done, one using MAP-rich tubulin and one using pure tubulin.

MAP-rich tubulin is dissolved in ice-cold PEM buffer containing 1 mM GTP (GPEM buffer) at a concentration of 1.3 mg/mL. The solution is centrifuged at top speed in an Eppendorf model 5415C microcentrifuge (Brinkmann Instruments, Westbury, N.Y.) for 10 min at 40 immediately before use. The tubulin solution is added to wells of a ½-area 96-well plate (Costar No. 3696, Corning, Inc., Corning, N.Y.) already containing the compounds of interest. Each compound is tested in duplicate at a final concentration of 0.3 µM in a volume of 110 µL per well. The final DMSO concentration in all wells is 0.3%. Control reactions, which received compound solvent only, are done in quadruplicate. The plate is put in a Spectra-Max Plus plate reader (Molecular Devices Corp. Sunnyvale, Calif.) thermostated at 24° and the absorbance of each well at 340 nm, a measure of the appearance of turbidity due to tubulin polymer formation, is determined every minute for 60 minutes. The absorbance at time 0 for each well is subtracted from each of the subsequent absorbance readings for that well, and then the duplicates are averaged.

The procedure with pure tubulin is similar except for the following changes. Pure tubulin is dissolved in cold PEM buffer containing 10% glycerol and no added GTP at a concentration of 1.5 to 1.8 mg/mL (15 to 18 µM). The supernatant after centrifugation is dispensed to a 96-well plate already containing compounds. Each compound is tested in duplicate at six serial 3-fold dilutions starting at 24.3 µM. The plate reader is thermostated at 35°.

5. Competitive Binding Standard Pharmacological Test Procedure

The binding of examples of this invention to highly purified tubulin is studied by competitive inhibition methods. The αβ-tubulin heterodimer contains binding sites for the three major classes of microtubule-active pharmacological agents: taxanes, vinca/peptide-site agents, and colchicine-site agents. To study possible competition at the vinca/peptide and colchicine sites, incubations are done under conditions which do not favor polymerization because vinblastine and colchicine bind preferentially to unpolymerized heterodimer. To study possible competition at the taxane site, on the other hand, polymerized tubulin (microtubules) is used because paclitaxel binds preferentially to microtubules.

Highly purified tubulin is dissolved in PEM buffer without GTP and used at a final concentration of 1.0 to 1.3 mg/ml (10 to 13 µM). To the tubulin solution is added various concentrations of examples of this invention up to a highest concentration of 100 µM, and [$^3$H]vinblastine or [$^3$H]colchicine at final concentrations of 100 nM or 50 nM, respectively. These solutions are incubated at 24° for 1 hr and then applied to MicroSpin G-50 columns which are centrifuged for 2 min at 3000 rpm in an Eppendorf 5415C microfuge. An aliquot of each column effluent (containing tubulin and bound radioligand) is mixed with scintillation fluid and counted in a liquid scintillation spectrometer. Controls included samples without competitor, and samples with unlabeled vincristine, colchicine, or paclitaxel. The ability of the competitor to inhibit the binding of the radioligand is expressed as a percentage of control binding in the absence of any competitor.

For competition with [$^3$H]paclitaxel, highly purified tubulin is dissolved in PEM buffer containing 0.75 M glutamate and 25 µM dideoxy-GTP; final protein concentration is 0.25 to 0.35 mg/mL (2.5 to 3.5 µM). These conditions foster the rapid formation of short, stable microtubule polymers (Hamel, E., del Campo, A. A., and Lin, C. M. Stability of tubulin polymers formed with dideoxyguanosine nucleotides in the presence and absence of microtubule-associated proteins. J. Biol. Chem., 259: 2501-2508, 1984). This solution is incubated for 30 min at 37° to allow microtubules to form. Then [$^3$H]paclitaxel (final concentration of 2.1 µM, 1.2 Ci/mmol) and competitor (final concentration of 20 µM, except 5 µM for unlabeled paclitaxel) are added to aliquots of the polymerized tubulin solution and incubation at 37° is continued for another 30 min. Controls included samples without competitor, and samples with unlabeled vincristine, colchicine, or paclitaxel. The reactions are then centrifuged at top speed in an Eppendorf 5415C microfuge for 20 min at room temperature in order to pellet the microtubule protein. Triplicate aliquots of each supernatant are mixed with scintillation fluid and counted in a liquid scintillation spectrometer. From the amount of radioactivity in the supernatants and the measured total starting radioactivity, the amount of [$^3$H] paclitaxel bound to pelleted microtubule protein is calculated. The ability of each competitor to inhibit radioligand binding to pelleted protein is expressed as a percent of controls without any competitor.

6. Cell Cycle Analysis Standard Pharmacological Test Procedure

HeLa cells are harvested by trypsinization, washed, counted and distributed to wells of 12-well plates at 125,000 cells per well in 2 mL medium. Cells are cultured overnight. Compound dilutions are made in DMSO and 10 µL aliquots are added to each well to give the desired final concentrations. Cells are continued in culture for 18 hr after compound addition, then cells in each well are harvested (taking care to recover both adherent and non-adherent cells) and processed using the CycleTEST PLUS kit (Becton Dickinson Immunocytometry Systems, San Jose, Calif.). Flow cytometry is done with a FACSort instrument (Becton Dickinson).

7. Antitumor Activity in Athymic Mice Bearing Human Tumor Xenografts Standard Pharmacological Test Procedure The ability of compounds of this invention to inhibit tumor growth in animals is studied in the athymic mouse xenograft standard pharmacological test. Female nu/nu mice in an outbred albino background are obtained from Charles River Laboratories (Wilmington, Mass.). Animals are injected subcutaneously on the flank with the desired tumor cell suspension. Several days later, mice with tumors of approximately 150 mm$^3$ are selected from those injected (staged) and randomly distributed into groups of 5-10. The day of staging is called day 0. Compounds of the invention, usually formulated in saline (exceptions are noted in tables), are administered to animals by intravenous injection or oral gavage on various schedules starting on day 0 or 1, as noted in the tables. The control group in each experiment is dosed with vehicle on the same schedule. Tumor size is measured every 3-7 days with calipers in two orthogonal dimensions, and tumor volume is calculated from the formula volume=[(length×width$^2$)/2].

Tumor/Control (T/C) is obtained by dividing the mean tumor volume of the treated group by the mean tumor volume of the control group on each measurement day. A treatment dose is defined as active if it produced a statistically significant T/C of 0.50 or less. A p value$\leq$0.05, determined by one-side Student's t-test, is required for statistical significance. A treatment dose is defined as toxic if more than 10% of the animals died from a compound-related toxicity.

Results

1. Cytotoxicity Standard Pharmacological Test Procedure
   1.1. With COLO 205 Cells
   COLO 205 is a human colon carcinoma cell line that is used for comparative testing of the examples of this invention and several reference compounds. This line is sensitive to paclitaxel and vincristine. As shown in Table 1, for example, example 32 has an $IC_{50}$ value of 6.6 nM.

TABLE 1

Activity of Representative Examples of the Invention and Reference Compounds in the MTS Cytotoxicity Standard Pharmacological Test Procedure with COLO 205 Cells[1]

| Example or Reference Compound | Salt | $IC_{50}$ (nM) | SD | n |
|---|---|---|---|---|
| 1 | | 41 | 13 | 8 |
| 1a | HCl Salt | 56 | 9 | 11 |
| 2 | | 32 | 10 | 23 |
| 2a | HCl Salt | 31 | 10 | 11 |
| 2c | Succinate Salt | 38 | — | 1 |
| 3 | | 25 | 9 | 7 |
| 3a | HCl Salt | 29 | 7 | 3 |
| 4a | HCl Salt | 53 | 16 | 10 |
| 5 | | 452 | 71 | 3 |
| 6 | | 155 | 17 | 3 |
| 7 | | 29 | 17 | 3 |
| 8 | | 48 | 6 | 2 |
| 9 | | 44 | 13 | 3 |
| 10 | | 113 | 12 | 2 |
| 11 | | 89 | 34 | 3 |
| 11a | HCl Salt | 51 | 30 | 3 |
| 12 | | 326 | 116 | 3 |
| 13 | | 262 | 18 | 2 |
| 14 | | 881 | 186 | 2 |
| 15 | | 276 | 53 | 2 |
| 16 | | 581 | 157 | 2 |
| 17 | | 245 | 118 | 4 |
| 18 | | 192 | 72 | 3 |
| 19 | | 422 | 175 | 2 |
| 20 | | 67 | 12 | 5 |
| 21 | | 151 | 19 | 3 |
| 22 | | 1671 | 34 | 2 |
| 23 | | 719 | 185 | 2 |
| 24 | | 1728 | 138 | 2 |
| 25 | | 96 | 21 | 6 |
| 26 | | 665 | 103 | 2 |
| 27 | | 1568 | 81 | 2 |
| 28 | | 785 | 64 | 2 |
| 29 | | 433 | 74 | 2 |
| 30 | | 30 | 5 | 5 |
| 31 | | 19 | 8 | 6 |
| 32 | TFA Salt | 6.6 | 2 | 5 |
| 33 | | 126 | 1 | 2 |
| Paclitaxel | | 3.3 | 1 | 20 |
| Vincristine | | 2.6 | 0.5 | 7 |

[1]$IC_{50}$ values and standard deviations are from the indicated number of independent experiments 1.2. With KB, KB-8-5, and KB-V1 Cells
The KB lines express different amounts of the P-glycoprotein (MDR1) membrane pump which produces resistance to the action of many cytotoxic compounds, including paclitaxel and vincristine. The parental KB line expresses no P-glycoprotein, KB-8-5 expresses moderate levels of the protein, and KB-V1 expresses very high levels. The ability of P-glycoprotein to recognize and export a potential cytotoxic agent can be inferred from the change in $IC_{50}$ values on these lines (Loganzo, F., Discafani, C. M., Annable, T., Beyer, C., Musto, S., Hari, M., Tan, X., Hardy, C., Hernandez, R., Baxter, M., Singanallore, T., Khafizova, G., Poruchynsky, M. S., Fojo, T., Nieman, J. A., Ayral-Kaloustian, S., Zask, A., Andersen, R. J., and Greenberger, L. M. HTI-286, a synthetic analogue of the tripeptide hemiasterlin, is a potent antimicrotubule agent that circumvents P-glycoprotein-mediated resistance in vitro and in vivo. Cancer Res., 63: 1838-1845, 2003). If a compound is recognized by P-glycoprotein, its $IC_{50}$ value will increase substantially (several hundred-fold) on going from KB to KB-8-5 to KB-V1; if a compound is not recognized, it will have similar $IC_{50}$ values (3-fold or less difference) on all three lines. For example, as shown in Table 2, KB-8-5 cells are moderately resistant to paclitaxel (19-fold), vincristine (11-fold), colchicine (3.4-fold) and doxorubicin (3.0-fold). Representative examples of this invention (Nos. 1, 2a, 4a, 20, 25, 30, 32) show less than a 2-fold change in $IC_{50}$ values.

Even slight interactions of compounds with P-glycoprotein can be determined with the KB-V1 line, which expresses a level of this protein higher than is typically found in clinical samples from a variety of tumors (Goldstein, L. J., Galski, H., Fojo, T., Willingham, M., Lai, S. L., Gazdar, A., Pirker, R., Green, A., Crist, W., Brodeur, G. M., Lieber, M., Cossman, J., Gottesman, M. M., and Pastan, I. Expression of a multidrug resistance gene in human cells. J. Natl. Cancer Inst. (Bethesda), 81: 116-124, 1989). KB-V1 cells are highly resistant to paclitaxel (>345-fold), vincristine (>156-fold), colchicine (116-fold), mitoxantrone (77-fold), and doxorubicin (>130-fold), representative examples of this invention (Nos. 20, 25, 30) show less than a 3-fold change in $IC_{50}$ compared to the parental KB line. This indicates that these compounds are not recognized at all by P-glycoprotein and therefore that these compounds completely overcome P-glycoprotein-mediated resistance to cell killing. Representative examples of the invention (Nos. 1a, 2a, 3a, 4a, 32) show recognition by P-glycoprotein.

TABLE 2

Activity of Representative Examples of the Invention and Reference Compounds in the MTS Cytotoxicity Standard Pharmacological Test Procedure with KB, KB-8.5 and KB-VI Cells

| Example or Reference Compound | Salt | $IC_{50}(nM)$[1] | | | Ratio[2] | |
|---|---|---|---|---|---|---|
| | | KB | KB 8.5 | KB VI | 8.5/KB | VI/KB |
| 1a | HCl Salt | 28 | 62 | 103 | 2.2 | 3.7 |
| 2a | HCl Salt | 24 | 64 | 1,117 | 2.7 | 48 |
| 3a | HCl Salt | 18 | 69 | 2,147 | 3.8 | 119 |
| 4a | HCl Salt | 24 | 58 | 162 | 2.5 | 7 |
| 20 | | 57 | 66 | 73 | 1.2 | 1.3 |
| 25 | | 59 | 67 | 165 | 1.1 | 2.8 |
| 30 | | 72 | 127 | 97 | 1.8 | 1.3 |
| 32 | TFA Salt | 11 | 15 | 108 | 1.4 | 9.9 |
| Paclitaxel | | 2.9 | 56 | >1,000 | 19 | >345 |
| Vincristine | | 6.4 | 72 | >1,000 | 11 | >156 |
| Colchicine | | 18 | 59 | 2,038 | 3.4 | 116 |
| Camptothecin | | 24 | 33 | 39 | 1.4 | 1.6 |
| Mitoxantrone | | 25 | 27 | 1,927 | 1.1 | 77 |
| Doxorubicin | | 23 | 70 | >3,000 | 3.0 | >130 |

[1]$IC_{50}$ values are means of 2 independent experiments.
[2]Ratio = $IC_{50}$ on KB 8.5 or KB VI cells/$IC_{50}$ on KB cells. A ratio of about 1 indicates no resistance.

1.3. (With HL-60 and HL-60/ADR Cells)
HL-60/ADR cells overexpress the multidrug resistance protein MRP1 which mediates resistance to some chemotherapeutics (Gottesman, M. M., Fojo, T., and Bates, S. E. Multidrug resistance in cancer: role of ATP-dependent transporters. Nature Rev. Cancer, 2: 48-58, 2002). The $IC_{50}$ values of representative examples of this invention, as well as reference compounds, on HL-60/ADR are compared to values on the sensitive parental HL-60 line. The results, shown in Table 3, indicate that whereas HL-60/ADR cells show resistance to vincristine (8.2-fold), colchicine (7.4-fold), mitoxantrone (17-fold), and doxorubicin (93-fold), these cells show no resistance to any of representative examples of the invention. This indicates that the compounds of this invention are not recognized by MRP1 and therefore overcome cellular resistance mediated by this transporter.

TABLE 3

Activity of Representative Examples of the Invention and Reference Compounds in the MTS Cytotoxicity Standard Pharmacological Test Procedure with HL-60 and HL-60/AR Cells

| Example or Reference Compound | Salt | $IC_{50}$ (nM)[1] HL-60 | HL-60/ADR | Ratio[2] |
|---|---|---|---|---|
| 1a | HCl Salt | 71 | 63 | 0.89 |
| 2a | HCl Salt | 43 | 47 | 1.1 |
| 3a | HCl Salt | 26 | 21 | 0.81 |
| 4a | HCl Salt | 52 | 34 | 0.65 |
| 20 | | 155 | 74 | 0.48 |
| 25 | | 104 | 68 | 0.65 |
| 30 | | 55 | 52 | 0.94 |
| 32 | TFA Salt | 7.1 | 6.6 | 0.92 |
| Paclitaxel | | 5.7 | 6.4 | 1.1 |
| Vincristine | | 2.5 | 20 | 8.2 |
| Colchicine | | 9.3 | 69 | 7.4 |
| Camptothecin | | 12 | 17 | 1.4 |
| Mitoxantrone | | 9.5 | 161 | 17 |
| Doxorubicin | | 23 | 2,085 | 93 |

[1]$IC_{50}$ values are means of 2 independent experiments.
[2]Ratio = $IC_{50}$ on HL-60/ADR cells/$IC_{50}$ on HL-60 cells. A ratio of about 1 indicates no resistance.

1.4. With S1 and S1-M1 Cells

S1-M1 cells overexpress the MXR transporter which mediates resistance to some chemotherapeutics (Gottesman, M. M., Fojo, T., and Bates, S. E. Miltidrug resistance in cancer: role of ATP-dependent transporters. Nature Rev. Cancer, 2: 48-58, 2002). The $IC_{50}$ values of representative examples of this invention, as well as reference compounds, on S1-M1 are compared to values on the sensitive parental S1 line. The results, shown in Table 4, indicate that whereas S1-M1 cells show resistance to mitoxantrone (>300-fold) and doxorubicin (74-fold), they show no resistance to representative examples of the invention. This indicates that the compounds of this invention are not recognized by MXR and therefore overcome cellular resistance mediated by this transporter.

TABLE 4

Activity of Representative Examples of the Invention and Reference Compounds in the MTS Cytotoxicity Standard Pharmacological Test Procedure with S1 and S1-M1 Cells

| Example or Reference Compound | Free Base/Salt | $IC_{50}$ (nM)[1] S1 | S1-M1 | Ratio[2] |
|---|---|---|---|---|
| 1a | HCl Salt | 73 | 75 | 1.0 |
| 2a | HCl Salt | 70 | 69 | 1.0 |
| 3a | HCl Salt | 61 | 71 | 1.2 |
| 4a | HCl Salt | 72 | 73 | 1.0 |
| 20 | | 85 | 91 | 1.1 |
| 25 | | 106 | 84 | 0.80 |
| 30 | | 66 | 78 | 1.2 |
| 32 | TFA Salt | 11 | 9.0 | 0.80 |
| Paclitaxel | | 8.1 | 4.4 | 0.54 |
| Vincristine | | 5.6 | 4.6 | 0.82 |
| Colchicine | | 18 | 60 | 3.3 |

TABLE 4-continued

Activity of Representative Examples of the Invention and Reference Compounds in the MTS Cytotoxicity Standard Pharmacological Test Procedure with S1 and S1-M1 Cells

| Example or Reference Compound | Free Base/Salt | $IC_{50}$ (nM)[1] S1 | S1-M1 | Ratio[2] |
|---|---|---|---|---|
| Camptotheci | | 8.9 | 17 | 1.9 |
| Mitoxantrone | | 10 | >3,000 | >300 |
| Doxorubicin | | 34 | 2,517 | 74 |

[1]$IC_{50}$ values are means of 2 independent experiments.
[2]Ratio = $IC_{50}$ on S1-M1 cells/$IC_{50}$ on S1 cells. A ratio of about 1 indicates no resistance.

2. Effects of Compounds on Polymerization of MAP-rich and Pure Tubulin in vitro

In this assay, control reactions with MAP-rich tubulin show an S-shaped absorbance profile characterized by three phases: first, a lag phase during which no change in absorbance occurs; second, a polymerization phase in which absorbance increases; and third, a plateau phase in which absorbance has reached a maximum and little or no further change occurs. Polymerization enhancers such as paclitaxel and docetaxel shorten or eliminate the lag phase, increase the rate of the polymerization phase, and often increase the height of the plateau. Polymerization inhibitors such as vincristine and colchicine reduce or prevent the absorbance increase. The compounds of this invention have a taxane-like effect on the polymerization reaction. This has been expressed quantitatively in Table 5 by dividing the mean $A_{340}$ of each sample at 20 min by the mean $A_{340}$ of the control at 20 min to give a fold enhancement over control. Paclitaxel shows an enhancement factor of 8.5. Examples of this invention have factors ranging up to 8.1, with the majority in the 5 to 6-fold range. Vincristine gave an enhancement factor of 0 because it completely inhibited polymerization of MAP-rich tubulin.

TABLE 5

Activity of Representative Examples of the Invention and Reference Compounds in the Tubulin Polymerization Standard Pharmacological Test Procedure with MAP-rich Tubulin

| Example | Salt | $\frac{A_{340} \text{ Compound}}{A_{340} \text{ Control}}$ |
|---|---|---|
| 1a | HCl Salt | 6.1 |
| 2 | | 5.8 |
| 3 | | 6.7 |
| 4a | HCl Salt | 8.1 |
| 6 | | 6.7 |
| 7 | | 6.4 |
| 8 | | 6.2 |
| 9 | | 5.8 |
| 10 | | 6.3 |
| 11a | HCl Salt | 6.8 |
| 12 | | 2.9 |
| 13 | | 5.4 |
| 14 | | 1.5 |
| 15 | | 5.5 |
| 16 | | 2.4 |
| 17 | | 4.8 |
| 18 | | 5.8 |
| 22 | | 1.2 |
| 23 | | 4.2 |
| 24 | | 1.2 |
| 25 | | 7.2 |
| 26 | | 4.6 |

TABLE 5-continued

Activity of Representative Examples of the Invention and
Reference Compounds in the Tubulin Polymerization Standard
Pharmacological Test Procedure with MAP-rich Tubulin

| Example | Salt | $A_{340}$ Compound $A_{340}$ Control |
|---|---|---|
| Paclitaxel | | 8.5 |
| Vincristine | | 0.0 |
| Control | | 1.0 |

Pure tubulin without added GTP shows no polymerization in control reactions. Docetaxel, and to a much lesser extent, paclitaxel, are able to induce polymerization of pure tubulin under these conditions. Several examples of this invention also induce polymerization of pure tubulin without GTP in a manner similar to docetaxel. Table 6 shows the mean absorbance at four time points after the start of the reaction for a single compound concentration. At this concentration (24.3 µM) docetaxel and representative examples 1a, 2a, 3a, 4a, 11a, 25, and 32 cause a rapid increase in absorbance within the first 5 min of reaction to a plateau. All seven of these examples also caused a lower and less rapid increase at 8.1 µM, but had no effect at 2.7 µM. Docetaxel, on the other hand, induced a small increase in absorbance even at 0.1 µM.

TABLE 6

Activity of Representative Examples of the Invention and
Reference Compounds in the Tubulin Polymerization Standard
Pharmacological Test Procedure with Pure Tubulin

| Compound | $A_{340}$ at | | | | |
|---|---|---|---|---|---|
| | 0 min | 5 min | 10 min | 15 min | 20 min |
| Control | 0 | 0 | 0 | 0 | 0 |
| Example 1a | 0 | 0.22 | 0.23 | 0.22 | 0.21 |
| Example 2a | 0 | 0.25 | 0.24 | 0.23 | 0.22 |
| Example 3a | 0 | 0.19 | 0.20 | 0.20 | 0.20 |
| Example 4a | 0 | 0.14 | 0.16 | 0.16 | 0.15 |
| Example 11a | 0 | 0.24 | 0.24 | 0.23 | 0.22 |
| Example 20 | 0 | 0.03 | 0.03 | 0.03 | 0.03 |
| Example 25 | 0 | 0.22 | 0.23 | 0.22 | 0.22 |
| Example 30 | 0 | 0.02 | 0.01 | 0.01 | 0.01 |
| Example 32 | 0 | 0.26 | 0.26 | 0.25 | 0.25 |
| Paclitaxel | 0 | 0 | 0 | 0.01 | 0.01 |
| Docetaxel | 0 | 0.20 | 0.20 | 0.20 | 0.20 |
| Vincristine | 0 | 0.01 | 0.01 | 0 | 0 |
| Colchicine | 0 | 0 | 0 | 0 | 0 |

3. Binding of Compounds to Tubulin

The site on highly purified bovine brain tubulin to which compounds of this invention bind is determined by competitive inhibition studies with the radioactive ligands [$^3$H]vinblastine, [$^3$H]colchicine, and [$^3$H]paclitaxel. The results, shown in Table 7, indicate that all of the tested compounds inhibit the binding of [$^3$H]vinblastine to tubulin heterodimer (11-19% of control), but do not inhibit binding of [$^3$H]colchicine to tubulin heterodimer or of [$^3$H]paclitaxel to microtubules. This is strong evidence that these compounds bind at the vinca/peptide site of tubulin and not at the colchicine or taxane sites. Most of the tested compounds actually enhance the binding of [$^3$H]colchicine by 12-34% above the control level. This suggests that the binding of these compounds to the vinca/peptide site may induce a conformational change in the protein molecule that results in enhanced colchicine binding. This change appears not to be induced by vincristine itself. Among the control compounds tested, vincristine inhibited [$^3$H]vinblastine binding but not [$^3$H]colchicine, and colchicine inhibited [$^3$H]colchicine binding but not [$^3$H]vinblastine. Vincristine and colchicine also appeared to inhibit the binding of [$^3$H]paclitaxel to microtubules; however, this is not due to binding competition but rather to depolymerization of the microtubules to which [$^3$H]paclitaxel binds. It is clear that compounds of this invention do not reduce [$^3$H]paclitaxel binding to microtubules, which indicates that they neither compete with [$^3$H]paclitaxel for binding nor depolymerize the microtubules to which [$^3$H]paclitaxel binds.

TABLE 7

Activity of Representative Examples of the Invention
and Reference Compounds in the Competitive Binding
Standard Pharmacological Test Procedure[1]

| | Radioactive Ligand | | | | | |
|---|---|---|---|---|---|---|
| | [$^3$H]Vinblastine | | [$^3$H]Colchicine | | [$^3$H]Paclitaxel | |
| Competitor | Mean[2] | SD[2] | Mean[2] | SD[2] | Mean[3] | SD[3] |
| Control | 100 | | 100 | | 100 | |
| Example 1a | 12 | 1.7 | 129 | 9.7 | 108 | 5.6 |
| Example 2a | 11 | 1.1 | 122 | 17.7 | 104 | 2.1 |
| Example 3a | 11 | 0.5 | 134 | 12.8 | 105 | 4.1 |
| Example 4a | 15 | 3.6 | 134 | 15.5 | 104 | 3.1 |
| Example 11a | 12 | 1.1 | 121 | 9.7 | 107 | 0 |
| Example 20 | 19 | 1.5 | 98 | 2.9 | 104 | 3.1 |
| Example 25 | 14 | 1.5 | 126 | 12.6 | 99 | 5.9 |
| Example 30 | 14 | 1.5 | 112 | 4.7 | 91 | 1.8 |
| Example 32 | 15 | 1.9 | 94 | 7.1 | 93 | 2.8 |
| Vincristine | 5 | 1.0 | 99 | 7.9 | 22 | 0.9 |
| Colchicine | 125 | 12.6 | 6 | 1.9 | 19 | 0.2 |
| Paclitaxel | 92 | 7.8 | 93 | 12.3 | 35 | 1.6 |

[1]Results are expressed as percent of binding to control without competitor.
[2]Data are from 1 (4 replicates) or 2 (8 replicates) independent experiments.
[3]Data are from 1 to 4 independent experiments (3 to 12 replicates).

4. Effect of Compounds on Cell Cycle Progression

This procedure measures the percentages of cells in a population that are in the G1, S, and G2/M phases of the cell cycle. It utilizes staining of cell nuclei with propidium iodide and analysis by flow cytometry. The procedure also gives an estimate of apoptosis caused by drug treatment by measurement of the appearance of particles with sub-G1 amounts of DNA. At high concentrations (i.e., higher than about 5×IC$_{50}$ concentrations) microtubule-active compounds characteristically arrest cells in the G2/M phase of the cell cycle because of disruption of the microtubules that comprise the mitotic spindle. However at lower concentrations (near IC$_{50}$ values) on some cell lines, e.g. HeLa, taxanes such as paclitaxel and docetaxel induce substantial apoptosis before a G2/M block is observed (Jordan, M. A., Wendell, K., Gardiner, S., Derry, W. B., Copp, H., and Wilson, L. Mitotic block induced in HeLa cells by low concentrations of paclitaxel (Taxol) results in abnormal mitotic exit and apoptotic cell death. Cancer Res., 56: 816-825, 1996); this is not the case with microtubule depolymerizers such as vincristine and colchicine. Representative examples of this invention are tested in this procedure after 18 hr of culture with cells at multiple concentrations to see if they followed the "stabilizer" (taxane) or "destabilizer" (vincristine, colchicine) pattern. Results presented in Table 8 show that they follow the "stabilizer" pattern.

For instance, example 1a showed about 70% apoptosis at 40 nM, close to its IC$_{50}$ on HeLa cells, with no increase in the G2/M fraction compared to the untreated control. As concentration increased above 40 nM, the apoptotic fraction decreased and the G2/M fraction increased. Similar patterns are seen with examples 2a, 3a, and 4a, and docetaxel. However, vincristine and colchicine showed a parallel increase in both apoptotic and G2/M fractions, and the extent of apoptosis at 18 hr is much lower.

TABLE 8

Activity of Representative Examples of the Invention and Reference Compounds in the Cell Cycle Analysis Standard Pharmacological Test Procedure with HeLa Cells

| Compound | Conc. (nM) | Apop[1] | G1 | S | G2/M | >4N |
|---|---|---|---|---|---|---|
| Example 1a | 0 | 5 | 61 | 20 | 14 | 1 |
|  | 20 | 13 | 54 | 18 | 14 | 2 |
|  | 30 | 38 | 35 | 12 | 14 | 1 |
|  | 40 | 71 | 7 | 8 | 13 | 1 |
|  | 50 | 63 | 6 | 9 | 20 | 2 |
|  | 60 | 52 | 5 | 10 | 32 | 3 |
|  | 70 | 26 | 3 | 9 | 57 | 4 |
|  | 80 | 24 | 4 | 9 | 58 | 5 |
|  | 90 | 22 | 5 | 10 | 58 | 6 |
|  | 100 | 24 | 4 | 10 | 58 | 5 |
|  | 110 | 24 | 6 | 13 | 53 | 5 |
|  | 120 | 28 | 6 | 14 | 48 | 5 |
| Example 2a | 0 | 4 | 62 | 20 | 14 | 1 |
|  | 20 | 28 | 41 | 14 | 16 | 2 |
|  | 30 | 62 | 12 | 10 | 16 | 2 |
|  | 40 | 44 | 5 | 9 | 39 | 2 |
|  | 50 | 25 | 5 | 9 | 58 | 4 |
|  | 60 | 24 | 4 | 9 | 58 | 4 |
|  | 70 | 22 | 6 | 11 | 57 | 4 |
|  | 80 | 26 | 7 | 11 | 52 | 4 |
|  | 90 | 30 | 7 | 13 | 46 | 4 |
|  | 100 | 34 | 7 | 15 | 41 | 4 |
|  | 110 | 37 | 9 | 14 | 37 | 4 |
|  | 120 | 39 | 8 | 15 | 36 | 4 |
| Example 3a | 0 | 6 | 69 | 14 | 11 | 1 |
|  | 20 | 29 | 42 | 12 | 16 | 1 |
|  | 30 | 55 | 11 | 11 | 21 | 2 |
|  | 40 | 50 | 6 | 10 | 31 | 3 |
|  | 50 | 32 | 5 | 8 | 52 | 3 |
|  | 60 | 25 | 4 | 9 | 58 | 4 |
|  | 70 | 21 | 5 | 9 | 61 | 4 |
|  | 80 | 24 | 5 | 11 | 57 | 5 |
|  | 90 | 23 | 5 | 8 | 60 | 4 |
|  | 100 | 25 | 5 | 10 | 55 | 5 |
|  | 110 | 26 | 6 | 10 | 54 | 5 |
|  | 120 | 30 | 6 | 12 | 48 | 5 |
| Example 4a | 0 | 4 | 67 | 16 | 12 | 1 |
|  | 20 | 6 | 60 | 17 | 15 | 2 |
|  | 30 | 44 | 29 | 12 | 15 | 1 |
|  | 40 | 65 | 8 | 8 | 17 | 2 |
|  | 50 | 54 | 6 | 9 | 29 | 2 |
|  | 60 | 64 | 13 | 8 | 15 | 2 |
|  | 70 | 25 | 3 | 8 | 60 | 4 |
|  | 80 | 20 | 5 | 7 | 63 | 5 |
|  | 90 | 22 | 5 | 10 | 59 | 5 |
|  | 100 | 23 | 7 | 9 | 57 | 5 |
|  | 110 | 23 | 6 | 10 | 56 | 5 |
|  | 120 | 27 | 7 | 10 | 53 | 4 |
| Docetaxel | 0 | 6 | 55 | 19 | 18 | 2 |
|  | 0.25 | 8 | 58 | 17 | 16 | 2 |
|  | 0.5 | 19 | 48 | 18 | 14 | 2 |
|  | 1 | 35 | 35 | 15 | 14 | 2 |
|  | 2 | 48 | 19 | 18 | 14 | 2 |
|  | 3 | 52 | 15 | 17 | 14 | 2 |
|  | 4 | 49 | 12 | 16 | 22 | 2 |
|  | 5 | 42 | 9 | 17 | 31 | 3 |
|  | 6 | 37 | 10 | 17 | 33 | 4 |
|  | 8 | 29 | 7 | 11 | 48 | 4 |
|  | 10 | 35 | 9 | 16 | 37 | 4 |
|  | 20 | 38 | 8 | 12 | 40 | 3 |
| Vincristine | 0 | 6 | 62 | 16 | 15 | 2 |
|  | 1 | 6 | 57 | 18 | 17 | 2 |
|  | 2 | 8 | 55 | 18 | 18 | 2 |
|  | 4 | 9 | 50 | 17 | 23 | 2 |
|  | 6 | 11 | 45 | 15 | 27 | 3 |
|  | 8 | 12 | 40 | 14 | 32 | 3 |
|  | 10 | 16 | 27 | 13 | 41 | 3 |
|  | 15 | 19 | 20 | 14 | 44 | 4 |
|  | 20 | 18 | 15 | 12 | 51 | 4 |
|  | 25 | 17 | 14 | 13 | 52 | 4 |
|  | 30 | 19 | 12 | 11 | 55 | 4 |
|  | 40 | 18 | 8 | 13 | 57 | 4 |
| Colchicine | 0 | 4 | 57 | 17 | 19 | 2 |
|  | 5 | 6 | 60 | 17 | 16 | 2 |
|  | 10 | 7 | 59 | 16 | 18 | 2 |
|  | 12.5 | 7 | 55 | 18 | 18 | 2 |
|  | 15 | 9 | 50 | 17 | 23 | 2 |
|  | 17.5 | 9 | 51 | 18 | 21 | 2 |
|  | 20 | 13 | 40 | 18 | 28 | 2 |
|  | 25 | 14 | 36 | 20 | 27 | 3 |
|  | 30 | 14 | 27 | 20 | 36 | 3 |
|  | 40 | 11 | 16 | 22 | 48 | 4 |
|  | 50 | 11 | 11 | 18 | 56 | 4 |
|  | 100 | 15 | 11 | 16 | 55 | 3 |

[1]Apop = Apoptosis

5. In Vivo Anti-Tumor Activity of Compounds

A number of experiments with human tumor xenografts in athymic mice have been done to evaluate the ability of compounds of this invention to inhibit tumor growth in vivo. Table 9 shows results for example 2a with mice bearing H157 non-small cell lung carcinoma (NSCLC). The compound inhibited tumor growth at 25, 15 and 7.5 mg/kg when dosed intravenously on days 0 and 6. In another experiment with H157 NSCLC, the succinate salt of example 2c is active when given intravenously on days 0 and 7 at 20 and 10 mg/kg (Table 10). Example 2a also inhibited the growth of another NSCLC, A549 (Table 11), at 25 and 20 mg/kg, but not at 15 mg/kg, when dosed intravenously on days 0, 6, 13, and 20. Example 2a inhibited the growth of HT-29 colon carcinoma xenografts as shown in Table 12 when given intravenously at 25 mg/kg on days 1 and 7. In addition, example 2a inhibited the growth of U87-MG glioblastoma when given orally as a single dose on day 0 at 30, 20, and 10 mg/kg, but not at 5 or 2.5 mg/kg (Table 13). Example 2a is also active against HCT-15 colon carcinoma at 20 mg/kg when dosed intravenously on days 1, 8, and 15 (Table 14). HCT-15 overexpresses P-glycoprotein and is resistant to paclitaxel and vincristine.

Examples 1a, 2a, 3a, and 4a are tested against LOX melanoma xenografts. The results in Table 15 show that all four compounds are active at 6 and 3 mg/kg, but not at 1 mg/kg, when dosed intravenously on days 1, 5, 9, and 13.

Examples 1a, 2a, 3a, and 4a are also tested against DLD1 colon carcinoma. This tumor overexpresses P-glycoprotein and is resistant to paclitaxel and vinca alkaloids. Example 1 at 15 mg/kg, and example 2 at 20 mg/kg, are active when dosed intravenously on days 1, 5, 9, and 13 (Table 16).

Examples 3a and 9 are tested against U-87 MG glioblastoma xenografts (Table 17). With oral dosing, example 3a is active at 40, 20, and 10 mg/kg, and example 9 is active at 20 mg/kg.

Example 4 inhibited the growth of A549 lung carcinoma as shown in Table 18 when given intravenously q4dX8 at 40 mg/kg, but not at 20 or 10 mg/kg.

Finally, example 20 is active against LoVo human colon carcinoma xenografts when dosed orally on days 1, 7 and 14 at 50 and 30 mg/kg (Table 19). When dosed in an identical manner, example 32 is active at 50 mg/kg but not at 30 mg/kg (Table 19).

TABLE 9

In Vivo Activity of Example 2a in the Human Tumor Xenograft Standard Pharmacological Test Procedure with Mice Bearing H157 Human Non-Small Cell Lung Carcinoma

| Compound | Schedule (days) | Route | Dose (mg/kg) | T/C on day 0 | 7 | 11 | 14 |
|---|---|---|---|---|---|---|---|
| Example 2a | 0, 6 | IV | 25 | 1.03 | 0.62* | 0.29** | 0.30** |
| | | | 15 | 1.02 | 0.55* | 0.44* | 0.42** |
| | | | 7.5 | 1.04 | 0.54** | 0.42** | 0.45** |

\* = p < 0.05
\*\* = p < 0.01
Vehicle is normal saline

TABLE 10

In Vivo Activity of Example 2c in the Human Tumor Xenograft Standard Pharmacological Test Procedure with Mice Bearing H157 Human Non-Small Cell Lung Carcinoma

| Compound | Schedule (days) | Route | Dose (mg/kg) | T/C on day 0 | 2 | 5 | 8 | 12 | 15 |
|---|---|---|---|---|---|---|---|---|---|
| Example 2c | 0, 7 | IV | 20 | 0.98 | 0.96 | 0.50** | 0.51* | 0.44* | 0.24** |
| | | | 10 | 1.07 | 1.09 | 1.00 | 0.96 | 0.49* | 0.38* |

\* = p < 0.05
\*\* = p < 0.01
Vehicle is normal saline

TABLE 11

In Vivo Activity of Example 2a in the Human Tumor Xenograft Standard Pharmacological Test Procedure with Mice Bearing A549 Human Non-Small Cell Lung Carcinoma

| Compound | Schedule (days) | Route | Dose (mg/kg) | T/C on day 0 | 7 | 14 | 21 | 27 | 35 |
|---|---|---|---|---|---|---|---|---|---|
| Example 2a | 0, 6, 13, 20 | IV | 25 | 0.99 | 0.72* | 0.51** | 0.57* | 0.48* | 0.44* |
| | | | 20 | 0.97 | 0.79 | 0.55** | 0.59* | 0.50* | 0.49* |
| | | | 15 | 1.01 | 0.75* | 0.61** | 0.83 | 0.75 | 0.76 |

\* = p < 0.05
\*\* = p < 0.01
Vehicle is normal saline

TABLE 12

In Vivo Activity of Example 2a in the Human Tumor Xenograft Standard Pharmacological Test Procedure with Mice Bearing HT-29 Human Colon Carcinoma

| Compound | Schedule (days) | Route | Dose (mg/kg) | T/C on day 0 | 7 | 10 | 13 | 21 | 24 |
|---|---|---|---|---|---|---|---|---|---|
| Example 2a | 1, 7 | IV | 25 | 1.00 | 0.44** | 0.34** | 0.26** | 0.43** | 0.46** |

\*\* = p < 0.01
Vehicle is normal saline

TABLE 13

In Vivo Activity of Example 2 in the Human Tumor Xenograft Standard Pharmacological Test Procedure with Mice Bearing U87-MG Human Glioblastoma

| Compound | Schedule (days) | Route | Dose (mg/kg) | T/C on day 0 | 4 | 8 | 11 | 14 |
|---|---|---|---|---|---|---|---|---|
| Example 2 | 0 | PO | 30 | 0.95 | 0.41** | 0.24** | 0.19** | 0.23** |
|  | 0 | PO | 20 | 0.97 | 0.59** | 0.38** | 0.28** | 0.30** |
|  | 0 | PO | 10 | 1.00 | 0.60** | 0.51** | 0.40** | 0.41** |
|  | 0 | PO | 5 | 1.02 | 0.71* | 0.75* | 0.65** | 0.68** |
|  | 0 | PO | 2.5 | 1.00 | 0.84 | 0.82 | 0.74* | 0.74* |

\* = p < 0.05
\*\* = p < 0.01
Vehicle is Klucel

TABLE 14

In Vivo Activity of Example 2a in the Human Tumor Xenograft Standard Pharmacological Test Procedure with Mice Bearing HCT-15 Human Colon Carcinoma

| Compound | Schedule (days) | Route | Dose (mg/kg) | T/C on day 0 | 7 | 13 | 20 |
|---|---|---|---|---|---|---|---|
| Example 2a | 1, 8, 15 | IV | 25 | 1.00 | 0.78 | 0.60 | 0.44 |
|  |  |  | 20 | 1.00 | 0.86 | 0.50* | 0.43* |
|  |  |  | 10 | 1.00 | 0.81 | 1.03 | 0.75 |

\* = p < 0.05
\*\* = p < 0.01
Vehicle is normal saline
Note: 2 of 5 mice died in 25 mg/kg group

TABLE 15

In Vivo Activity of Examples 1a, 2a, 3a, and 4a in the Human Tumor Xenograft Standard Pharmacological Test Procedure with Mice Bearing LOX Human Melanoma

| Compound | Schedule (days) | Route | Dose (mg/kg) | T/C on day 0 | 7 | 13 |
|---|---|---|---|---|---|---|
| Example 1a | 1, 5, 9, 13 | IV | 6 | 1.00 | 0.12** | 0.07** |
|  |  |  | 3 | 1.00 | 0.13** | 0.17* |
|  |  |  | 1 | 1.00 | 0.80 | 1.02 |
| Example 2a | 1, 5, 9, 13 | IV | 6 | 1.00 | 0.17** | 0.12** |
|  |  |  | 3 | 1.00 | 0.31** | 0.36 |
|  |  |  | 1 | 1.00 | 0.81 | 0.95 |
| Example 3a | 1, 5, 9, 13 | IV | 6 | 1.00 | 0.22** | 0.07** |
|  |  |  | 3 | 1.00 | 0.34* | 0.38 |
|  |  |  | 1 | 1.00 | 0.77 | 0.85 |
| Example 4a | 1, 5, 9, 13 | IV | 6 | 1.00 | 0.21** | 0.14** |
|  |  |  | 3 | 1.00 | 0.20** | 0.19** |
|  |  |  | 1 | 1.00 | 0.80 | 0.79 |

\* = p < 0.05
\*\* = p < 0.01
Vehicle is normal saline

TABLE 16

In Vivo Activity of Examples 1a, 2a, 3a, and 4a in the Human Tumor Xenograft Standard Pharmacological Test Procedure with Mice Bearing DLD1 Human Colon Carcinoma

| Compound | Schedule (days) | Route | Dose (mg/kg) | T/C on day 0 | 7 | 14 | 21 |
|---|---|---|---|---|---|---|---|
| Example 1a | 1, 5, 9, 13 | IV | 20 | 1.00 | 0.31** | Toxic | — |
|  |  |  | 15 | 1.00 | 0.21** | 0.25 | 0.31 |
|  |  |  | 10 | 1.00 | 0.63 | 0.51 | 0.58 |
| Example 2a | 1, 5, 9, 13 | IV | 20 | 1.00 | 0.46* | 0.33 | 0.53 |
|  |  |  | 15 | 1.00 | 0.59 | 0.54 | 0.74 |
|  |  |  | 10 | 1.00 | 0.66 | 0.65 | 0.72 |
| Example 3a | 1, 5, 9, 13 | IV | 25 | 1.00 | 0.59 | 0.46 | 0.60 |
|  |  |  | 20 | 1.00 | 0.55 | 0.56 | 0.73 |
|  |  |  | 10 | 1.00 | 0.77 | 0.75 | 0.84 |
| Example 4a | 1, 5, 9, 13 | IV | 25 | 1.00 | 0.63 | 0.49 | 0.48 |
|  |  |  | 20 | 1.00 | 0.55 | 0.44 | 0.61 |
|  |  |  | 10 | 1.00 | 0.56 | 0.68 | 0.74 |

\* = p < 0.05
\*\* = p < 0.01
Vehicle is normal saline

TABLE 17

In Vivo Activity of Examples 3a and 9 in the Human Tumor Xenograft Standard Pharmacological Test Procedure with Mice Bearing U87-MG Human Glioblastoma

| Compound | Schedule (days) | Route | Dose (mg/kg) | T/C on day 0 | 3 | 7 | 10 | 13 | 17 |
|---|---|---|---|---|---|---|---|---|---|
| Example 3a | 1, 5, 9 | PO | 40 | 1.02 | 0.73 | 0.65** | 0.48** | 0.30** | 0.20** |
|  |  |  | 20 | 1.01 | 0.90 | 0.73 | 0.63** | 0.42** | 0.39** |
|  |  |  | 10 | 0.99 | 1.08 | 0.85 | 0.69** | 0.52** | 0.51** |
| Example 9 | 1, 5, 9 | PO | 20 | 1.04 | 0.93 | 0.70 | 0.50** | 0.34** | 0.45** |

TABLE 17-continued

In Vivo Activity of Examples 3a and 9 in the Human Tumor Xenograft Standard Pharmacological Test Procedure with Mice Bearing U87-MG Human Glioblastoma

| Compound | Schedule (days) | Route | Dose (mg/kg) | T/C on day 0 | 3 | 7 | 10 | 13 | 17 |
|---|---|---|---|---|---|---|---|---|---|

\* = $p < 0.05$
\*\* = $p < 0.01$
Vehicle is normal saline

TABLE 18

In Vivo Activity of Example 4a in the Human Tumor Xenograft Standard Pharmacological Test Procedure with Mice Bearing A549 Human Non-Small Cell Lung Carcinoma

| Compound | Schedule (days) | Route | Dose (mg/kg) | T/C on day 0 | 7 | 14 | 21 | 27 | 35 |
|---|---|---|---|---|---|---|---|---|---|
| Example 4a | 1, 5, 9, 13, 17, 21, 25, 29 | IV | 40 | 0.97 | 0.71 | 0.53\*\* | 0.46\*\* | 0.52\*\* | 0.47\*\* |
| | | | 20 | 0.99 | 0.86 | 0.80 | 0.72 | 0.78 | 0.77 |
| | | | 10 | 0.98 | 0.81 | 0.74 | 0.68 | 0.80 | 0.79 |

\* = $p < 0.05$
\*\* = $p < 0.01$
Vehicle is normal saline

TABLE 19

In Vivo Activity of Examples 20 and 32 in the Human Tumor Xenograft Standard Pharmacological Test Procedure with Mice Bearing LoVo Human Colon Carcinoma

| Compound | Schedule (days) | Route | Dose (mg/kg) | T/C an day 0 | 7 | 14 | 21 | 28 | 35 |
|---|---|---|---|---|---|---|---|---|---|
| Example 20 | 1, 7, 14 | PO | 50 | 1.00 | 0.27\*\* | 0.46\*\* | 0.33\*\* | 0.29\*\* | 0.31\* |
| | | | 30 | 1.00 | 0.37\* | 0.35\*\* | 0.35 | 0.28 | 0.35 |
| Example 32 | 1, 7, 14 | PO | 50 | 1.00 | 0.41 | 0.44\* | 0.27\* | 0.31 | 0.26 |
| | | | 30 | 1.00 | 0.55 | 0.68 | 0.35 | 0.43 | 0.53 |

\* = $p < 0.05$
\*\* = $p < 0.01$
Vehicle is 0.5% Methocel-0.4% Tween 80

Compounds of this invention show potent cytotoxic activity against multiple human cancer cell lines in culture, including lines that are resistant to paclitaxel and vincristine because of drug transporter overexpression. The compounds of the invention enhance the initial rate of MAP-rich tubulin polymerization, in a manner reminiscent of taxanes and distinct from the inhibitory effects of depolymerizers such as vinca alkaloids and colchicine. Compounds of the invention also induce polymerization of pure tubulin in the absence of GTP. Compounds of this invention further induce apoptosis in target cells at low concentrations (around cytotoxic $IC_{50}$ values) without cell cycle block, another property that is characteristic of taxanes but not vincas or colchicine. Representative compounds of the invention inhibit the growth of several human tumor xenografts in athymic mice, including tumors resistant to taxanes and vinca alkaloids.

The following reference examples are useful for the preparation of the representative non-limiting examples of compounds of this invention which are useful as promoters of microtubule polymerization and as anticancer agents.

REFERENCE EXAMPLE 1

(1S)-2,2,2-Trifluoro-1-methylethylamine hydrogen chloride

The product, (1S)-2,2,2-trifluoro-1-methylethylamine hydrogen chloride is prepared according to the conditions disclosed in U.S. Pat. Nos. 5,986,135 and 6,204,269.

REFERENCE EXAMPLE 2

(1R)-2,2,2-Trifluoro-1-methylethylamine Hydrogen chloride

The product, (1R)-2,2,2-trifluoro-1-methylethylamine hydrogen chloride is prepared according to the conditions disclosed in U.S. Pat. Nos. 5,986,135 and 6,204,269, using L-(+)-tartaric acid in place of D-(−)-tartaric acid.

REFERENCE EXAMPLE 3

5-Chloro-6-(2,4-difluorophenyl)-N-[(1S)-2,2,2-trifluoro-1-methylethyl][1,2,4]triazolo[1,5-a]pyrimidin-7-amine The product, 5-chloro-6-(2,4-difluorophenyl)-N-[(1S)-2,2,2-trifluoro-1-methylethyl][1,2,4]triazolo[1,5-a]pyrimidin-7-amine is prepared according to the conditions disclosed in U.S. Pat. No. 5,986,135, except that DMF is used as solvent in the last step, as described herein in Example 1.

REFERENCE EXAMPLE 4

5-Chloro-6-(2,3,6-trifluorophenyl)-N-[(1S)-2,2,2-trifluoro-1-methylethyl][1,2,4]triazolo[1,5-a]pyrimidin-7-amine The product, 5-chloro-6-(2,3,6-trifluorophenyl)-N-[(1S)-2,2,2-trifluoro-1-methylethyl][1,2,4]triazolo[1,5-a]pyrimidin-7-amine is prepared according to the conditions disclosed in U.S. Pat. No. 5,986,135, except that DMF is used as solvent in the last step, as described herein in Example 1.

REFERENCE EXAMPLE 5

5,7-Dichloro-6-(2,4,6-trifluorophenyl)[1,2,4]triazolo[1,5-a]pyrimidine

The product, 5,7-dichloro-6-(2,4,6-trifluorophenyl)[1,2,4]triazolo[1,5-a]pyrimidine is prepared according to the conditions disclosed in U.S. Pat. Nos. 6,117,876 and 6,297,251.

REFERENCE EXAMPLE 6

5,7-Dihydroxy-6-(2,4,6-trifluorophenyl)[1,2,4]triazolo[1,5-a]pyrimidine

The product 5,7-dihydroxy-6-(2,4,6-trifluorophenyl)[1,2,4]triazolo[1,5-a]pyrimidine is prepared according to the conditions disclosed in U.S. Pat. Nos. 6,117,876, and 6,297,251.

REFERENCE EXAMPLE 7

Diethyl 2-(2,6-difluoro-4-methoxyphenyl)malonate

The product, diethyl 2-(2,6-difluoro-4-methoxyphenyl)malonate is prepared according to the conditions disclosed in U.S. Pat. No. 5,981,534.

REFERENCE EXAMPLE 8

3-(Methylamino)propan-1-ol

The product, 3-(methylamino)propan-1-ol is prepared according to the conditions disclosed in *J. Org. Chem.* 44, 2718 (1979).

REFERENCE EXAMPLE 9

3-(Ethylamino)propan-1-ol

The product, 3-(ethylamino)propan-1-ol is prepared according to the conditions disclosed in *J. Chem. Soc. B*, 1300 (1971).

REFERENCE EXAMPLE 10

3-[Ethyl(methyl)amino]propan-1-ol

The product, 3-[ethyl(methyl)amino]propan-1-ol is prepared according to the conditions disclosed in *J. Am. Chem. Soc.* 54, 2484 (1932).

REFERENCE EXAMPLE 11

3-Piperidin-1-ylpropan-1-ol

The product, 3-piperidin-1-ylpropan-1-ol is prepared according to the conditions described in *Tetr. Lett.* 35, 761 (1994) with the exception that the crude product is used as is without distillation.

REFERENCE EXAMPLE 12

3-Morpholin-4-ylpropan-1-ol

The product, 3-morpholin-4-ylpropan-1-ol is prepared according to the conditions described in *Tetr. Lett.* 35, 761 (1994) with the exception that the crude product is used as is without distillation.

REFERENCE EXAMPLE 13

3-Pyrrolidin-1-ylpropan-1-ol

The product, 3-pyrrolidin-1-ylpropan-1-ol is prepared according to the conditions described in *Tetr. Lett.* 35, 761 (1994) with the exception that the crude product is used as is without distillation.

REFERENCE EXAMPLE 14

3-(Methylpiperazin-1-yl)propan-1-ol

The product, 3-(methylpiperazin-1-yl)propan-1-ol is prepared according to the conditions described in *Tetr. Lett.* 35, 761 (1994) with the exception that the crude product is used as is without distillation.

REFERENCE EXAMPLE 15

3-Azetidin-1-ylpropan-1-ol

The product, 3-azetidin-1-ylpropan-1-ol is prepared according to the conditions described in *Tetr. Lett.* 35, 761 (1994) with the exception that the crude product is used as is without distillation.

REFERENCE EXAMPLE 16

3-(Dimethylamino)propan-1-thiol

The product, 3-(dimethylamino)propan-1-thiol is prepared according to the conditions described in *J. Organomet. Chem.* 480, 177 (1994).

REFERENCE EXAMPLE 17

3-[(4-Methoxybenzyl)oxy]-1-propanol

The product, 3-[(4-methoxybenzyl)oxy]-1-propanol is prepared according to the conditions described in *Tetrahedron* 54, 1 (1998).

The following examples are representative non-limiting examples of compounds of this invention.

EXAMPLE 1

5-Chloro-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine

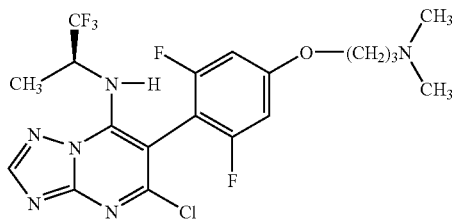

Step A: 5-Chloro-6-(2,4,6-trifluorophenyl)-N-[(1S)-2,2,2-trifluoro-1-methylethyl][1,2,4]triazolo[1,5-a]pyrimidin-7-amine A mixture of 5,7-dichloro-6-(2,4,6-trifluorophenyl)[1,2,4]triazolo[1,5-a]pyrimidine (3.0 g, 9.4 mmol), (1S)-2,2,2-trifluoro-1-methylethylamine hydrogen chloride (4.2 g, 28.2 mmol), and N,N-diisopropylethylamine (4.9 mL, 28.2 mmol) in 100 mL of N,N-dimethylformamide is stirred at room temperature under nitrogen atmosphere for 13 h. The reaction mixture is diluted with ethyl acetate. The organic layer is washed with 1 N hydrochloric acid (2×) and saturated sodium chloride (2×), dried over magnesium sulfate, and concentrated to a residue. The residue is chromatographed over silica gel, eluting with 20% ethyl acetate in hexanes. Concentration provides 5-chloro-6-(2,4,6-trifluorophenyl)-N-[(1S)-2,2,2-trifluoro-1-methylethyl][1,2,4]triazolo[1,5-a]pyrimidin-7-amine as a light yellow solid (3.56 g). MS: m/z 396.0 (M+H).

Step B: 5-Chloro-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine To a solution of 5-chloro-6-(2,4,6-trifluorophenyl)-N-[(1S)-2,2,2-trifluoro-1-methylethyl][1,2,4]triazolo[1,5-a]pyrimidin-7-amine (600 mg, 1.5 mmol) and 3-dimethylamino-1-propanol (1.03 g, 10 mmol) in 5 mL of dimethylsulfoxide at room temperature is added sodium hydride (60% in mineral oil, 400 mg, 10 mmol). The mixture is heated at 50° C. for 30 min, and cooled to room temperature. Water is added to quench the reaction, and the product is extracted with ethyl acetate (x2). The combined organic extracts are washed with saturated sodium chloride (x4), dried over magnesium sulfate, and concentrated to a residue. The residue is chromatographed over silica gel, eluting with a gradient of ethyl acetate to 20% methyl alcohol in ethyl acetate. Concentration provides 5-chloro-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine as a colorless oil (486 mg). MS: m/z 479.2 (M+H).

EXAMPLE 1a 5-chloro-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine hydrogen chloride Salt The product of Example 1,5-chloro-6-{4-[3-dimethylamino)propoxy]-2,6-difluorophenyl}-N-[(1S)-2,2,2-trifluoro-1-methylethyl][1,2,4]triazolo[1,5-a]pyrimidin-7-amine is dissolved in methylene chloride (50 mL) and filtered. To the filtrate is bubbled hydrogen chloride gas. Concentration provides 5-chloro-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine hydrogen chloride salt as a white solid (540 mg).

EXAMPLE 2

5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine;

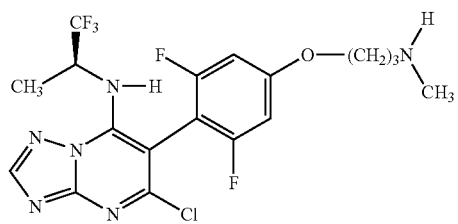

To sodium hydride (60% in mineral oil, 2.3 g, 57.6 mmol) in 20 mL of dimethylsulfoxide at room temperature is added a solution of 3-(methylamino)propan-1-ol (5.14 g, 57.6 mmol) in 10 mL of dimethylsulfoxide. The solution is stirred at room temperature for 1 h, and 5-chloro-6-(2,4,6-trifluorophenyl)-N-[(1S)-2,2,2-trifluoro-1-methylethyl][1,2,4]triazolo[1,5-a]pyrimidin-7-amine (5.7 g, 14.4 mmol) is added. The mixture is heated at 60° C. for 3 h, and cooled to room temperature. The reaction mixture is diluted with ethyl acetate, and washed with water and saturated sodium chloride. The organic layer is dried over magnesium sulfate, and concentrated to a residue. The residue is triturated with small amount of acetone, then hexanes, and chromatographed over silica gel, eluting with a gradient of 100% ethyl acetate to 100% methyl alcohol. Concentration provides 5-chloro-6{2,6-difluoro-4-[3-(methylamino)propoxy]phenyl}-N-[(1S)-2,2,2-trifluoro-1-methylethyl][1,2,4]triazolo[1,5-a]pyrimidin-7-amine as a white solid (2.7 g). MS: m/z 465.1 (M+H).

EXAMPLE 2a

5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine hydrogen chloride The product of Example 2 is dissolved in 10% methyl alcohol in methylene chloride (150 mL) and filtered. To the filtrate is bubbled hydrogen chloride gas. Concentration provides 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine hydrogen chloride salt as a light yellow solid (2.92 g).

EXAMPLE 2b

5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine Fumarate Salt To a slurry of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine hydrochloride (7.50 g, 15.0 mmol) and water (100 mL) is added sodium hydroxide solution (10 N, 2.0 mL, 20 mmol) dropwise. Then, fumaric acid (3.48 g, 30 mmol) is added. The mixture is stirred for about 15-20 min and then heated to about 65-75° C. and stirred until all of the solid dissolves. The solution is filtered and the filtrate is cooled to about 0-5° C. over about 1 h. The mixture is stirred for 1 h and then filtered and the collected solid washed with cold water and isopropanol. The solid is dried under vacuum at about 60° C./10 mmHg for about 20 h to give a white solid (6.54 g, 75%) in anhydrous form. A portion of the compound is placed in a drying dish at 80-100% relative humidity (RH) and room temperature for about 24 h. The compound absorbed 5.8% water forming a dihydrate which is stable at room temperature and at 5-100% relative humidity (RH). $^1$H NMR (CDCl$_3$): δ 8.43 (s, 1H), 6.86 (d, 2H, J=10.2 Hz), 6.51 (s, 2H), 5.84 (m, 1H), 4.15 (t, 2H, J=7.9 Hz), 3.04 (t, 2H, J=7.2 Hz), 2.57 (s, 3H), 2.08 (m, 2H), 1.33 (d, J=6.7, 3H).

This compound absorbs two mole waters at 5%-100% RH to become its dihydrate. 5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate salt dihydrate.

EXAMPLE 2c

5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine Succinate Salt A mixture of 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine (9.00 g, 19.4 mmol) and succinic acid (2.75 g, 23.3 mmol) in water (90 mL) is stirred for about 15-20 min and then heated to about 65-75° C. The solution is filtered and the filtrate is cooled to about 0-5° C. over about 1 h. The mixture is stirred for about 1 h and then filtered and the collected solid washed with cold water (2×9 mL) and cold isopropanol (9 mL). The solid is dried under vacuum at about 40° C./10 mmHg for about 20 h to give a white solid in anhydrous form (6.6 g, 73%). A portion of the compound is placed in a drying dish at 80-100% relative humidity (RH) and room temperature for about 24 h. The compound absorbed 5.8% water forming a dihydrate which is stable at room temperature and at 5-100% relative humidity (RH). $^1$H NMR (CDCl$_3$): δ 10.2 (bs, 1H), 8.26 (s, 1H), 6.80 (d, 2H, J=10.5 Hz), 5.79 (m, 1H), 4.13 (t, 2H, J=6.3 Hz), 3.03 (t, 2H, J=7.2 Hz), 2.57 (s, 3H), 2.35 (s, 4H), 2.07 (m, 2H), 1.27 (d, J=6.0, 3H).

This compound absorbs two mole waters at 5%-100% RH to become its dihydrate. 5-Chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate salt dihydrate.

Examples 3-21 and their hydrogen chloride salts are synthesized analogously to Example 1 and Example 1a.

EXAMPLE 3

5-Chloro-6-{2,6-difluoro-4-[3-(methylamino)propoxy]phenyl}-N-(2,2,2-trifluoroethyl)[1,2,4]triazolo[1,5-a]pyrimidin-7-amine; 451.2 (M+H)°

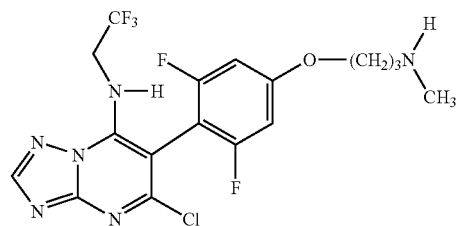

EXAMPLE 3a

5-Chloro-6-{2,6-difluoro-4-[3-(methylamino)propoxy]phenyl}-N-(2,2,2-trifluoroethyl)[1,2,4]triazolo[1,5-a]pyrimidin-7-amine hydrogen chloride Salt

EXAMPLE 4

5-Chloro-6-{4-[3-(dimethylamino)propoxy]-2,6-difluorophenyl}-N-(2,2,2-trifluoroethyl)[1,2,4]triazolo[1,5-a]pyrimidin-7-amine; 465.2 (M+H)

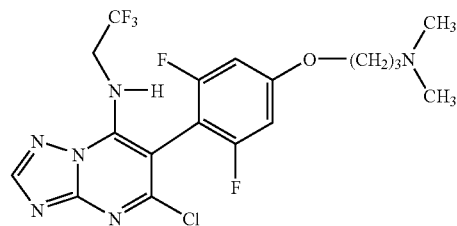

EXAMPLE 4a

5-Chloro-6-{4-[3-(dimethylamino)propoxy]-2,6-difluorophenyl}-N-(2,2,2-trifluoroethyl)[1,2,4]triazolo[1,5-a]pyrimidin-7-amine Hydrogen chloride Salt

EXAMPLE 5

6-[4-(3-Aminopropoxy)-2,6-difluorophenyl]-5-chloro-N-[(1S)-2,2,2-trifluoro-1-methylethyl][1,2,4]triazolo[1,5-a]pyrimidin-7-amine; 451.5 (M+H)

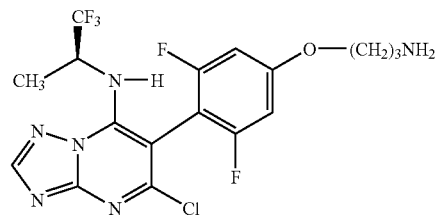

EXAMPLE 6

5-Chloro-6-{2,6-difluoro-4-[3-(4-methylpiperazin-1-yl)propoxy]phenyl}-N-[(1S)-2,2,2-trifluoro-1-methylethyl][1,2,4]triazolo[1,5-a]pyrimidin-7-amine; 534.4 (M+H)

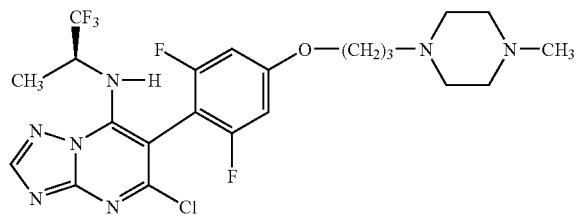

EXAMPLE 7

5-Chloro-6-{4-[3-(ethylamino)propoxy]-2,6-difluorophenyl}-N-[(1S)-2,2,2-trifluoro-1-methylethyl][1,2,4]triazolo[1,5-a]pyrimidin-7-amine; 479.1 (M+H)

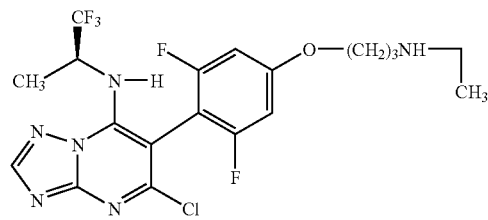

EXAMPLE 8

5-Chloro-6-(4-{3-[ethyl(methyl)amino]propoxy}-2,6-difluorophenyl)-N-[(1S)-2,2,2-trifluoro-1-methylethyl][1,2,4]triazolo[1,5-a]pyrimidin-7-amine; 493.0 (M+H)

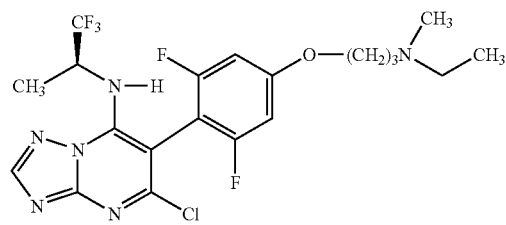

EXAMPLE 9

5-Chloro-6-[2,6-difluoro-4-(3-pyrrolidin-1-ylpropoxy)phenyl]-N-[(1S)-2,2,2-trifluoro-1-methylethyl][1,2,4]triazolo[1,5-a]pyrimidin-7-amine; 505.2 (M+H)

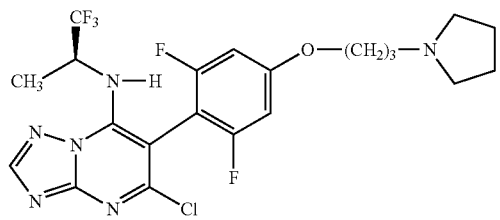

EXAMPLE 10

5-Chloro-6-[2,6-difluoro-4-(3-piperidin-1-ylpropoxy)phenyl]-N-[(1S)-2,2,2-trifluoro-1-methylethyl][1,2,4]triazolo[1,5-a]pyrimidin-7-amine; 519.3 (M+H)

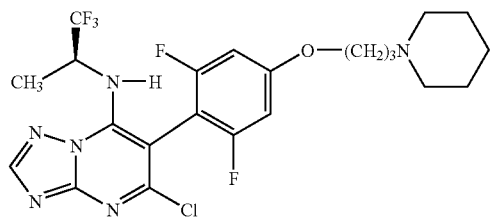

EXAMPLE 11

5-Chloro-6-[2,6-difluoro-4-(3-morpholin-4-ylpropoxy)phenyl]-N-[(1S)-2,2,2-trifluoro-1-methylethyl][1,2,4]triazolo[1,5-a]pyrimidin-7-amine; 521.1 (M+H)

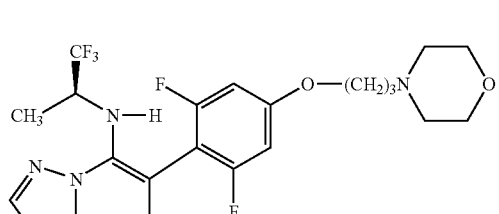

EXAMPLE 11a

5-Chloro-6-[2,6-difluoro-4-(3-morpholin-4-ylpropoxy)phenyl]-N-[(1S)-2,2,2-trifluoro-1-methylethyl][1,2,4]triazolo[1,5-a]pyrimidin-7-amine Hydrogen chloride

EXAMPLE 12

6-[4-(3-Azetidin-1-ylpropoxy)-2,6-difluorophenyl]-5-chloro-N-[(1S)-2,2,2-trifluoro-1-methylethyl][1,2,4]triazolo[1,5-a]pyrimidin-7-amine; 489.1 (M−H)

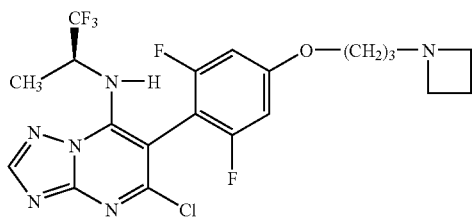

EXAMPLE 13

5-Chloro-6-{4-[3-(dimethylamino)propoxy]-2-fluorophenyl}-N-[(1S)-2,2,2-trifluoro-1-methylethyl][1,2,4]triazolo[1,5-a]pyrimidin-7-amine; 461.2 (M+H)

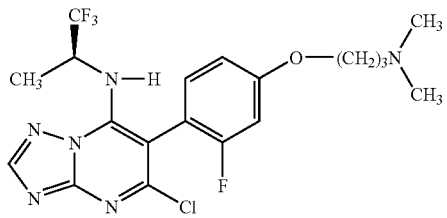

EXAMPLE 14

5-Chloro-6-{2,6-difluoro-4-[2-(methylamino)ethoxy]phenyl}-N-[(1S)-2,2,2-trifluoro-1-methylethyl][1,2,4]triazolo[1,5-a]pyrimidin-7-amine; 451.0 (M+H)

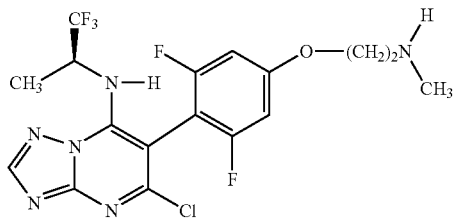

EXAMPLE 15

5-Chloro-6-{4-[4-(dimethylamino)butoxy]-2,6-difluorophenyl}-N-[(1S)-2,2,2-trifluoro-1-methylethyl][1,2,4]triazolo[1,5-a]pyrimidin-7-amine; 493.1 (M+H)

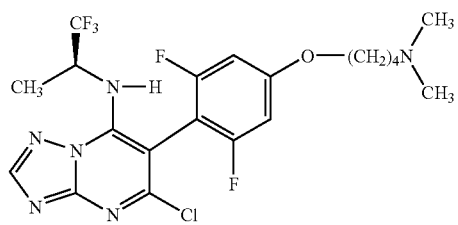

EXAMPLE 16

5-Chloro-6-{4-[2-(dimethylamino)ethoxy]-2,6-difluorophenyl}-N-[(1S)-2,2,2-trifluoro-1-methylethyl][1,2,4]triazolo[1,5-a]pyrimidin-7-amine; 465.1 (M+H)

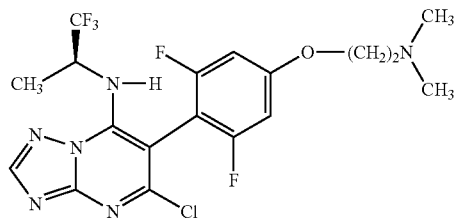

EXAMPLE 17

5-Chloro-6-[2,6-difluoro-4-(2-morpholin-4-ylethoxy)phenyl]-N-[(1S)-2,2,2-trifluoro-1-methylethyl][1,2,4]triazolo[1,5-a]pyrimidin-7-amine; 504.9 (M−H)

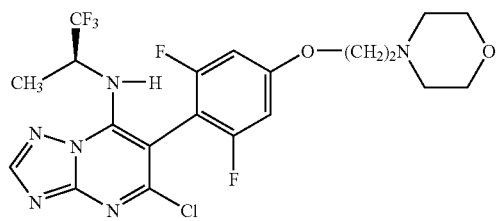

EXAMPLE 18

5-Chloro-6-(4-{[3-(dimethylamino)propyl]thio}-2,6-difluorophenyl)-N-[(1S)-2,2,2-trifluoro-1-methylethyl][1,2,4]triazolo[1,5-a]pyrimidin-7-amine; 495.2 (M+H)

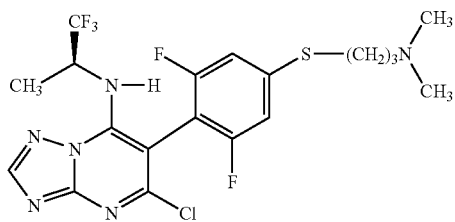

EXAMPLE 19

2-[4-(5-Chloro-7-{[(1S)-2,2,2-trifluoro-1-methylethyl]amino}[1,2,4]triazolo[1,5-a]pyrimidin-6-yl)-3,5-difluorophenoxy]ethanol; 438.1 (M+H)

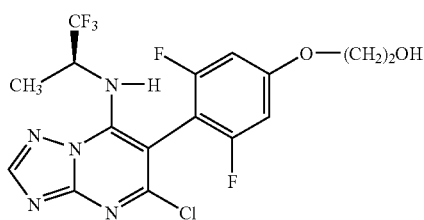

EXAMPLE 20

3-[4-(5-Chloro-7-{[(1S)-2,2,2-trifluoro-1-methylethyl]amino}[1,2,4]triazolo[1,5-a]pyrimidin-6-yl)-3,5-difluorophenoxy]propan-1-ol; 452.1 (M+H)

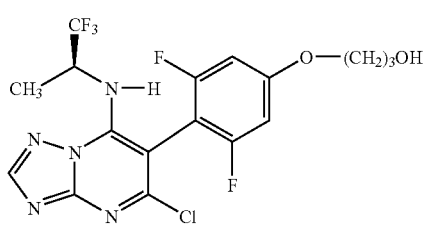

EXAMPLE 21

4-[4-(5-Chloro-7-{[(1S)-2,2,2-trifluoro-1-methylethyl]amino}[1,2,4]triazolo[1,5-a]pyrimidin-6-yl)-3,5-difluorophenoxy]butan-1-ol; 463.9 (M−H)

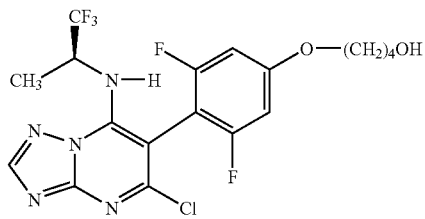

EXAMPLE 22

$N^1$-[4-(5-Chloro-7-{[(1S)-2,2,2-trifluoro-1-methylethyl]amino}[1,2,4]triazolo[1,5-a]pyrimidin-6-yl)-3,5-difluorophenyl]-N',$N^3$,$N^3$-trimethylpropane-1,3-diamine; 492.1 (M+H)

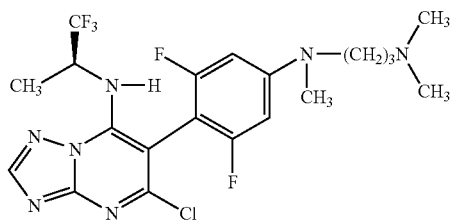

To a mixture of 5-chloro-6-(2,4,6-trifluorophenyl)-N-[(1S)-2,2,2-trifluoro-1-methylethyl][1,2,4]triazolo[1,5-a]pyrimidin-7-amine (200 mg, 0.51 mmol) in N,N,N'-trimethyl-1,3-propanediamine (3.0 g, 25.8 mmol) is added sodium hydride (100 mg, 2.5 mmol). The resulting mixture is heated at 100° C. for 16 h. The reaction is then quenched with water and extracted with ethyl acetate (x2). The combined organic extracts are washed with saturated sodium chloride, dried over magnesium sulfate, and concentrated to a residue. The residue is chromatographed over silica gel, eluting with a gradient of 100% ethyl acetate to 50% methyl alcohol in ethyl acetate to 100% methyl alcohol. Concentration provides $N^1$-[4-(5-chloro-7-{[(1S)-2,2,2-trifluoro-1-methylethyl]amino}[1,2,4]triazolo[1,5-a]pyrimidin-6-yl)-3,5-difluorophenyl]-N',$N^3$,$N^3$-trimethylpropane-1,3-diamine (20 mg) as a yellow oil. MS: m/z 492.1 (M+H).

Examples 23-24 are synthesized analogously to Example 22.

EXAMPLE 23

N¹-[4-(5-Chloro-7-{[(1S)-2,2,2-trifluoro-1-methylethyl]amino}[1,2,4]triazolo[1,5-a]pyrimidin-6-yl)-3,5-difluorophenyl]-N³,N³-dimethylpropane-1,3-diamine; 478.2 (M+H)

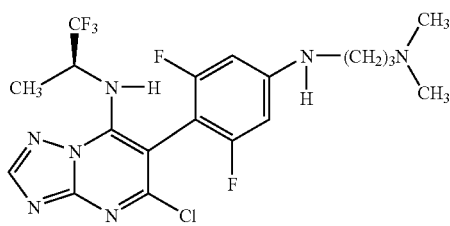

EXAMPLE 24

N¹-[4-(5-Chloro-7-{[(1S)-2,2,2-trifluoro-1-methylethyl]amino}[1,2,4]triazolo[1,5-a]pyrimidin-6-yl)-3,5-difluorophenyl]-N²,N²-dimethylethane-1,2-diamine; 464.1 (M+H)

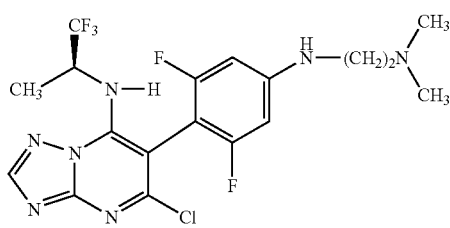

EXAMPLE 25

5-Bromo-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine

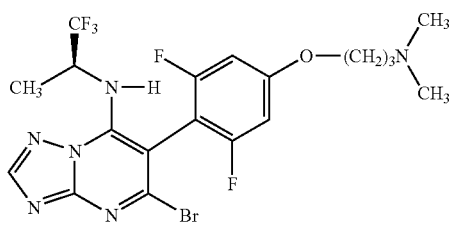

Step A: 5,7-Dibromo-6-(2,4,6-trifluorophenyl)[1,2,4]triazolo[1,5-a]pyrimidine

A mixture of 5,7-dihydroxy-6-(2,4,6-trifluorophenyl)[1,2,4]triazolo[1,5-a]pyrimidine (282 mg, 1.0 mmol) and phosphorus oxybromide (2.0 g, 7.0 mmol) is heated at 120° C. for 4 h. Excess phosphorus oxybromide is then removed in vaccuo. The residue is dissolved in methylene cholride and washed with water and saturated sodium chloride (x3). The organic layer is dried over magnesium sulfate, filtered through hydrous magnesium silicate, and concentrated. 5,7-Dibromo-6-(2,4,6-trifluorophenyl)[1,2,4]triazolo[1,5-a]pyrimidine is obtained as a tan semi-solid (380 mg). It is used directly in the next step without further purification. MS: m/Z 408.9 (M+H).

Step B: 5-Bromo-6-(2,4,6-trifluorophenyl)-N-[(1S)-2,2,2-trifluoro-1-methylethyl][1,2,4]triazolo[1,5-a]pyrimidin-7-amine A mixture of 5,7-dibromo-6-(2,4,6-trifluorophenyl)[1,2,4]triazolo[1,5-a]pyrimidine (320 mg, 0.78 mmol), (1S)-2,2,2-trifluoro-1-methylethylamine hydrogen chloride (235 mg, 1.57 mmol), and diisopropylethylamine (260 mg, 2.0 mmol) in 5 mL of N,N-dimethylformamide is stirred at room temperature for 18 h. Water is added to quench the reaction, and the product is extracted with ethyl acetate. The combined organic extracts are washed with saturated sodium chloride (x3), dried over magnesium sulfate, and concentrated to a residue. The residue is chromatographed over silica gel, eluting with a gradient of 9:1 hexanes/ethyl acetate to 2:1 hexanes/ethyl acetate. Concentration provides 5-bromo-6-(2,4,6-trifluorophenyl)-N-[(1S)-2,2,2-trifluoro-1-methylethyl][1,2,4]triazolo[1,5-a]pyrimidin-7-amine as a light tan solid (60 mg, mp 95-97° C.). MS: m/z 440.0, 442.0 (M+H).

Step C: 5-Bromo-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine To a solution of 5-bromo-6-(2,4,6-trifluorophenyl)-N-[(1S)-2,2,2-trifluoro-1-methylethyl][1,2,4]triazolo[1,5-a]pyrimidin-7-amine (44 mg, 0.1 mmol) and 3-dimethylamino-1-propanol (51 m g, 0.5 mmol) in 1 mL of dimethylsulfoxide at room temperature is added sodium hydride (60% in mineral oil, 20 mg, 0.5 mmol). The mixture is heated at 60° C. for 2 h, and cooled to room temperature. Water is added to quench the reaction, and the product is extracted with ethyl acetate. The organic layer is washed with saturated sodium chloride (x3), dried over magnesium sulfate, and concentrated to a residue. The residue is chromatographed over silica gel, eluting with a gradient of ethyl acetate to 30% methyl alcohol in ethyl acetate. Concentration provides 5-bromo-6-{4-[3-(dimethylamino)propoxy]-2,6-difluorophenyl}-N-[(1S)-2,2,2-trifluoro-1-methylethyl][1,2,4]triazolo[1,5-a]pyrimidin-7-amine as a light tan solid (41 mg, mp 40-42° C.). MS: m/z 523.1, 525.1 (M+H).

EXAMPLE 26

5-Chloro-6-{4-[4-(dimethylamino)butyl]-2,6-difluorophenyl}-N-[(1S)-2,2,2-trifluoro-1-methylethyl][1,2,4]triazolo[1,5-a]pyrimidin-7-amine;

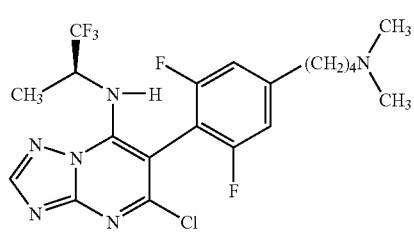

Step A: Diethyl 2-(2,6-difluoro-4-hydroxyphenyl)malonate

To a solution of diethyl 2-(2,6-difluoro-4-methoxyphenyl)malonate (2.11 g, 7.0 mmol) in 60 mL of methylene chloride at −78° C. is added boron tribromide (2.65 mL, 28 mmol) dropwise. The mixture is then stirred at −78° C. for 10 minutes, warmed to 0° C., and stirred at 0° C. for 1 h. A 5% aqueous solution of sodium bicarbonate is added slowly to quench the reaction. The product is extracted with ethyl acetate. The combined organic extracts are washed with saturated sodium chloride, dried over magnesium sulfate, and concentrated to a residue. The residue is chromatographed over silica gel, eluting with a gradient of 10% ethyl acetate in hexanes to 30% ethyl acetate in hexanes. Concentration provides diethyl 2-(2,6-difluoro-4-hydroxyphenyl)malonate as a colorless oil (1.91 g). MS: m/z 287.2 (M−H).

Step B: Diethyl 2-(2,6-difluoro-4-{[(trifluoromethyl)sulfonyl]oxy}phenyl)malonate To a solution of diethyl 2-(2,6-difluoro-4-hydroxyphenyl)malonate (288 mg, 1.0 mmol) and triethylamine (505 mg, 5.0 mmol) in 5 mL of methylene chloride at room temperature is added trifluoromethanesulfonic anhydride (1.41 g, 5.0 mmol). The mixture is stirred at room temperature for 10 minutes. A 5% aqueous solution of sodium bicarbonate is added slowly to quench the reaction. The product is extracted with ethyl acetate. The combined organic extracts are washed with saturated sodium chloride, dried over magnesium sulfate, and concentrated to a residue. The residue is chromatographed over silica gel, eluting with a gradient of hexanes to 15% ethyl acetate in hexanes. Concentration provides diethyl 2-(2,6-difluoro-4-{[(trifluoromethyl)sulfonyl]oxy}phenyl)malonate as a colorless oil (361 mg). MS: m/z 419.2 (M−H).

Step C: Diethyl 2-[2,6-difluoro-4-(4-hydroxybutyl)phenyl]malonate

To a 0.5 M solution of 9-borabicyclo[3.3.1]nonane (9-BBN) in tetrahydrofuran (95 mL, 47.6 mmol) is added dropwise 3-butene-1-ol (4.1 mL, 47.6 mmol), and the mixture is stirred under nitrogen atmosphere at room temperature for 6 h. The resulting solution is then transferred by a double-ended needle into a mixture of diethyl 2-(2,6-difluoro-4-{[(trifluoromethyl)sulfonyl]oxy}phenyl)malonate (10.0 g, 23.8 mmol), potassium phosphate (10.1 g, 47.6 mmol), and tetrakis(triphenylphosphine)palladium(0) (825 mg, 0.714 mmol) in 40 mL of dioxane under nitrogen pressure. The mixture is then heated at 90° C. for 8 h. The reaction is cooled to room temperature, and trimethylamine-N-oxide (3.57 g, 47.6 mmol) is added. The reaction is heated at 80° C. for 1 h and cooled to room temperature. Ethyl acetate is added to dilute the reaction. The organic phase is washed with saturated sodium chloride (x2), dried over magnesium sulfate, and concentrated to a residue. The residue is chromatographed over silica gel, eluting with a gradient of 10% ethyl acetate in hexanes to 50% ethyl acetate in hexanes. Concentration provides diethyl 2-[2,6-difluoro-4-(4-hydroxybutyl)phenyl]malonate as a brown oil (3.5 g). MS: m/z 345.2 (M+H).

Step D: Diethyl 2-{4-[4-(dimethylamino)butyl]-2,6-difluorophenyl}malonate

To a solution of 2-[2,6-difluoro-4-(4-hydroxybutyl)phenyl]malonate (2.0 g, 5.8 mmol) and triethylamine (2.43 mL, 17.4 mmol) in 15 ml of methylene chloride at 0° C. is added methanesulfonyl chloride (0.898 mL, 11.6 mmol). The resulting mixture is allowed to warm to room temperature in 1.5 h. The mixture is washed with 10% hydrochloric acid, saturated sodium bicarbonate, and saturated sodium chloride. The organic layer is dried over magnesium sulfate and concentrated to a yellow oil. The yellow oil thus obtained is stirred with 2.0 M diethylamine in tetrahydrofuran (56 mL, 112 mmol) at room temperature for 16 h, followed by concentration. The residue is diluted with ethyl acetate. The organic layer is washed with water and saturated sodium chloride, dried over magnesium sulfate, and concentrated to a residue. The residue is chromatographed over silica gel, eluting with a gradient of 100% ethyl acetate to 50% methyl alcohol in ethyl acetate to 100% methyl alcohol. Concentration provides diethyl 2-{4-[4-(dimethylamino)butyl]-2,6-difluorophenyl}malonate as a yellow oil (1.2 g). MS: m/z 372.2 (M+H).

Step E: 6-{4-[4-(Dimethylamino)butyl]-2,6-difluorophenyl}[1,2,4]triazolo[1,5-a]pyrimidine-5,7-diol A mixture of diethyl 2-{4-[4-(dimethylamino)butyl]-2,6-difluorophenyl]malonate (1.0 g, 2.7 mmol), 3-amino-1,2,4-triazole (250 mg, 3.0 mmol), and tributylamine (0.71 mL, 3.0 mmol) is stirred under nitrogen atmosphere at 160° C. for 16 h and cooled to room temperature. The mixture is stirred with 20 ml of hexanes. The precipitates are collected by filtration, washed with hexanes to give 6-{4-[4-(dimethylamino)butyl]-2,6-difluorophenyl}[1,2,4]triazolo[1,5-a]pyrimidine-5,7-diol as a white solid (795 mg). MS: m/z 362.1 (M−H).

Step F: 5-Chloro-6-{4-[4-(dimethylamino)butyl]-2,6-difluorophenyl}-N-[(1S)-2,2,2-trifluoro-1-methylethyl][1,2,4]triazolo[1,5-a]pyrimidin-7-amine A mixture of 6-{4-[4-(dimethylamino)butyl]-2,6-difluorophenyl}[1,2,4]triazolo[1,5-a]pyrimidine-5,7-diol (795 mg, 2.19 mmol) in 4 mL of phosphorous oxychloride is heated at 115° C. for 4 h. The excess phosphorous oxychloride is removed in vaccuo, and the resulting residue is dried further under high vacuum to give a yellow solid (1.13 g) which is used without further purification.

A mixture of the above solid (300 mg, 0.75 mmol), (1S)-2,2,2-trifluoro-1-methylethylamine hydrogen chloride (675 mg, 4.51 mmol), and N,N-diisopropylethylamine (0.787 mL, 4.51 mmol) in 4 mL of N,N-dimethylformamide is stirred at room temperature for 18 h. The reaction mixture is diluted with ethyl acetate. The organic layer is washed with saturated sodium bicarbonate and saturated sodium chloride, dried over magnesium sulfate, and concentrated to a residue. The residue is chromatographed over silica gel, eluting with a gradient of 100% ethyl acetate to 50% methyl alcohol in ethyl acetate to 100% methyl alcohol. Concentration provides 5-chloro-6-{4-[4-(dimethylamino)butyl]-2,6-difluorophenyl}-N-[(1S)-2,2,2-trifluoro-1-methylethyl][1,2,4]triazolo[1,5-a]pyrimidin-7-amine as a light yellow oil (44 mg). MS: m/z 477.2 (M+H).

Examples 27-29 are synthesized analogously to Example 1, starting from 5-chloro-6-(2,3,6-trifluorophenyl)-N-[(1S)-2,2,2-trifluoro-1-methylethyl][1,2,4]triazolo[1,5-a]pyrimidin-7-amine

EXAMPLE 27

5-Chloro-6-{3-[2-(dimethylamino)ethoxy]-2,6-difluorophenyl}-N-[(1S)-2,2,2-trifluoro-1-methylethyl][1,2,4]triazolo[1,5-a]pyrimidin-7-amine; 465.1 (M+H)

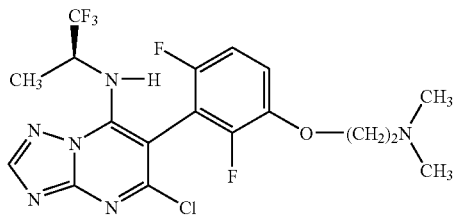

EXAMPLE 28

5-Chloro-6-{3-[3-(dimethylamino)propoxy]-2,6-difluorophenyl}-N-[(1S)-2,2,2-trifluoro-1-methylethyl][1,2,4]triazolo[1,5-a]pyrimidin-7-amine; 479.1 (M+H)

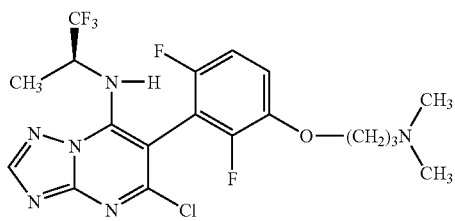

EXAMPLE 29

5-Chloro-6-{3-[4-(dimethylamino)butoxy]-2,6-difluorophenyl}-N-[(1S)-2,2,2-trifluoro-1-methylethyl][1,2,4]triazolo[1,5-a]pyrimidin-7-amine; 493.1 (M+H)

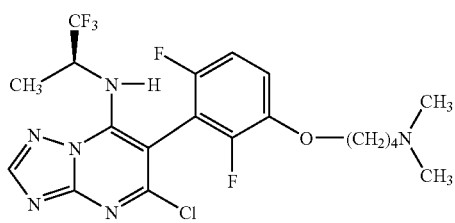

EXAMPLE 30

3-[4-(5-Chloro-7-cycloheptyl[1,2,4]triazolo[1,5-a]pyrimidin-6-yl)-3,5-difluorophenoxy]propan-1-ol;

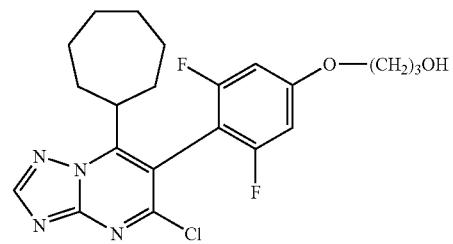

Step A: Ethyl 3-cycloheptyl-3-oxo-2-(2,4,6-trifluorophenyl)propanoate

A mixture of 2,4,6-trifluorophenylacetic acid (570 mg, 3.0 mmol), iodoethane (1.56 g, 10 mmol), and potassium carbonate (1.38 g, 10 mmol) in 5 mL of dimethylsulfoxide is stirred at 50° C. for 3 h, and cooled to room temperature. The mixture is partitioned between diethyl ether and water. The organic layer is washed with water and saturated sodium chloride, dried over magnesium sulfate, and filtered through hydrous magnesium silicate. The filtrate is concentrated to give ethyl 2,4,6-trifluorophenylacetate as a light yellow oil (581 mg, 2.66 mmol).

A mixture of cycloheptanecarboxylic acid (5.0 g, 35.2 mmol) in 25 mL of thionyl chloride is refluxed for 1 h, and concentrated. The crude cycloheptanecarboxylic acid chloride thus obtained is used directly in the next step.

A solution of ethyl 2,4,6-trifluorophenylacetate (436 mg, 2.0 mmol) in 3 mL of tetrahydrofuran is cooled to −78° C., and lithium diisopropylamide (2.0 M in heptane/tetrahydrofuran/ethylbenzene, 1.0 mL, 2.0 mmol) is added dropwise with stirring. The mixture is stirred at −78° C. for 1 h, and cycloheptanecarboxylic acid chloride (321 mg, 2.0 mmol) is added dropwise. The mixture is warmed to room temperature and acidified with 2 mL of 1.0 N hydrochloric acid. The product is extracted with ethyl acetate. The organic layer is washed with saturated sodium chloride, dried over magnesium sulfate, and concentrated to a residue. The residue is chromatographed over silica gel, eluting with a gradient of hexanes to 10% ethyl acetate in hexanes. Concentration provides ethyl 3-cycloheptyl-3-oxo-2-(2,4,6-trifluorophenyl)propanoate as a colorless oil (410 mg). MS: m/z 341.2 (M−H).

Step B: 7-Cycloheptyl-6-(2,4,6-trifluorophenyl)[1,2,4]triazolo[1,5-a]pyrimidin-5-ol;

A mixture of ethyl 3-cycloheptyl-3-oxo-2-(2,4,6-trifluorophenyl)propanoate (342 mg, 1.0 mmol), 3-amino-1,2,4-triazole (84 mg, 1.0 mmol), and tributylamine (185 mg, 1.0 mmol) is stirred under nitrogen atmosphere at 160° C. for 2.5 h and cooled to room temperature. The mixture is dissolved in ethyl acetate and the organic layer is washed with 1.0 N hydrochloric acid and saturated sodium chloride, dried over magnesium sulfate, and concentrated to a solid. The solid thus obtained is washed with hexanes to give crude 7-cycloheptyl-6-(2,4,6-trifluorophenyl)[1,2,4]triazolo[1,5-a]pyrimidin-5-ol as a light tan solid (225 mg). MS: m/z 363.2 (M+H).

Step C: 5-Chloro-7-cycloheptyl-6-(2,6-difluoro-4-{3-[(4-methoxybenzyl)oxy]propoxy}phenyl)[1,2,4]triazolo[1,5-a]pyrimidine;

To a solution of 7-cycloheptyl-6-(2,4,6-trifluorophenyl)[1,2,4]triazolo[1,5-a]pyrimidin-5-ol (362 mg, 1.0 mmol) and 3-[(4-methoxybenzyl)oxy]-1-propanol (490 mg, 2.5 mmol) in 4.0 mL of dimethylsulfoxide at room temperature is added sodium hydride (60% in mineral oil, 120 mg, 3.0 mmol). The mixture is stirred at room temperature for 3 h, and partitioned between ethyl acetate and 1.0 N hydrochloric acid. The organic solution is washed with saturated sodium chloride, dried over magnesium sulfate, and concentrated to a residue. The residue is chromatographed over silica gel, eluting with a gradient of 66% ethyl acetate in hexanes to 5% methyl alcohol in ethyl acetate. Concentration provides 7-cycloheptyl-6-(2,6-difluoro-4-{3-[(4-methoxybenzyl)oxy]propoxy}phenyl)[1,2,4]triazolo[1,5-a]pyrimidin-5-ol as a yellow oil (820 mg).

To the above 7-cycloheptyl-6-(2,6-difluoro-4-{3-[(4-methoxybenzyl)oxy]propoxy}phenyl)[1,2,4]triazolo[1,5-a]pyrimidin-5-ol (820 mg) is added 5 mL of phosphorous oxychloride and 2 mL of N,N-diethylaniline, and the mixture is heated at reflux for 1 h. The excess phosphorous oxychloride is removed in vaccuo, and the resulting residue is partitioned between methylene chloride and 1 N hydrochloric acid. The organic layer is washed with saturated sodium chloride, dried over magnesium sulfate, and concentrated to a residue. The residue is chromatographed over silica gel, eluting with a gradient of hexanes to 20% ethyl acetate in hexanes. Concentration provides 5-chloro-7-cycloheptyl-6-(2,6-difluoro-4-{3-[(4-methoxybenzyl)oxy]propoxy}phenyl)[1,2,4]triazolo[1,5-a]pyrimidine as a yellow oil (180 mg). MS: m/z 557.2 (M+H).

Step D: 3-[4-(5-Chloro-7-cycloheptyl[1,2,4]triazolo[1,5-a]pyrimidin-6-yl)-3,5-difluorophenoxy]propan-1-ol;

To a solution of 5-chloro-7-cycloheptyl-6-(2,6-difluoro-4-{3-[(4-methoxybenzyl)oxy]propoxy}phenyl)[1,2,4]triazolo[1,5-a]pyrimidine (56 mg, 0.1 mmol) in 4 mL of methylene chloride and 0.2 mL of water is added 2,3-dichloro-5,6-dicyano-1,4-bezoquinone (100 mg, 0.44 mmol). The mixture is stirred at room temperature for 20 minutes, then washed with saturated aqueous sodium bicarbonate solution (x2), dried over magnesium sulfate, and concentrated to a residue. The residue is chromatographed over silica gel, eluting with a gradient of 33% ethyl acetate in hexanes to 66% ethyl acetate in hexanes. Concentration provides 3-[4-(5-chloro-7-cycloheptyl[1,2,4]triazolo[1,5-a]pyrimidin-6-yl)-3,5-difluorophenoxy]propan-1-ol as a light yellow solid (34 mg). MS: m/z 437.2 (M+H).

EXAMPLE 31

3-[4-(5-Chloro-7-cycloheptyl[1,2,4]triazolo[1,5-a]pyrimidin-6-yl)-3,5-difluorophenoxy]-N,N-dimethylpropan-1-amine;

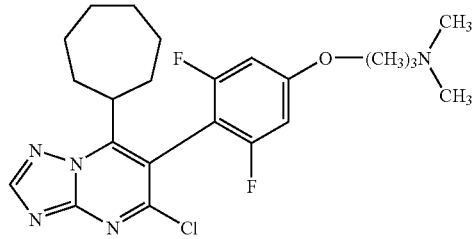

To a solution of 7-cycloheptyl-6-(2,4,6-trifluorophenyl)[1,2,4]triazolo[1,5-a]pyrimidin-5-ol (396 mg, 1.1 mmol) and 3-dimethylamino-1-propanol (561 mg, 5.5 mmol) in 5 mL of dimethylsulfoxide at room temperature is added sodium hydride (60% in mineral oil, 200 mg, 5 mmol). The mixture is stirred at room temperature for 3 h, and partitioned between ethyl acetate and water. The aqueous layer is neutralized with 1 N hydrochloric acid to pH 0.8. Some of the desired product precipitates out of solution, and is obtained by filtration. The organic solution is washed with saturated sodium chloride, dried over magnesium sulfate, and concentrated to a residue. The residue is combined with the solid product to provide crude 7-cycloheptyl-6-{4-[3-(dimethylamino)propoxy-2,6-difluorophenyl}[1,2,4]triazolo[1,5-a]pyrimidin-5-ol. MS: m/z 446.1 (M+H).

To the above crude 7-cycloheptyl-6-{4-[3-(dimethylamino)propoxy-2,6-difluorophenyl}[1,2,4]triazolo[1,5-a]pyrimidin-5-ol is added 2 mL of phosphorous oxychloride and 1 mL of N,N-diethylaniline, and the mixture is heated at 110° C. for 1 h. The excess phosphorous oxychloride is removed in vaccuo, and the resulting residue is partitioned between ethyl acetate and 5% aqueous sodium carbonate solution. The organic layer is washed with saturated sodium chloride, dried over magnesium sulfate, and concentrated to a residue. The residue is chromatographed over silica gel, eluting with a gradient of methylene chloride to 20% methyl alcohol in methylene chloride. Concentration provides 3-[4-(5-chloro-7-cycloheptyl[1,2,4]triazolo[1,5-a]pyrimidin-6-yl)-3,5-difluorophenoxy]-N,N-dimethylpropan-1-amine as a tan solid (105 mg). MS: m/z 464.0 (M+H).

EXAMPLE 32

3-[4-(5-Chloro-7-cycloheptyl[1,2,4]triazolo[1,5-a]pyrimidin-6-yl)-3,5-difluorophenoxy]-N-methylpropan-1-amine trifluoroacetic acid salt

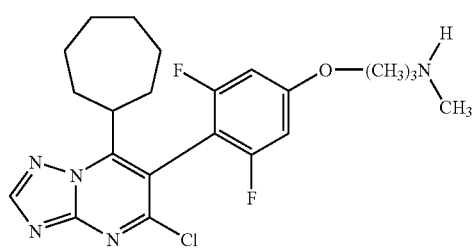

Step A: tert-Butyl 3-[4-(7-Cycloheptyl-5-hydroxy[1,2,4]triazolo[1,5-a]pyrimidin-6-yl)-3,5-difluorophenoxy]propyl(methyl)carbamate;

To a mixture of sodium hydride (60% in mineral oil, 334 mg, 8.35 mmol) in 10 mL of dimethylsulfoxide at room temperature is added 3-(methylamino)propan-1-ol (744 mg, 8.35 mmol). The mixture is stirred at room temperature for 1 h, and a solution of 7-cycloheptyl-6-(2,4,6-trifluorophenyl)[1,2,4]triazolo[1,5-a]pyrimidin-5-ol (1.12 g, 3.1 mmol) in 10 mL of dimethylsulfoxide is added. The mixture is stirred at room temperature for 6 h, and a solution of di-tert-butyl dicarbonate (1.82 g, 8.35 mmol) in 10 mL of dimethylsulfoxide is added. The mixture is stirred at room temperature for 18 h and diluted with ethyl acetate. The organic layer is washed with water (x2) and saturated sodium chloride, dried over magnesium sulfate, and concentrated to a residue. The residue is chromatographed over silica gel, eluting with a gradient of 30% ethyl acetate in hexanes to 70% ethyl acetate in hexanes. Concentration provides tert-butyl 3-[4-(7-cycloheptyl-5-hydroxy[1,2,4]triazolo[1,5-a]pyrimidin-6-yl)-3,5-difluorophenoxy]propyl(methyl)carbamate as a yellow solid (876 mg). MS: m/z 530.4 (M–H).

Step B: tert-Butyl 3-[4-(5-chloro-7-cycloheptyl [1,2,4]triazolo[1,5-a]pyrimidin-6-yl)-3,5-difluorophenoxy]propyl(methyl)carbamate;

To tert-butyl 3-[4-(7-cycloheptyl-5-hydroxy[1,2,4]triazolo[1,5-a]pyrimidin-6-yl)-3,5-difluorophenoxy]propyl(methyl)carbamate (876 mg, 1.64 mmol) is added 5.8 mL of phosphorous oxychloride and 2.9 mL of N,N-diethylaniline, and the mixture is heated at 90° C. for 3 h. The excess phosphorous oxychloride is removed in vaccuo, and the resulting residue is diluted with ethyl acetate. The organic layer is washed with ice water and saturated sodium chloride (x2), dried over magnesium sulfate, and concentrated to a residue. The residue is chromatographed over silica gel, eluting with a gradient of hexanes to 40% ethyl acetate in hexanes. Concentration provides tert-butyl 3-[4-(5-chloro-7-cycloheptyl [1,2,4]triazolo[1,5-a]pyrimidin-6-yl)-3,5-difluorophenoxy]propyl(methyl)carbamate as a light yellow oil (452 mg). MS: m/z 550.1 (M+H).

Step C: 3-[4-(5-Chloro-7-cycloheptyl[1,2,4]triazolo[1,5-a]pyrimidin-6-yl)-3,5-difluorophenoxy]-N-methylpropan-1-amine;

To a solution of tert-butyl 3-[4-(5-chloro-7-cycloheptyl[1,2,4]triazolo[1,5-a]pyrimidin-6-yl)-3,5-difluorophenoxy]propyl(methyl)carbamate (452 mg, 0.82 mmol) in 4 mL of methylene chloride is added 2.3 mL of trifluoroacetic acid. The mixture is stirred at room temperature for 18 h, and concentrated in vaccuo, yielding 3-[4-(5chloro-7-cycloheptyl[1,2,4]triazolo[1,5-a]pyrimidin-6-yl)-3,5-difluorophenoxy]-N-methylpropan-1-amine as a trifluoroacetic acid salt as a yellow semi-solid (400 mg). MS: m/z 450.2 (M+H).

EXAMPLE 33

5-Chloro-6-{2,6-difluoro-4-[3-(methylamino)propoxy]phenyl}-N-[(1R)-2,2,2-trifluoro-1-methylethyl][1,2,4]triazolo[1,5-a]pyrimidin-7-amine; 465.2 (M+H)

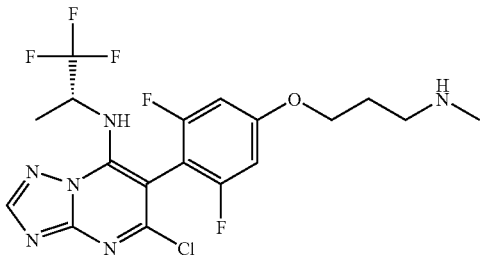

The product, 5-chloro-6-{2,6-difluoro-4-[3-(methylamino)propoxy]phenyl}-N-[(1R)-2,2,2-trifluoro-1-methylethyl][1,2,4]triazolo[1,5-a]pyrimidin-7-amine is synthesized using the conditions of Example 1 and replacing (1S)-2,2,2-trifluoro-1-methylethylamine hydrogen chloride with (1R)-2,2,2-trifluoro-1-methylethylamine hydrogen chloride Examples 34-37 may be synthesized analogously to Example 30.

EXAMPLE 34

3-[4-(5-Chloro-7-cyclooctyl[1,2,4]triazolo[1,5-a]pyrimidin-6-yl)-3,5-difluorophenoxy]propan-1-ol

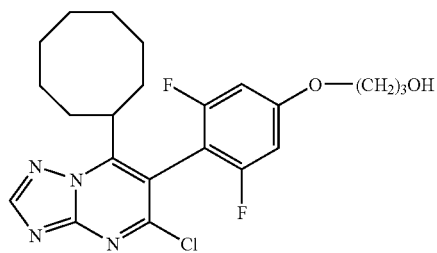

The product of the Example may be synthesized using the conditions of Example 30 and replacing cycloheptanecarboxylic acid with cyclooctanecarboxylic acid.

EXAMPLE 35

3-[4-(5-Chloro-7-cyclohexyl[1,2,4]triazolo[1,5-a]pyrimidin-6-yl)-3,5-difluorophenoxy]propan-1-ol;

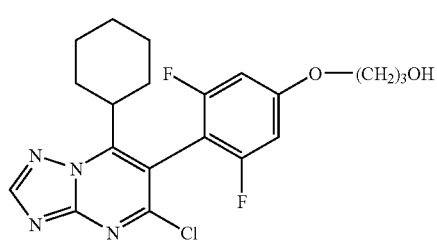

The product of the Example may be synthesized using the conditions of Example 30 and replacing cycloheptanecarboxylic acid with cyclohexanecarboxylic acid.

EXAMPLE 36

2-[4-(5-Chloro-7-cycloheptyl[1,2,4]triazolo[1,5-a]pyrimidin-6-yl)-3,5-difluorophenoxy]ethanol

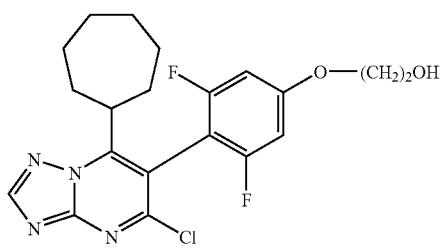

The product of the Example may be synthesized using the conditions of Example 30 and replacing 1,3-propanediol with ethylene glycol.

EXAMPLE 37

4-[4-(5-Chloro-7-cycloheptyl[1,2,4]triazolo[1,5-a]pyrimidin-6-yl)-3,5-difluorophenoxy]butan-1-ol The product of the Example may be synthesized using the conditions of Example 30 and replacing 1,3-propanediol with 1,4-butanediol.

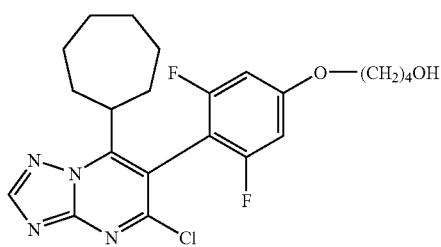

Examples 38-41 may be synthesized analogously to Example 31.

EXAMPLE 38

N-{3-[4-(5-Chloro-7-cyclooctyl[1,2,4]triazolo[1,5-a]pyrimidin-6-yl)-3,5-difluorophenoxy]propyl}-N,N-dimethylamine

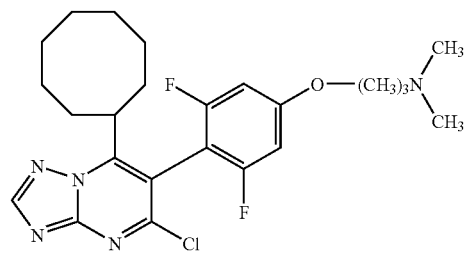

The product of the Example may be synthesized using the conditions of Example 31, and replacing cycloheptanecarboxylic acid with cyclooctanecarboxylic acid.

EXAMPLE 39

N-{3-[4-(5-Chloro-7-cyclohexyl[1,2,4]triazolo[1,5-a]pyrimidin-6-yl)-3,5-difluorophenoxy]propyl}-N,N-dimethylamine

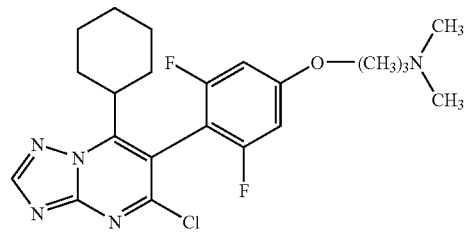

The product of the Example may be synthesized using the conditions of Example 31 and replacing cycloheptanecarboxylic acid with cyclohexanecarboxylic acid.

EXAMPLE 40

N{2-[4-(5-Chloro-7-cycloheptyl[1,2,4]triazolo[1,5-a]pyrimidin-6-yl)-3,5-difluorophenoxy]ethyl}-N,N-dimethylamine

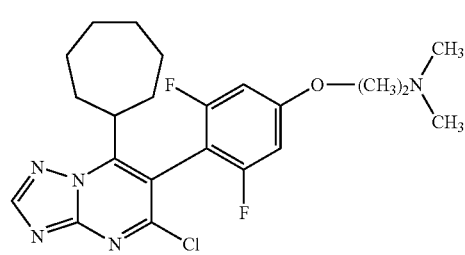

The product of the Example may be synthesized using the conditions of Example 31 and replacing 3-dimethylamino-1-propanol with 2-(dimethylamino)ethanol.

EXAMPLE 41

N-{4-[4-(5-Chloro-7-cycloheptyl[1,2,4]triazolo[1,5-a]pyrimidin-6-yl)-3,5-difluorophenoxy]butyl}-N,N-dimethylamine)

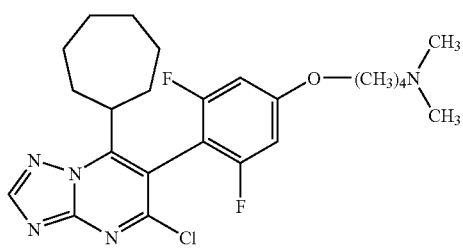

The product of the Example may be synthesized using the conditions of Example 31 replacing 3-dimethylamino-1-propanol with 4-(dimethylamino)-1-butanol.

Examples 42-45 may be synthesized analogously to Example 32.

EXAMPLE 42

N-{3-[4-(5-Chloro-7-cyclooctyl[1,2,4]triazolo[1,5-a]pyrimidin-6-yl)-3,5-difluorophenoxy]propyl}-N-methylamine

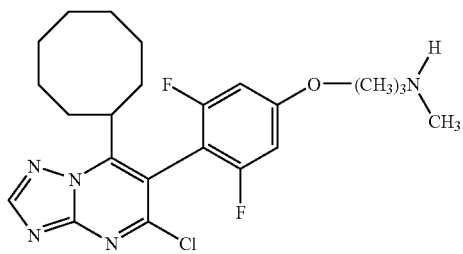

The product of the Example may be synthesized using the conditions of Example 32 replacing cycloheptanecarboxylic acid with cyclooctanecarboxylic acid.

EXAMPLE 43

N-{3-[4-(5-Chloro-7-cyclohexyl[1,2,4]triazolo[1,5-a]pyrimidin-6-yl)-3,5-difluorophenoxy]propyl}-N-methylamine

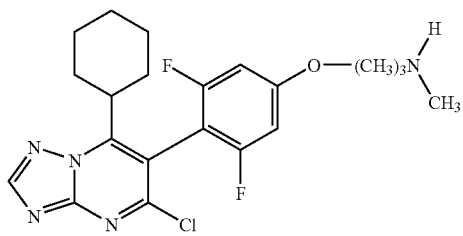

The product of the Example may be synthesized using the conditions of Example 32 replacing cycloheptanecarboxylic acid with cyclohexanecarboxylic acid.

EXAMPLE 44

N-{2-[4-(5-Chloro-7-cycloheptyl[1,2,4]triazolo[1,5-a]pyrimidin-6-yl)-3,5-difluorophenoxy]ethyl}-N-methylamine

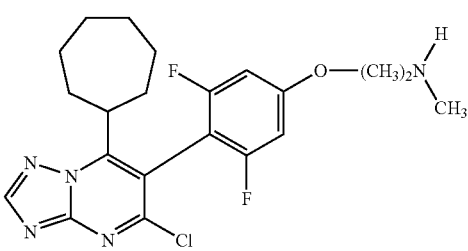

The product of the Example may be prepared using the conditions of Example 32 replacing 3-(methylamino)propan-1-ol with 2-(methylamino)ethanol.

EXAMPLE 45

N-{4-[4-(5-Chloro-7-cycloheptyl[1,2,4]triazolo[1,5-a]pyrimidin-6-yl)-3,5-difluorophenoxy]butyl}-N-methylamine)

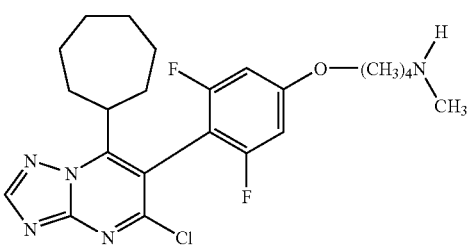

The product of the Example may be prepared using the conditions of Example 32 replacing 3-(methylamino)propan-1-ol with 4-(methylamino)-1-butanol.

Powder XRD measurement indicates that the anhydrous and hydrated 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine succinate salt (Example 2c) and the anhydrous and hydrated 5-chloro-6-{2,6-difluoro-4-[3-(methylamino)propoxy]phenyl}-N-[(1S)-2,2,2-trifluoro-1-methylethyl][1,2,4]triazolo[1,5-a]pyrimidin-7-amine fumarate salt (Example 2b) obtained are crystalline and are different crystalline structures. A Philips X'Pert PW3040 X-ray diffractometer is used to collect the diffraction data. The diffraction intensity is collected every 0.01° or 0.02° between 2-theta angle of 4° and 40°. A normal θ/2θ scan mode is used. Table 20 lists the peak positions or 2-theta angles of the corresponding powder XRD patterns.

TABLE 20

Peaks positions of the succinate salt (Example 2c) and fumarate salt (Example 2b)
2-Theta angle (degree)*

| Anhydrous Succinate | Hydrated Succinate | Anhydrous Fumarate | Hydrated Fumarate |
|---|---|---|---|
| 5.6 | 5.1 | 5.4 | 5.1 |
| 7.4 | 7.3 | 7.5 | 7.3 |
| 10.7 | 8.0 | 10.7 | 7.9 |
| 11.0 | 9.9 | 14.0 | 9.8 |
| 13.6 | 10.2 | 14.3(w) | 10.2 |
| 14.1(w) | 11.1 | 14.6 | 11.2 |
| 14.6(w) | 13.9 | 15.0 | 13.8(b) |
| 14.9 | 14.4(w) | 16.0 | 14.4 |
| 15.5 | 14.7 | 16.2 | 14.6 |
| 16.0 | 15.4 | 17.0 | 14.8 |
| 16.7(w) | 15.8 | 17.6 | 15.3 |
| 16.9 | 16.6(w) | 18.6 | 15.8 |
| 17.4 | 17.2 | 19.1 | 16.0 |
| 18.0 | 17.7(w) | 20.1 | 16.3(w) |
| 18.4 | 18.5 | 21.2 | 16.5(w) |
| 19.3 | 19.5 | 21.6 | 17.2 |
| 20.1(b) | 19.8 | 22.0 | 17.6(w) |
| 20.5 | 20.5 | 22.3 | 18.4 |
| 20.7(w) | 20.9 | 22.7 | 19.4 |
| 22.2 | 21.5 | 23.2 | 19.6 |
| 22.5(w) | 22.4 | 23.5 | 19.8(w) |
| 22.7 | 23.3 | 24.6 | 20.5 |
| 23.7 | 23.9 | 25.3 | 20.8 |
| 24.6(b) | 25.1(w) | 25.6 | 21.1 |
| 25.3 | 25.4 | 26.1 | 21.5 |
| 25.9 | 25.7 | 27.1(w) | 22.0 |
| 26.2(b) | 26.5 | 27.5 | 22.5 |
| 26.8 | 27.7(b) | 28.1 | 23.2 |
| 27.8 | 28.4 | 28.7 | 23.6(w) |
| 28.4 | 28.8 | 29.6 | 24.0 |
| 29.0(w) | 29.8 | 29.8 | 24.4(w) |
| 29.4 | 30.2 | 30.4 | 25.2 |
| 30.6(w) | 30.9 | 30.7 | 25.8 |
| 31.2(b) | 31.9 | 31.1 | 26.1 |
| 32.0 | 32.6 | 31.7 | 26.7 |
| 32.4 | 33.0 | 32.2 | 27.4(w) |
| 33.0 | 33.5(b) | 32.8 | 27.6 |
| 33.4 | 34.7(b) | 33.2 | 28.1(w) |
| 34.3(b) | 35.4(w) | 33.7 | 28.3(w) |
| 35.3 | 35.8 | 34.2(w) | 28.6 |
| 36.6 | 36.3(b) | 34.4 | 28.9(b) |
| 37.5 | 36.6 | 34.9(b) | 29.4 |
| 38.2(w) | 37.4 | 35.5 | 29.9 |
| 38.9 | 38.1 | 36.0 | 30.2(b) |
|  | 38.8(b) | 36.7 | 30.5 |
|  | 39.2 | 37.1 | 31.0 |
|  |  | 38.2(b) | 31.6 |
|  |  | 39.1 | 32.2 |
|  |  | 39.7(b) | 32.4 |
|  |  |  | 32.8 |
|  |  |  | 33.3 |
|  |  |  | 33.9 |
|  |  |  | 34.7(w) |
|  |  |  | 34.9 |
|  |  |  | 35.6 |
|  |  |  | 36.2 |
|  |  |  | 36.5 |
|  |  |  | 37.2 |
|  |  |  | 37.6(w) |
|  |  |  | 38.3(b) |
|  |  |  | 39.4 |

*w = weak, b = broad
Very weak peaks are marked as (w)
Relatively broad peaks are marked with (b).

What is claimed is:

1. A compound of Formula (I):

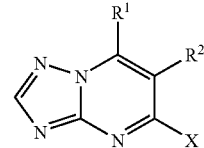

(I)

wherein:

$R^1$ is selected from

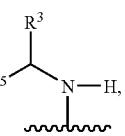

and $C_6$-$C_8$ cycloalkyl optionally substituted with $R^8$;

$R^2$ is a moiety of the group

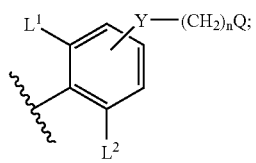
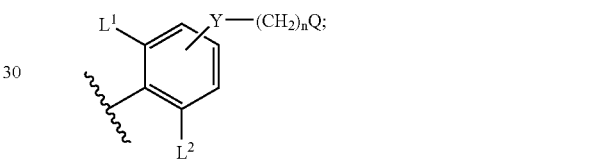

n is an integer of 2, 3, or 4;

X is Cl or Br;

Y is S, $CH_2$ or $NR^4$;

Q is selected from —$NR^6R^7$ and —OH;

$L^1$ and $L^2$ are each independently H, F, Cl, Br, or $CF_3$;

$R^3$ is $CF_3$ or $C_2F_5$;

$R^4$ and $R^5$ are each independently H or $C_1$-$C_3$ alkyl;

$R^6$ and $R^7$ are each independently H or $C_1$-$C_3$ alkyl; or $R^6$ and $R^7$ when optionally taken together with the nitrogen atom to which each is attached form a 4 to 6 membered saturated heterocyclic ring with 1-2 nitrogen atoms, 0-1 oxygen atoms and 0-1 sulfur atoms, and optionally substituted with $R^8$;

$R^8$ is $C_1$-$C_3$ alkyl;

or pharmaceutically acceptable salts thereof.

2. A compound according to claim 1, represented by formula (Ia)

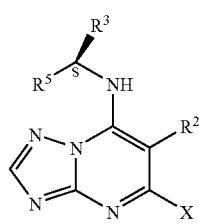

(Ia)

or pharmaceutically acceptable salts thereof.

3. A compound according to claim 1, represented by formula (Ib)

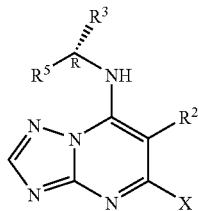

or pharmaceutically acceptable salts thereof.

4. A compound according to claim 1 wherein $R^2$ is

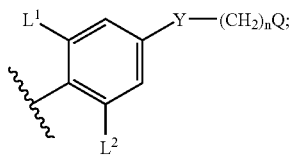

or pharmaceutically acceptable salts thereof.

5. A compound according to claim 1 wherein $R^1$ is $C_6$-$C_8$ cycloalkyl optionally substituted with $R^8$ or pharmaceutically acceptable salts thereof.

6. The compound according to claim 1, 5-chloro-6-(4-{[3-(dimethylamino)propyl]thio}-2,6-difluorophenyl)-N-[(1S)-2,2,2-trifluoro-1-methylethyl][1,2,4]triazolo[1,5-a]pyrimidin-7-amine or pharmaceutically acceptable salts thereof.

7. The compound according to claim 1, 2-[4-(5-chloro-7-{[(1S)-2,2,2-trifluoro-1-methylethyl]amino}[1,2,4]triazolo[1,5-a]pyrimidin-6-yl)-3,5-difluorophenoxy]ethanol or pharmaceutically acceptable salts thereof.

8. The compound according to claim 1, 3-[4-(5-chloro-7-{[(1S)-2,2,2-trifluoro-1-methylethyl]amino}[1,2,4]triazolo[1,5-a]pyrimidin-6-yl)-3,5-difluorophenoxy]propan-1-ol or pharmaceutically acceptable salts thereof.

9. The compound according to claim 1, $N^1$-[4-(5-chloro-7-{[(1S)-2,2,2-trifluoro-1-methylethyl]amino}[1,2,4]triazolo[1,5-a]pyrimidin-6-yl)-3,5-difluorophenyl]-$N^1$, $N^3$, $N^3$-trimethylpropane-1,3-diamine or pharmaceutically acceptable salts thereof.

10. The compound according to claim 1, $N^1$-[4-(5-chloro-7-{[(1S)-2,2,2-trifluoro-1-methylethyl]amino}[1,2,4]triazolo[1,5-a]pyrimidin-6-yl)-3,5-difluorophenyl]-$N^3$, $N^3$-dimethylpropane-1,3-diamine or pharmaceutically acceptable salts thereof.

11. The compound according to claim 1, $N^1$-[4-(5-chloro-7-{[(1S)-2,2,2-trifluoro-1-methylethyl]amino}[1,2,4]triazolo[1,5-a]pyrimidin-6-yl)-3,5-difluorophenyl]-$N^2$, $N^2$-dimethylethane-1,2-diamine or pharmaceutically acceptable salts thereof.

12. The compound according to claim 1, 5-chloro-6-{4-[4-(dimethylamino)butyl]-2,6-difluorophenyl}-N-[(1S)-2,2,2-trifluoro-1-methylethyl][1,2,4]triazolo[1,5-a]pyrimidin-7-amine or pharmaceutically acceptable salts thereof.

13. A compound according to claim 1 or pharmaceutically acceptable salts thereof selected from the group:

5-chloro-6-(4-{[3-(dimethylamino)propyl]thio}-2,6-difluorophenyl-N-[(1R)-2,2,2-trifluoro-1-methylethyl][1,2,4]triazolo[1,5-a]pyrimidin-7-amine, $N^1$-[4-(5-chloro-7-{[(1R)-2,2,2-trifluoro-1-methylethyl]amino}[1,2,4]triazolo[1,5-a]pyrimidin-6-yl)-3,5-difluorophenyl]-$N^1$, $N^3$, $N^3$-trimethylpropane-1,3-diamine, $N^1$-[4-(5-chloro-7-{[(1R)-2,2,2-trifluoro-1-methylethyl]amino}[1,2,4]triazolo[1,5-a]pyrimidin-6-yl)-3,5-difluorophenyl]-$N^3$,$N^3$-dimethylpropane-1,3-diamine, $N^1$-[4-(5-chloro-7-{[(1R)-2,2,2-trifluoro-1-methylethyl]amino}[1,2,4]triazolo[1,5-a]pyrimidin-6-yl)-3,5-difluorophenyl]-$N^2$, $N^2$-dimethylethane-1,2-diamine and 5-chloro-6-{4-[4-(dimethylamino)butyl]-2,6-difluorophenyl}-N-[(1R)-2,2,2-trifluoro-1-methylethyl][1,2,4]triazolo[1,5-a]pyrimidin-7-amine.

14. A pharmaceutical composition which comprises an effective amount of a compound of claim 1 or a pharmaceutically acceptable salt thereof together with a pharmaceutically acceptable carrier.

15. A process for the preparation of a compound of Formula (I)

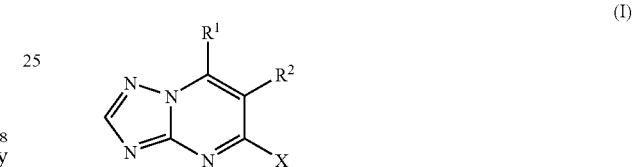

wherein:

$R^1$ is

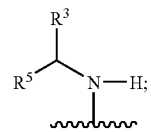

$R^2$ is a moiety

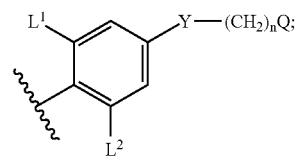

n is an integer of 2, 3, or 4;

X is Cl or Br;

Y is S, or $NR^4$;

Q is selected from —$NR^6R^7$ and —OH;

$L^1$ and $L^2$ are each independently H, F, Cl, Br or $CF_3$;

$R^3$ is $CF_3$ or $C_2F_5$;

$R^4$ and $R^5$ are each independently H or $C_1$-$C_3$ alkyl;

$R^6$ and $R^7$ are each independently H or $C_1$-$C_3$ alkyl; or $R^6$ and $R^7$ when optionally taken together with the nitrogen atom to which each is attached form a 4 to 6 membered saturated heterocyclic ring with 1-2 nitrogen atoms, 0-1 oxygen atoms and 0-1 sulfur atoms, and optionally substituted with $R^8$;

$R^8$ is $C_1$-$C_3$ alkyl;

comprising the step of reacting a compound of formula (II)

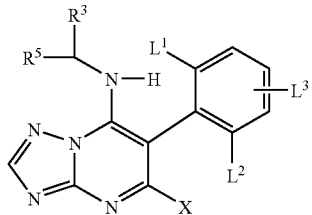

where $L^3$ is a leaving group with a compound of the formula $HY\!-\!(CH_2)_nQ$ in the presence of a strong base optionally in the presence of an aprotic solvent to give a compound of Formula (I) and pharmaceutically acceptable salts thereof.

16. A process according to claim 15 wherein the leaving group $L^3$ is F.

17. A process according to claim 15 wherein the strong base is selected from an alkali metal hydroxide, alkali metal carbonate and alkali metal hydride.

18. A process according to claim 15 wherein the aprotic solvent is selected from dimethylsulfoxide and dimethylformamide.

19. A process according to claim 15 wherein formula (II) is represented by the formula

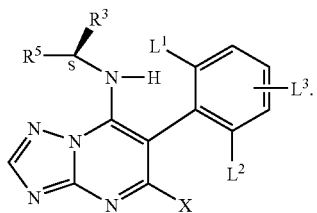

20. A process for the preparation of a compound of Formula (I)

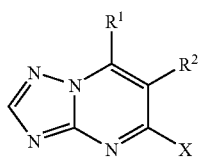

wherein:

$R^1$ is

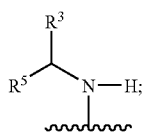

$R^2$ is a moiety of the group

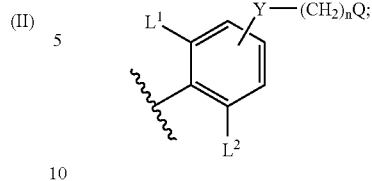

n is an integer of 2, 3, or 4;
X is Cl or Br;
Y is $CH_2$;
Q is $-NR^6R^7$;
$L^1$ and $L^2$ are each independently H, F, Cl, Br or $CF_3$;
$R^3$ is $CF_3$ or $C_2F_5$;
$R^5$ is H or $C_1$-$C_3$ alkyl;
$R^6$ and $R^7$ are each independently H or $C_1$-$C_3$ alkyl; or
$R^6$ and $R^7$ when optionally taken together with the nitrogen atom to which each is attached form a 4 to 6 membered saturated heterocyclic ring with 1-2 nitrogen atoms, 0-1 oxygen atoms and 0-1 sulfur atoms, and optionally substituted with $R^8$;
$R^8$ is $C_1$-$C_3$ alkyl;

and pharmaceutically acceptable salts thereof comprising the steps of:

a) reacting diester (III)

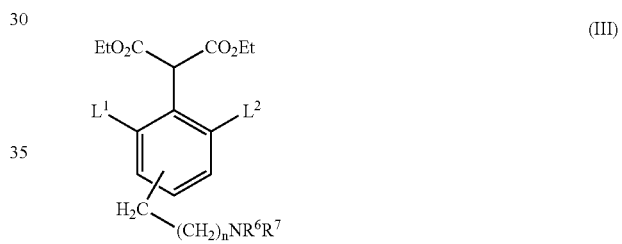

with 2-amino-1,3,4-triazole in the presence of a tertiary base to afford a compound (V) of the formula

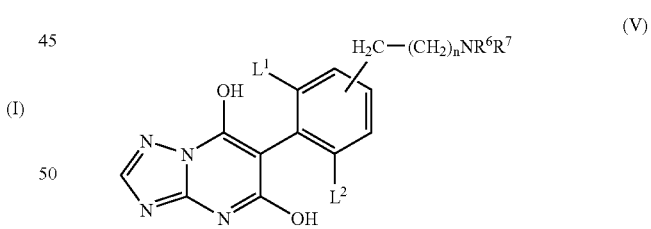

b) halogenating compound (V) with $POX_3$ to afford 5,7-dihalo compound (VI)

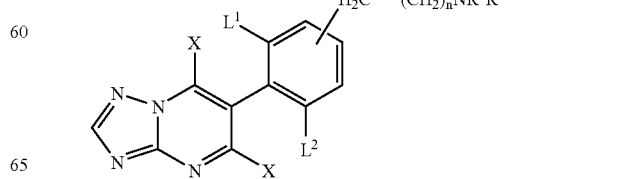

c) reacting the 5,7-dihalo compound (VI) with amine (VII)

(VII)

in the presence of base in an aprotic solvent to afford compounds of Formula (I) where Y is —$CH_2$—

(I)

and pharmaceutically acceptable salts thereof.

21. A process according to claim 20 wherein the base is N,N-diisopropylethylamine.

22. A process according to claim 20 wherein the aprotic solvent is selected from dimethylsulfoxide and dimethylformamide.

23. A process according to claim 20 wherein the amine (VII)

(VII)

has the (S) configuration.

24. A compound of Formula (I)

(I)

wherein:
$R^1$ is $R^2$ is a moiety n is an integer of 2, 3, or 4;
X is Cl or Br;
Y is S, or $NR^4$;
Q is selected from —$NR^6R^7$ and —OH;
$L^1$ and $L^2$ are each independently H, F, Cl, Br or $CF_3$;
$R^3$ is $CF_3$ or $C_2F_5$;
$R^4$ and $R^5$ are each independently H or $C_1$-$C_3$ alkyl;
$R^6$ and $R^7$ are each independently H or $C_1$-$C_3$ alkyl; or
$R^6$ and $R^7$ when optionally taken together with the nitrogen atom to which each is attached form a 4 to 6 membered saturated heterocyclic ring with 1-2 nitrogen atoms, 0-1 oxygen atoms and 0-1 sulfur atoms, and optionally substituted with $R^8$;
$R^8$ is $C_1$-$C_3$ alkyl;
and pharmaceutically acceptable salts thereof
produced by the process which comprises the step of reacting a compound of Formula (II)

(II)

where $L^3$ is a leaving group with a compound of the formula HY—$(CH_2)_n$Q in the presence of a strong base optionally in the presence of an aprotic solvent to give a compound of Formula (I) and pharmaceutically acceptable salts thereof.

25. A compound produced by the process according to claim 24 wherein the leaving group $L^3$ is F.

26. A compound produced by the process according to claim 24 wherein the strong base is selected from an alkali metal hydroxide, alkali metal carbonate and alkali metal hydride.

27. A compound produced by the process according to claim 24 wherein the aprotic solvent is selected from dimethylsulfoxide and dimethylformamide.

28. A compound produced by the process according to claim 24 wherein Formula (II) is represented by the formula 29. A compound of Formula (I)

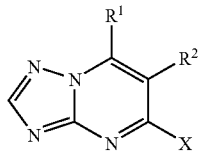

wherein:

R¹ is

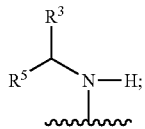

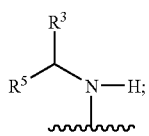

R² is a moiety of the group

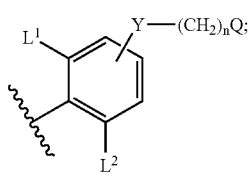

n is an integer of 2, 3, or 4;
X is Cl or Br;
Y is $CH_2$;
Q is $-NR^6R^7$;
$L^1$ and $L^2$ are each independently H, F, Cl, Br or $CF_3$;
$R^3$ is $CF_3$ or $C_2F_5$;
$R^5$ is H or $C_1$-$C_3$ alkyl;
$R^6$ and $R^7$ are each independently H or $C_1$-$C_3$ alkyl; or
$R^6$ and $R^7$ when optionally taken together with the nitrogen atom to which each is attached form a 4 to 6 membered saturated heterocyclic ring with 1-2 nitrogen atoms, 0-1 oxygen atoms and 0-1 sulfur atoms, and optionally substituted with $R^8$;
$R^8$ is $C_1$-$C_3$ alkyl;

and pharmaceutically acceptable salts thereof,
produced by the process which comprises the steps of:
a) reacting diester (III)

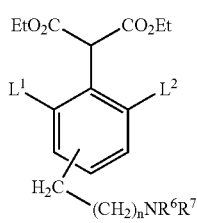

with 2-amino-1,3,4-triazole in the presence of a tertiary amine base to afford a compound (V) of the formula

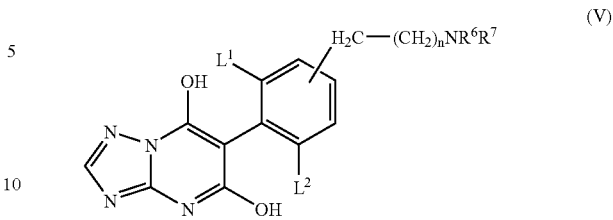

b) halogenating compound (V) with $POX_3$ to afford 5,7-dihalo compound (VI)

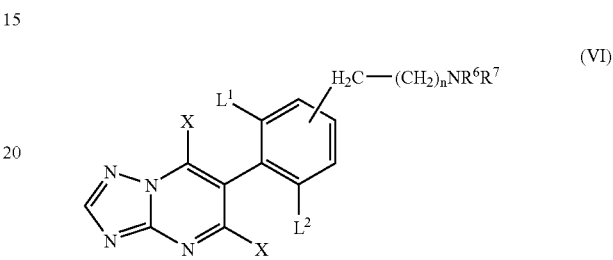

c) reacting the 5,7-dihalo compound (VI) with amine (VII)

in the presence of base in an aprotic solvent to afford compounds of Formula (I) where Y is $-CH_2-$,

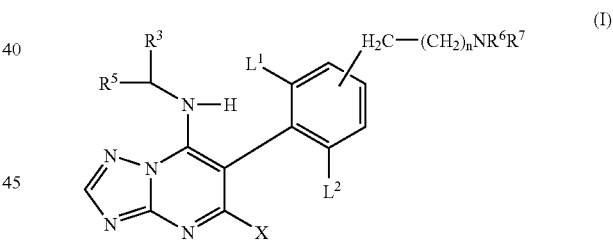

and pharmaceutically acceptable salts thereof.

30. A compound produced by the process according to claim 29 wherein the base is N,N-diisopropylethylamine.

31. A compound produced by the process according to claim 29 wherein the aprotic solvent is selected from dimethylsulfoxide and dimethylformamide 32. A compound produced by the process according to claim 29 wherein the amine (VII)

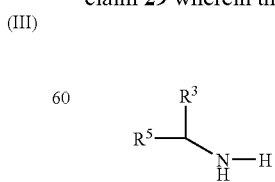

has the (S) configuration.

* * * * *